United States Patent
Babich et al.

(10) Patent No.: US 8,211,402 B2
(45) Date of Patent: *Jul. 3, 2012

(54) CA-IX SPECIFIC RADIOPHARMACEUTICALS FOR THE TREATMENT AND IMAGING OF CANCER

(75) Inventors: John W. Babich, Cambridge, MA (US); Craig Zimmerman, Topsfield, MA (US); John Joyal, Melrose, MA (US); Kevin P. Maresca, Tewksbury, MA (US); Genliang Lu, Winchester, MA (US); Shawn Hillier, Danvers, MA (US)

(73) Assignee: Molecular Insight Pharmaceuticals, Inc., Cambridge, MA (US)

( * ) Notice: Subject to any disclaimer, the term of this patent is extended or adjusted under 35 U.S.C. 154(b) by 396 days.

This patent is subject to a terminal disclaimer.

(21) Appl. No.: 12/631,343

(22) Filed: Dec. 4, 2009

(65) Prior Publication Data

US 2010/0178247 A1 Jul. 15, 2010

Related U.S. Application Data

(60) Provisional application No. 61/120,226, filed on Dec. 5, 2008, provisional application No. 61/180,341, filed on May 21, 2009.

(51) Int. Cl.
| | |
|---|---|
| A61K 51/04 | (2006.01) |
| A61K 31/444 | (2006.01) |
| A61K 31/555 | (2006.01) |
| A61K 49/00 | (2006.01) |
| C07D 401/12 | (2006.01) |
| C07F 13/00 | (2006.01) |
| A61P 35/00 | (2006.01) |

(52) U.S. Cl. ........ 424/1.65; 424/9.1; 514/184; 514/188; 514/332; 514/492; 534/14; 546/10; 546/12; 546/265; 546/5; 548/104; 548/109; 556/1; 556/50

(58) Field of Classification Search ................... None
See application file for complete search history.

(56) References Cited

U.S. PATENT DOCUMENTS

| | | | |
|---|---|---|---|
| 2,730,456 A | 1/1956 | Green et al. | |
| 2,730,457 A | 1/1956 | Green et al. | |
| 2,800,457 A | 7/1957 | Green et al. | |
| 3,625,214 A | 12/1971 | Higuchi | |
| 4,272,398 A | 6/1981 | Jaffe | |
| 4,798,734 A | 1/1989 | Kaneda | |

(Continued)

FOREIGN PATENT DOCUMENTS

EP 1 389 460 A1 2/2004

(Continued)

OTHER PUBLICATIONS

Alberto et al., "A Novel Organometallic Aqua Complex of Technetium for the Labeling of Biomolecules: Synthesis of [99Tc(OH2)3(CO3] [99mTcO4]- in Aqueous Solution and Its Reaction with a Bifunctional Ligand", Journal of American Chemical Society, American Chemical Society, vol. 120, No. 31, 1998, pp. 7987-7988. Banerjee et al., "{RE(III)CI3} Core Complexes with Bifunctional Single Amino Acid Chelates", Inorganic Chemistry, American Chemical Society, vol. 41, No. 22, 2002, pp. 5795-5802.
Banerjee et al.,Bifunctional Single Amino Acid Chelates for Labeling of Biomolecules with the {Tc(CO)3} and {Re(CO)3} Cores. Crystal and Molecular Structures of [ReBr(CO)3(H2NCH2C5H4N)], [Re(CO)3{C5H4NCH2}2NH)Br, [Re(CO)3{C5H4NCH2)2NCH2CO2H}Br, [Re(CO)3{X(Y)NCH2CO2CH2CH3}Br(X=Y=2-pyridylmethyl; X=2-pyridylmethyl, Y=2-(1-methylimidazolyl)methyl,[ReBr(CO) 3{C5H4NCH2)NH (CH2C4H3S)}], and [Re(CO)3{C5H4NCH2)N(CH2C4H3S)(CH2CO2)}], Inorganic Chemistry, vol. 41, No. 24, 2002, pp. 6417-6425.

(Continued)

Primary Examiner — Sun Jae Loewe
(74) Attorney, Agent, or Firm — Gilberto M. Villacorta; Jeffrey R. Lomprey; Foley & Lardner LLP

(57) ABSTRACT

A compound that recognizes and binds to the CA-IX protein has Formula I, II, III, or IV. The compounds may include a radioactive element for radioimaging or therapeutic applications. Thus, pharmaceutical compositions may be prepared with one or more of the compounds of Formula I, II, III, or IV.

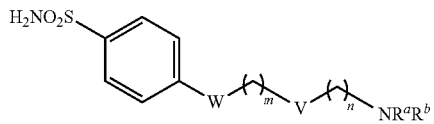

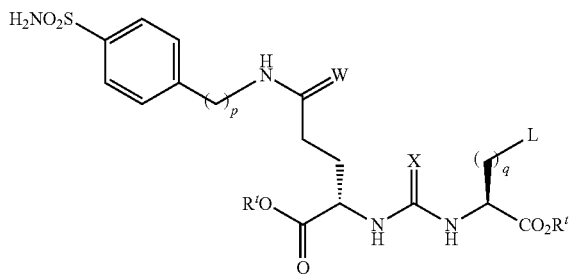

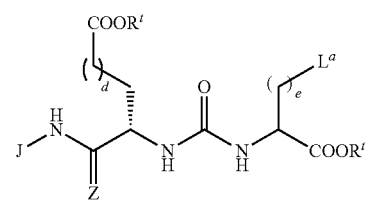

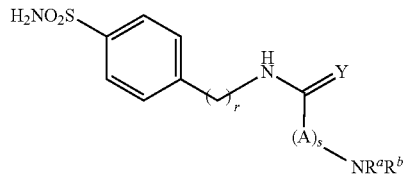

33 Claims, 3 Drawing Sheets

U.S. PATENT DOCUMENTS

| | | | |
|---|---|---|---|
| 4,906,474 | A | 3/1990 | Langer et al. |
| 4,925,673 | A | 5/1990 | Steiner et al. |
| 2003/0235843 | A1 | 12/2003 | Babich et al. |
| 2004/0191174 | A1 | 9/2004 | Linder et al. |
| 2004/0209921 | A1 | 10/2004 | Bridger et al. |
| 2005/0038258 | A1 | 2/2005 | Koike et al. |
| 2006/0057068 | A1 | 3/2006 | Supuran et al. |
| 2008/0227962 | A1 | 9/2008 | Mazzanti |
| 2009/0175794 | A1 | 7/2009 | Zimmerman et al. |
| 2010/0178246 | A1 | 7/2010 | Babich et al. |
| 2010/0183509 | A1* | 7/2010 | Babich et al. ............ 424/1.65 |

FOREIGN PATENT DOCUMENTS

| | | | |
|---|---|---|---|
| EP | 1 550 657 | A1 | 7/2005 |
| EP | 1 961 744 | A1 | 8/2008 |
| JP | 04-342560 | | 11/1992 |
| WO | WO-03/013617 | A2 | 2/2003 |
| WO | WO-03/077727 | A2 | 9/2003 |
| WO | WO-2004/014352 | A2 | 2/2004 |
| WO | WO-2004/048544 | A2 | 6/2004 |
| WO | WO-2005/056520 | A1 | 6/2005 |
| WO | WO-2005/079865 | | 9/2005 |
| WO | WO-2006/080993 | | 8/2006 |
| WO | WO-2007/090461 | A1 | 8/2007 |
| WO | WO-2007/148738 | A1 | 12/2007 |
| WO | WO-2008/028000 | A2 | 3/2008 |
| WO | WO-2008/058192 | A2 | 5/2008 |
| WO | WO-2009/076434 | A1 | 6/2009 |
| WO | WO-2009/089383 | A2 | 7/2009 |
| WO | WO2010065899 | * | 12/2009 |
| WO | WO-2010/036814 | A1 | 4/2010 |
| WO | WO-2010/065906 | A2 | 6/2010 |

OTHER PUBLICATIONS

Banerjee et al., "Synthesis and Evaluation of Technetium-99m- and Rhenium-Labeled Inhibitors of the Prostate-Specific Membrane Antigen (PSMA)", Journal of Medicinal Chemistry, vol. 15, pp. 4504-4517, 2008.

Benita, S. et al., "Characterization of Drug-Loaded Poly(d,l-lactide) Microspheres," Journal of Pharmaceutical Sciences, vol. 73, No. 12, Dec. 1984, pp. 1721-1724.

Berge et al., "Pharmaceuticals Salts," J. Pharm. Sci, vol. 66, No. 1, pp. 1-19., 1977.

Bonomi et al., Renato, "Phosphate Diester and DNA Hydrolysis by a Multivalent, Nanoparticle-Based Catalyst", Journal of the American Chemical Society, vol. 130, 2008, pp. 15744-15745.

Casini, Angela et al., "Carbonic Anhydrase Inhibitors: Synthesis of Water Soluble Sulfonamides Incorporating a 4-sulfamoylphenylmethylthiourea Scaffold, with Potent Intraocular Pressure Lowering Properties," Journal of Enzyme Inhibition and Medicinal Chemistry, 2002, vol. 17, No. 5, pp. 333-343.

Cecchi et al.., Alessandro, "Carbonic Anhydrase Inhibitors. Design of Fluorescent Sulfonamides as Probes of Tumor-assoicated Carbonic Anhydrase IX that Inhibit Isozyme IX-Mediated Acidification of Hypoxic Tumores," Journal of Medicinal Cheimistry, vol. 48, No. 15, Jul. 2005, pp. 4834-4841.

Database Beilstein [Online]; Beilstein Institute for Organic Chemistry, 1958, Database Accession No. Citation No. 990210, XP002577062.

Deasy, Patrick et al., Microencapsulation and Related Drug Processes, 1984, School of Pharmacy, University of Dublin, Marcel Dekker, Inc.

Feng, et al., Guoqiang, "Comparing a mononuclear Zn(II)complex with hydrogen bond donors with a dinuclear Zn(II) complex for catalysing phosphate ester cleavage",The Royal Society of Chemistry, 2006, pp. 1845-1847.

Greene, T. W. et al., Protective Groups in Organic Synthesis, Second Edition, Wiley, New York, 1991.

Greene T. W. et al., Protective Groups in Organic Synthesis, Third Edition, Wiley, New York, 1999.

Gregoriadis, G., et al., Drug Carriers in Biology and Medicine, Chapter 14: Liposomes, pp. 287-341.

Henson et al., Mark J., "Resonance Raman Investigation of Equatorial Ligand Donor Effects on the Cu2O22 Core in End-On and Side-On u-Perozo-Dicopper(II) and Bis-u-oxo-Dicopper(III) Complexes", Journal of American Chemical Society, vol. 125, 2003, pp. 5186-5192.

International Search Report and Written Opinion mailed Jun. 26, 2009 in International Application No. PCT/US2009/030487.

International Search Report and Written Opinion mailed Oct. 14, 2010 in International Application No. PCT/US2009/066832.

International Search Report and Written Opinion mailed Dec. 28, 2010 in International Application No. PCT/US2009/066836.

Invitation to Pay Additional Fees mailed May 17, 2010 in International Application No. PCT/US2009/066832.

Invitation to Pay Additional Fees mailed May 17, 2010 in International Application No. PCT/US2009/066836.

Invitation to Pay Additional Fees mailed May 17, 2010 in International Application No. PCT/US2009/066842.

Jalil, R. et al., "Biodegradable poly(lactic acid) and poly(lactide-co-glycolide) microcapsules: problems associated with preparative techniques and release properties", J. Microencapsulation, 1990, vol. 7, No. 3, pp. 297-325.

Kojima et al., "Synthesis and Characterization of Mononuclear Ruthenium (III) Pyridylamine Complexes and Mechanistic Insights into Their Catalytic Alkane Functionalization with m-Chloroperbenzoic Acid", Chemistry, vol. 13, 2007, pp. 8212-8222.

Krebs, H.A., "Inhibition of Carbonic Anhydrase by Sulphonamides," The Biochemical Journal, vol. 43, 1948, pp. 525-528.

Kularatne, S.A. et al., "Design, Synthesis, and Preclinical Evaluation of Prostate-Specific Membrane Antigen Targeted 99mTc-Radioimaging Agents," Molecular Pharmaceutics, vol. 6, No. 3, pp. 790-800.

Lewis et al., "Maleimidocysteineamido—DOTA Derivatives: New Reagents for Radiometal Chelate Conjugation to Antibody Sulfhydryl Groups Undergo pH-Dependent Cleavage Reactions", Bioconjugate Chemistry, American Chemical Society, vol. 9, No. 1, 1998, pp. 72-86.

Lim, Franklin et al, "Microencapsulation of Living Cells and Tissues," Journal of Pharmaceutical Sciences, Apr. 1981, vol. 70, No. 4, pp. 351-354.

Mathiowitz, E. et al., "Mophology of Polyanhydride Miscrosphere Delivery Systems," Scanning Microscopy, 1990, vol. 4, No. 2, pp. 329-340.

Mathiowitz, E. et al., "Polyanhydride Microspheres as Drug Carriers. II. Microencapsulation by Solvent Removal," Journal of Applied Polymer Science, 1988, vol. 35, pp. 755-774.

Nakano, M. et al., "Sustained Urinary Excretion of Sulfamethizole Following Oral Administration of Enteric Coated Microcapsules in Humans," International Journal of Pharmaceutics, 1980, vol. 4, pp. 291-298.

Nonat et al., Aline, "Structure, Stability, Dynamics, High-Field Relaxivity and Ternary-Complex Formation of a New Tris(aquo) Gadolinium Complex", Chemistry, vol. 13, 2007, pp. 8489-8506.

Roy et al, Bidham C., "Two-Prong Inhibitors for Human Carbonic Anhydrase II", Journal of American Chemical Society, vol. 126, 2004, pp. 13206-13207.

Salib, N. et al., "Utilization of Sodium Alginate in Drug Microencapsulation," Pharm. Ind., vol. 40, No. 11a, 1978, pp. 1230-1234.

Sawhney, A. et al., "Bioerodible Hydrogels Based on Photopolymerized Poly(ethylene glycol)-co-poly(a-hydroxy acid) Diacrylate Macromers," Macromolucules, vol. 26, 1993, pp. 581-587.

Thallaj, Nasser K., "A Ferrous Center as Reaction Site for Hydration of a Nitrile Group into a Carboxamide in Mild Conditions", Journal of American Chemical Society, vol. 130, 2007, pp. 2414-2415.

Thiry et al., "Targeting Tumor-Associated Carbonic Anhydrase IX in Cancer Therapy," Trends in Pharmacological Sciences, vol. 27, No. 11, Nov. 2006, pp. 566-573.

Yao, Zhen et al., Synthesis of Porphyrins Bearing 1-4 hydroxymethyl Groups and other One-carbon oxygenic Substituents in Distinct Patterns, Tetrahedron, vol. 63, 2007, pp. 10657-10670.

Dubois, L., et al., "Imaging the hypoxia surrogate marker CA IX requires expression and catalytic activity for binding fluorescent sulfonamide inhibitors," 2007, Radiotherapy and Oncology, vol. 83, pp. 367-373.

Pastorekov, S., et al., "Carbonic anhydrase IX (CA IX) as potential target for cancer therapy," 2004, Cancer Therapy, vol. 2. (19 pages).

Restriction Requirement received for U.S. Appl. No. 12/350,894, dated Jun. 10, 2011.

EPA, Commonly Encountered Radionuclides, 2011, http://www.epa.gov/radiation/radionuclides/ (2 pgs.).

Steffens MG, et al., "Targeting of Renal Cell Carcinoma with Iodine-131-Labeled Chimeric Monoclonal Antibody G250," J. Clin. Oncol., 15(4), 1997, pp. 1529-1537. (abstract).

Office Action mailed Sep. 8, 2011 in U.S. Appl. No. 12/350,894.

T6 Hanada et al., "Preparation of 2,8-diazaspiro[4.5]decane containing bis(imidazol-2-ylmethyl_amines as CXCR4 antagonists for treatment of inflammation and immune disease", caplus an 2008:159048, 5 pages.

Kusumi et al., "Preparation of heterocycle compounds having (un)protected acidic group as CXCR4 antagonists", caplus an 2007:1332283, 8 pages.

Notice of Allowance received for U.S. Appl. No. 12/631,337 dated Mar. 15, 2012.

Saitou et al., "Preparation of N-arylmethyl or N-hererocyclylmethyl-N-(imidazol-2-ymethyl)amines as antagonists of chemokine receptor CXCR4", caplus an 2005:1004718, 6 pages.

Non-final Office Action received for U.S. Appl. No. 12/631,312 dated Mar. 6, 2012.

* cited by examiner

CA-IX SPECIFIC RADIOPHARMACEUTICALS FOR THE TREATMENT AND IMAGING OF CANCER

CROSS-REFERENCE TO RELATED APPLICATIONS

This application claims the benefit of U.S. Provisional Patent Applications 61/120,226 filed on Dec. 5, 2008, and 61/180,341, filed on May 21, 2009, both of which are incorporated herein by reference in their entirety, for any and all purposes.

BACKGROUND

The present technology relates generally to the field of radiopharmaceuticals and their use in nuclear medicine as tracers, imaging agents and for the treatment of various disease states. It is well known that tumors may express unique proteins associated with their malignant phenotype or may over-express normal constituent proteins in greater number than normal cells. The expression of distinct proteins on the surface of tumor cells offers the opportunity to diagnose and characterize disease by probing the phenotypic identity and biochemical composition and activity of the tumor. Radioactive molecules that selectively bind to specific tumor cell surface proteins provide an attractive route for imaging and treating tumors under non-invasive conditions. In particular, the present inventors have found that radiolabeled ligands to the CA-IX protein, often over-expressed on many cancer cells provide an attractive route for non-invasive imaging and selective targeting of cancer cells.

Carbonic anhydrase (CA) or carbonate dehydrases are a family of enzymes that catalyzes the rapid conversion of carbon dioxide to bicarbonate and proton in the presence of water. Carbonic anhydrase, therefore, play an important role in maintaining the acid-base balance (pH), in blood and tissues and also play a role in transporting carbon dioxide out of tissues. CA is a zinc metalloenzyme, the active site zinc being coordinated to the imidazole residues of three histidine side chains.

There are at least 16 isozymes in the carbonic anhydrase family. Specific isozymes are found either in the cytosol, anchored to the membrane, within the mitochondria, or secreted from the cell. The well studied constitutively expressed isozyme, carbonic anhydrase II (CA-II), is found in the cytosol of most cell types, and is the primary isoform responsible for the regulation of intracellular pH.

CA-IX is a membrane-anchored isoform of the enzyme with its catalytic domain in the extracellular space. It has a limited tissue distribution and is found at low levels primarily in the gastrointestinal tract. The expression of CA-IX is under the control of HIF-1α, and this isozyme is highly expressed in tumors cells exposed to hypoxia both in vitro and in vivo. Increased CA-IX expression has been detected in carcinomas of the cervix, ovary, kidney, esophagus, lung, breast, and brain. The low extracellular pH as a result of the activity of CA-IX leads to tumorigenic transformation, chromosomal rearrangements, extracellular matrix breakdown, migration and invasion, induction of growth factors, protease activation, and chemoresistance. Accordingly, a correlation can be made between the cellular levels of CA-IX and tumor progression. Radiopharmaceuticals directed to the CA-IX protein thus provide an novel avenue for the non-invasive treatment of cancer.

The selective targeting of cancer cells with radiopharmaceuticals, either for imaging or therapeutic purposes is challenging. A variety of radionuclides are known to be useful for radioimaging, including Ga-67, Tc-99m, In-111, I-123, and I-131. The preferred radioisotope for medical imaging is Tc-99m, because it has a short (6 hour) half life, is readily available at relatively low cost and emits gamma-photons of 140 keV. Moreover, Tc-99m complexes, such as, water and air stable Tc(I) complex $[^{99m}Tc(OH_2)_3(CO)_3]^+$ complex can be readily prepared in saline under 1 atm of carbon monoxide (CO). Accordingly, bifunctional molecules that comprise a specific receptor honing bioactive molecule covalently tethered to a $^{99m}Tc$ or $^{186/188}Re$ coordination complex provide a novel system for the selective imaging and targeting of cancer cells.

SUMMARY

In one aspect, a compound of Formula I is provided

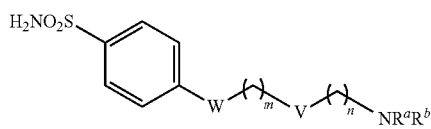

where: W is a bond, a $(C_1$-$C_8)$alkyl, a $(C_2$-$C_8)$alkenyl, an aryl, a heteroaryl, a —NHC(O), —C(O)NH, —NH—C(O)—NH—, or —NH—C(S)—NH—; V is a bond, a $(C_1$-$C_8)$alkyl, a $(C_2$-$C_8)$alkenyl, an aryl, a heteroaryl, —NH—C(O)—NH—, or —NH—C(S)—NH—; $NR^aR^b$ is a chelator group of Formula:

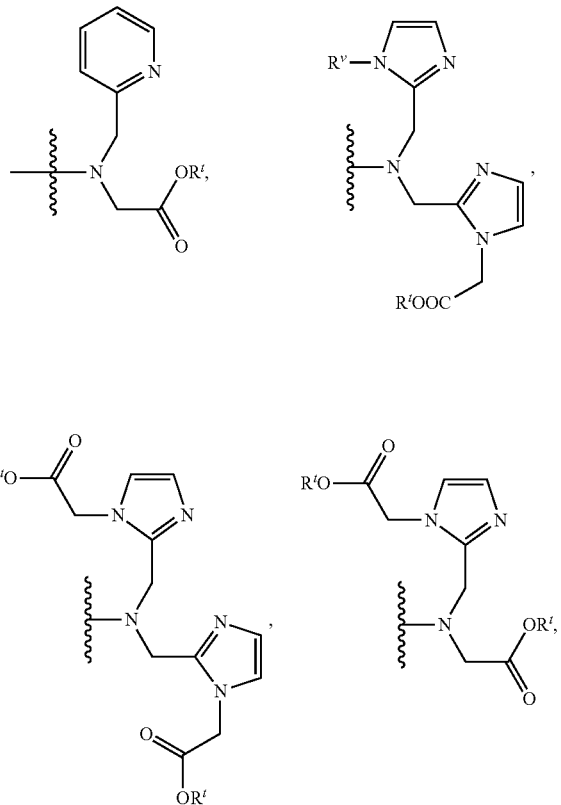

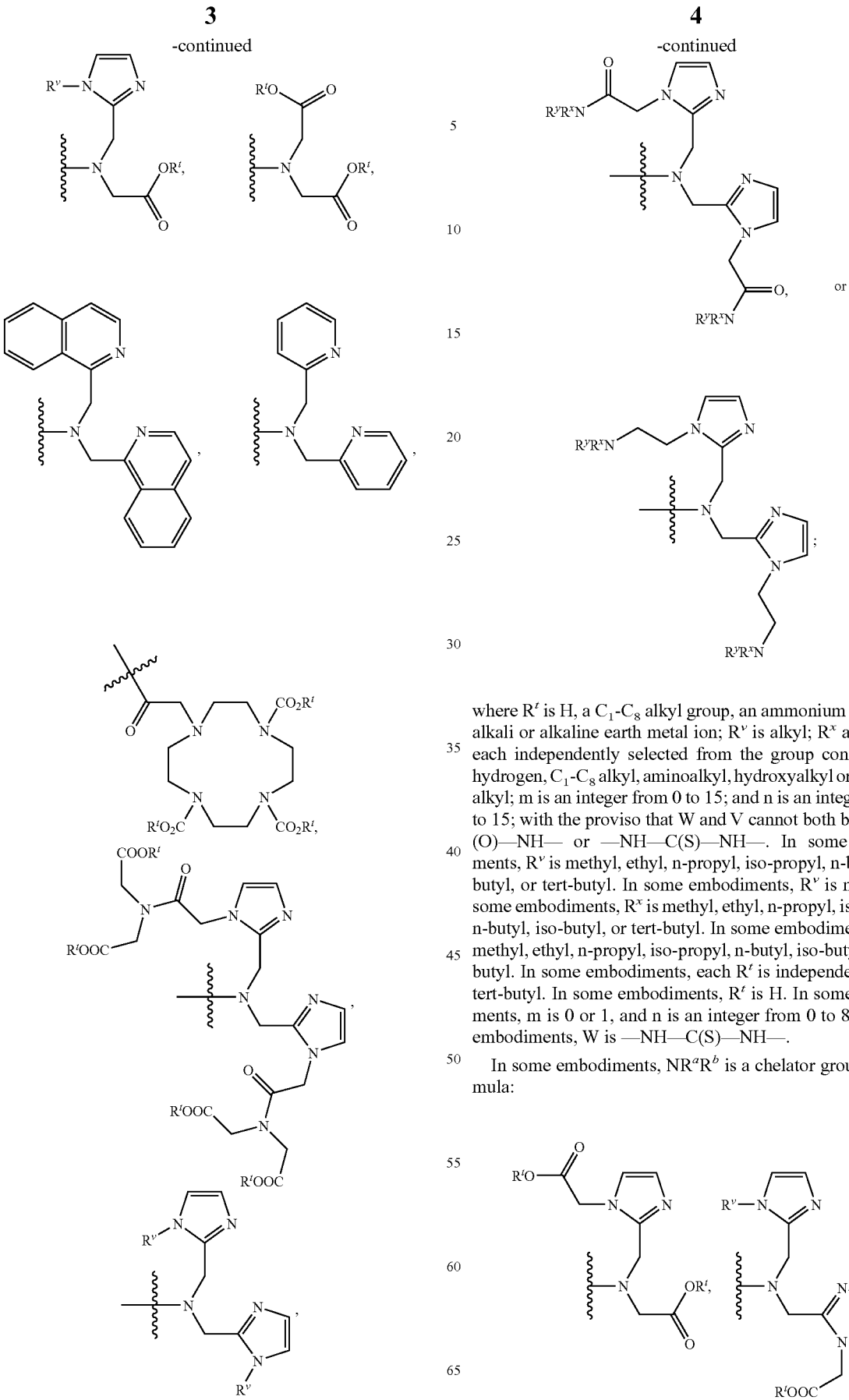

where $R^t$ is H, a $C_1$-$C_8$ alkyl group, an ammonium ion, or an alkali or alkaline earth metal ion; $R^v$ is alkyl; $R^x$ and $R^y$ are each independently selected from the group consisting of hydrogen, $C_1$-$C_8$ alkyl, aminoalkyl, hydroxyalkyl or carboxyalkyl; m is an integer from 0 to 15; and n is an integer from 0 to 15; with the proviso that W and V cannot both be NH—C(O)—NH— or —NH—C(S)—NH—. In some embodiments, $R^v$ is methyl, ethyl, n-propyl, iso-propyl, n-butyl, iso-butyl, or tert-butyl. In some embodiments, $R^v$ is methyl. In some embodiments, $R^x$ is methyl, ethyl, n-propyl, iso-propyl, n-butyl, iso-butyl, or tert-butyl. In some embodiments, $R^y$ is methyl, ethyl, n-propyl, iso-propyl, n-butyl, iso-butyl, or tert-butyl. In some embodiments, each $R^t$ is independently H or tert-butyl. In some embodiments, $R^t$ is H. In some embodiments, m is 0 or 1, and n is an integer from 0 to 8. In some embodiments, W is —NH—C(S)—NH—.

In some embodiments, $NR^aR^b$ is a chelator group of Formula:

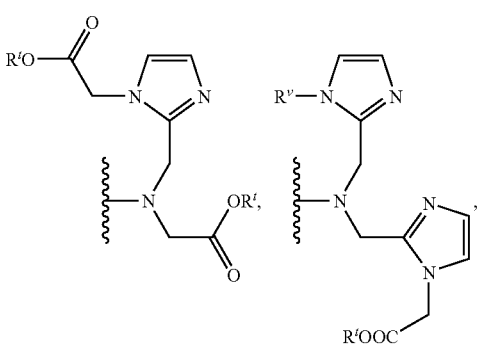

-continued

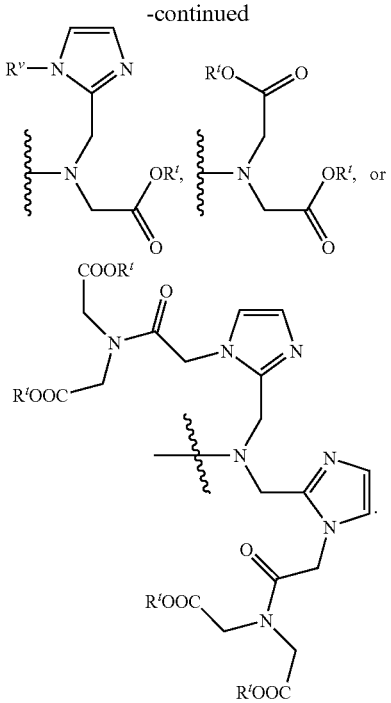

In some embodiments, $NR^aR^b$ is a chelator group of Formula:

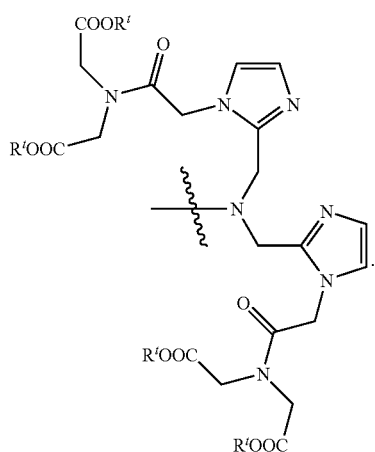

In some embodiments, $NR^aR^b$ is a chelator group of Formula:

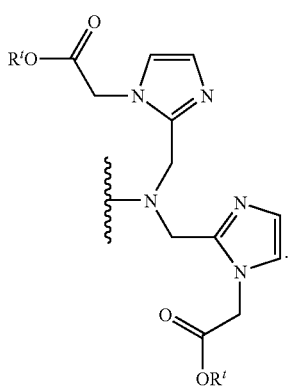

However, where $NR^aR^b$ is bis(methylene)bis(1H-imidazole-2,1-diyl))diacetic acid (the above formula, Formula I does not include the following compounds 2,2'-(2,2'-(8-(3-(4-sulfamoylphenyl)thioureido) octylazanediyl)-bis(methylene)bis (1H-imidazole-2,1-diyl))diacetic acid; 2,2'-(2,2'-(4-sulfamoylphenylazanediyl)-bis(1H-imidazole-2,1-diyl))diacetic acid; or 2,2'-(2,2'-(5-(4-sulfamoylbenzamido)pentylazanediyl)-bis(methylene)bis(1H-imidazole-2,1-diyl))diacetic acid.

In some embodiments, $NR^aR^b$ is a chelator group of Formula:

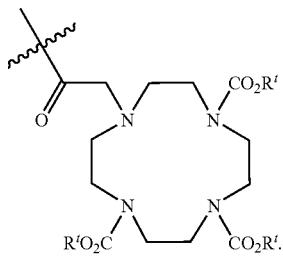

In some embodiments, the compound of Formula I has the structure:

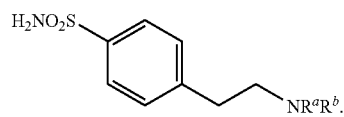

In another aspect, a compound of Formula II is provided:

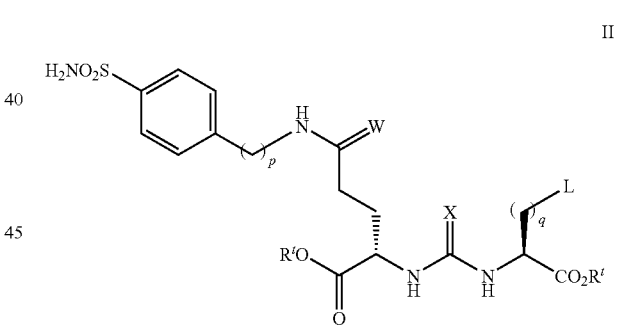

where, L is an $NR^aR^b$ chelator group as defined for the compound of Formula I or a group of formula:

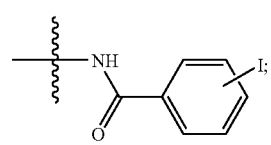

W and X are independently O or S; p is an integer from 0 to 5; q is an integer from 0 to 8; $R^t$ is H, a $C_1$-$C_8$ alkyl group, an ammonium ion, or an alkali or alkaline earth metal ion; and $R^v$ is an alkyl. In some embodiments, $R^v$ is methyl, ethyl, n-propyl, iso-propyl, n-butyl, iso-butyl, or tert-butyl. In some embodiments, $R^v$ is methyl. In some embodiments, each $R^t$ is independently H or tert-butyl. In some embodiments, $R^t$ is H.

In some embodiments of the compound of Formula II, L is a group of formula:

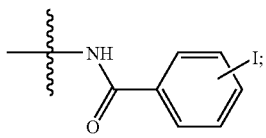

where, the iodine is I-123 or I-133. In other embodiments, L is a group of Formula:

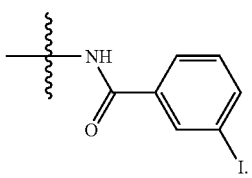

In some such embodiments, the iodine is I-123 or I-133.

In some embodiments, $NR^aR^b$ is a chelator group of Formula:

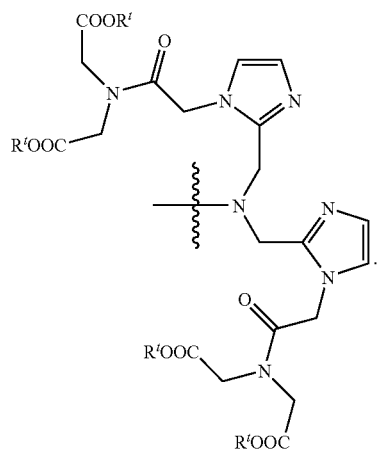

In some embodiments, $NR^aR^b$ is a chelator group of Formula:

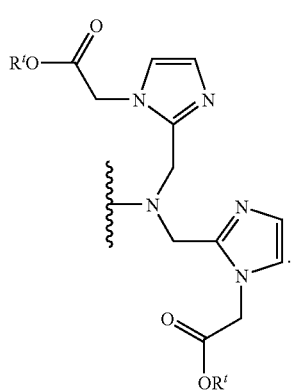

In some embodiments, $NR^aR^b$ is a chelator group of Formula:

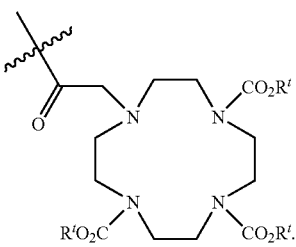

In another aspect, a compound of Formula III is provided:

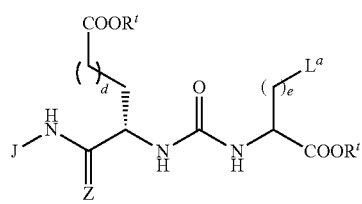

III where, J is aryl; Z is O or S; $L^a$ is an $NR^aR^b$ chelator group according to that of Formula I, or a group of formula:

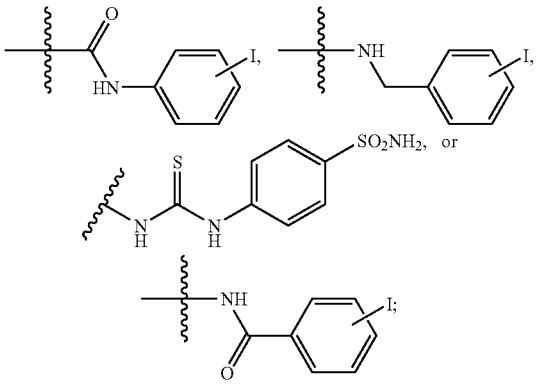

d is an integer from 0 to 5; e is an integer from 0 to 8; $R^t$ is H, a $C_1$-$C_8$ alkyl group, an ammonium ion, or an alkali or alkaline earth metal ion; and $R^v$ is an alkyl. In some embodiments, J is phenyl, naphthyl, or anthracene. In some embodiments, J is a monosubstituted or disubstituted phenyl group. In some such embodiments, the phenyl is monosubstituted with I, ($C_1$-$C_8$)alkyl, ($C_2$-$C_8$)alkenyl, —CN, —NO$_2$, —OH, —SH, —SO$_2$NH$_2$, or —NR$^c$R$^d$; wherein $R^c$ and $R^d$ are independently H, ($C_1$-$C_4$)alkyl, or aryl. In other such embodiments, J is di-substituted and a first substituent is I, ($C_1$-$C_8$)alkyl, ($C_2$-$C_8$)alkenyl, —CN, —NO$_2$, —OH, —SH, —SO$_2$NH$_2$, or —NR$^c$R$^d$; wherein $R^c$ and $R^d$ are independently H, ($C_1$-$C_4$) alkyl, or aryl; and a second substituent is ($C_1$-$C_8$)alkyl, ($C_2$-$C_8$)alkenyl, —OH, —SH, or halogen. In some embodiments, $R^v$ is methyl, ethyl, n-propyl, iso-propyl, n-butyl, iso-butyl, or tert-butyl. In some embodiments, $R^v$ is methyl. In some embodiments, each $R^t$ is independently H or tert-butyl. In some embodiments, $R^t$ is H.

In some embodiments of the compound of Formula III, $L^a$ is

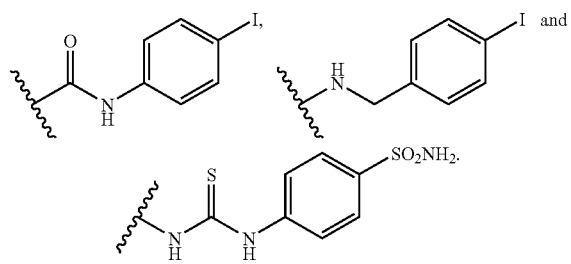

In some embodiments, $NR^aR^b$ is a chelator group of Formula:

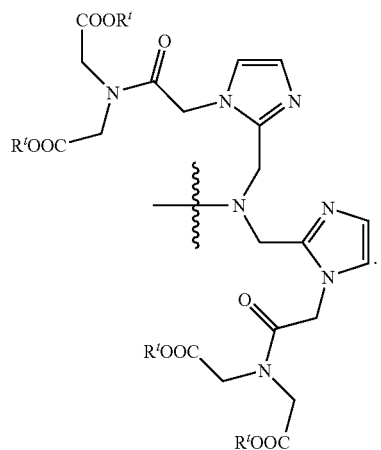

In some embodiments. $NR^aR^b$ is a chelator group of Formula:

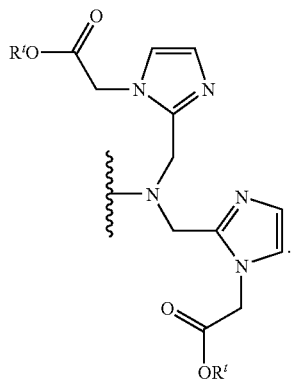

In some embodiments, $NR^aR^b$ is a chelator group of Formula:

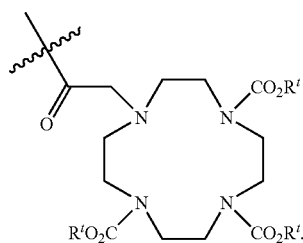

In some embodiments, a complex is provided including f the compound of Formula III, $L^a$ is an $NR^aR^b$ chelator group and the compound is complexed with a metal.

In another aspect, a compound of Formula IV is provided:

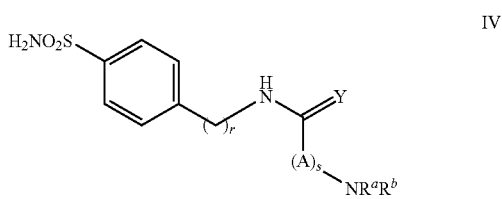

where, $NR^aR^b$ is a chelator group according to that of Formula I; Y is O or S; A is $(C_1\text{-}C_8)$alkyl, $-(CH_2)_x-$ $(OCH_2CH_2)_y-$ or $-(OCH_2CH_2)_y(CH_2)_x-$; x is an integer from 0 to 3; y is an integer from 0 to 3; r is an integer from 0 to 5; s is an integer from 0 to 10; $R^t$ is H, a $C_1\text{-}C_8$ alkyl group, an ammonium ion, or an alkali or alkaline earth metal ion; and $R^v$ is an alkyl. In some embodiments, r is 0, 1 or 2. In some embodiments, s is 0, 5, or 10. In some embodiments, $R^v$ is methyl, ethyl, n-propyl, iso-propyl, n-butyl, iso-butyl, or tert-butyl. In some embodiments, $R^v$ is methyl. In some embodiments, each $R^t$ is independently H or tert-butyl. In some embodiments, $R^t$ is H.

In some embodiments, $NR^aR^b$ is a chelator group of Formula:

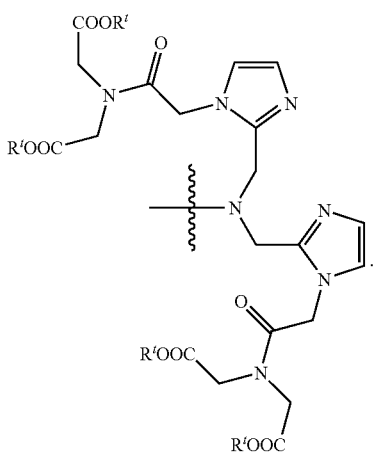

In some embodiments, $NR^aR^b$ is a chelator group of Formula:

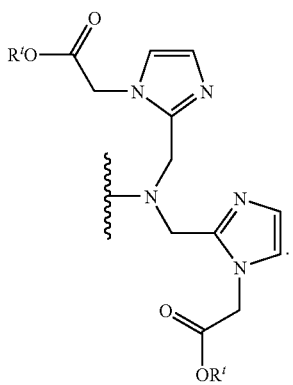

In some embodiments, NR$^a$R$^b$ is a chelator group of Formula:

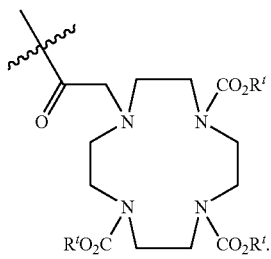

In another aspect, a complex is provided of the compound of Formula I, II, III, or IV, containing an NR$^a$R$^b$ chelator group, and a metal. In some embodiments, the metal is Re, Tc, Y, Lu, Ga, or In. In some embodiments, the metal is a radionuclide. In some embodiments, the metal is technetium-99m, or rhenium-186m and/or rhenium-188m.

In another aspect, a complex including the compound of Formula I, II, III, or IV, where the compound includes an NR$^a$R$^b$ chelator group of Formula:

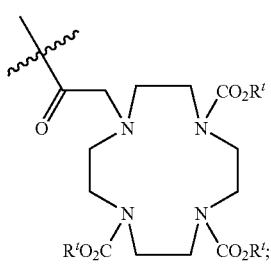

and a metal selected from the group consisting of Y, Ga, Lu, and In.

In another aspect, a complex includes a metal and the compound of Formula I, II, III, or IV, where the compound includes an NR$^a$R$^b$ chelator group of Formula:

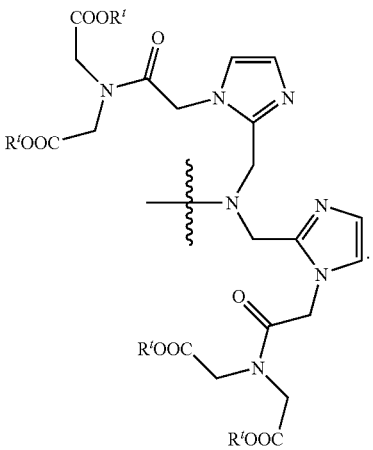

In another aspect, a complex includes a metal and the compound of Formula I, II, III, or IV, where the compound includes an NR$^a$R$^b$ chelator group of Formula:

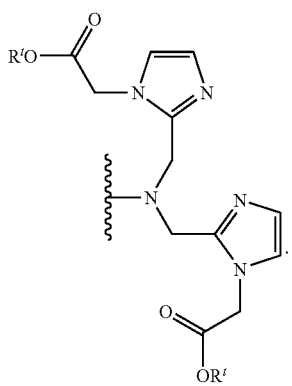

In another aspect, a complex is provided that is:

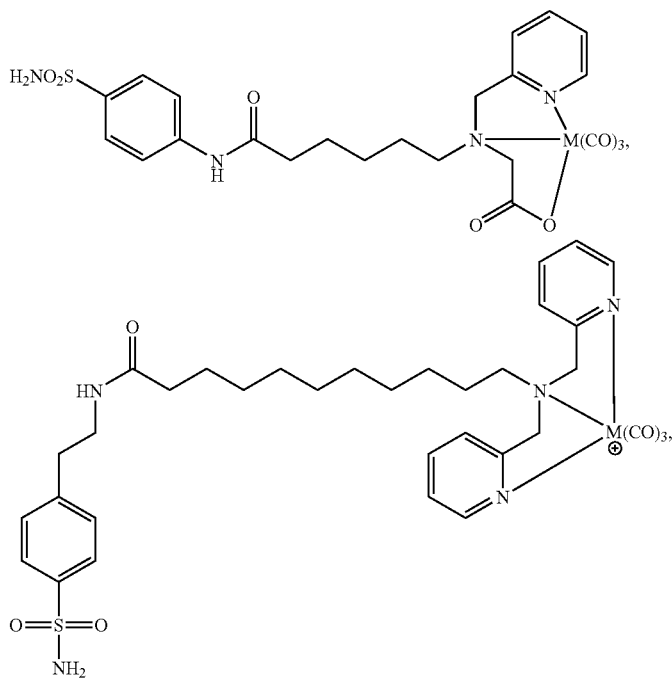

-continued
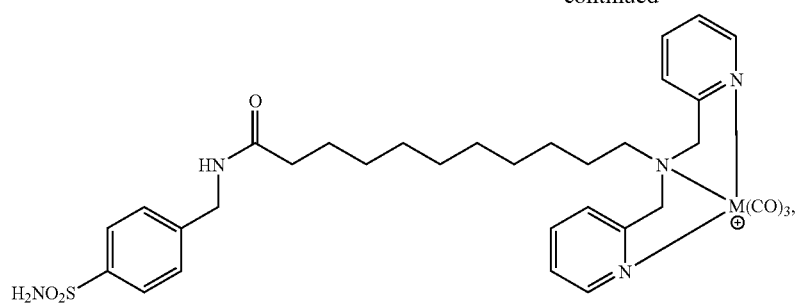
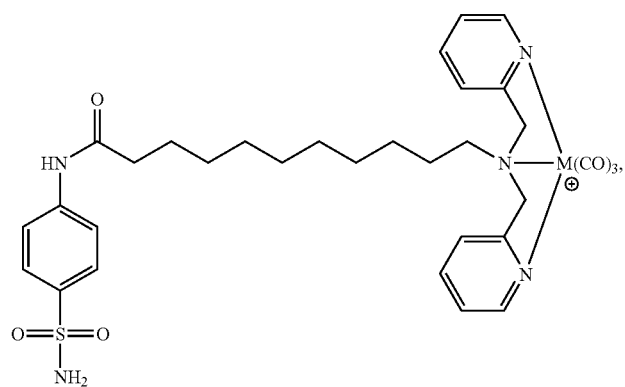
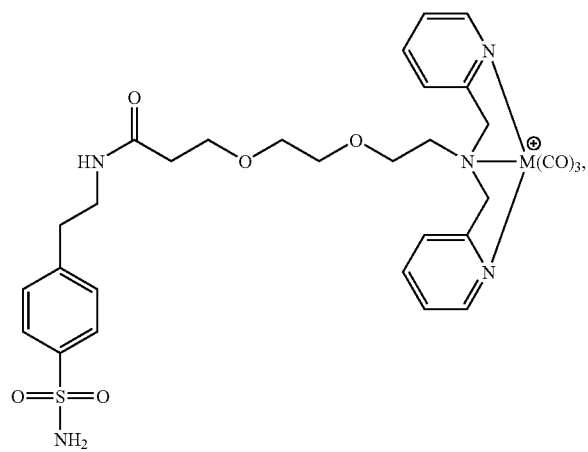
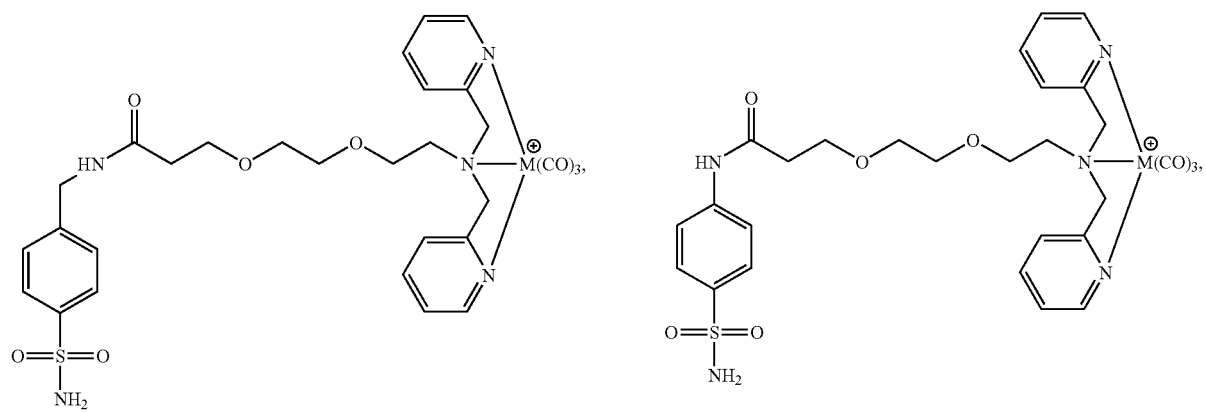

-continued

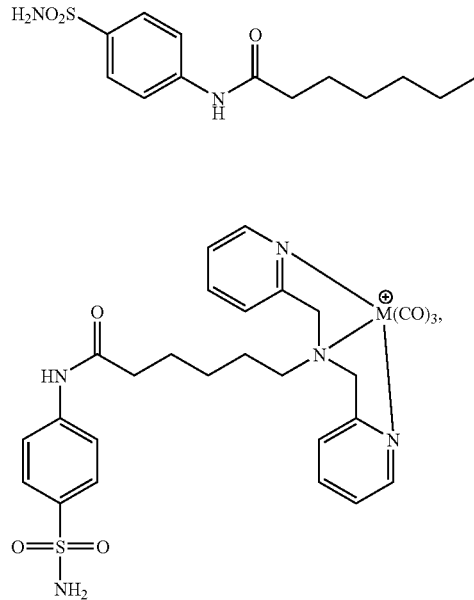
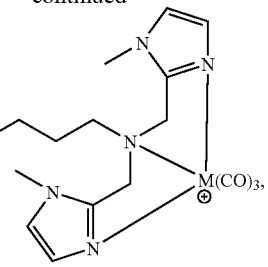
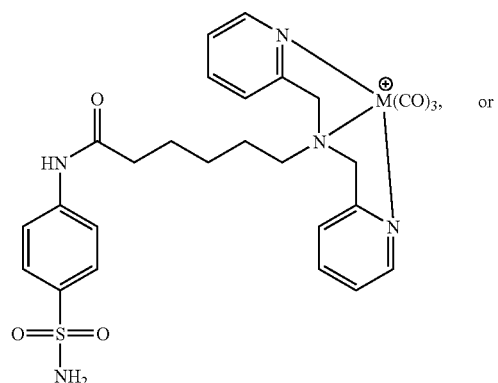

pharmaceutically acceptable salts and solvates thereof; where M is Tc or Re.

In another aspect, a pharmaceutical formulation is provided including a compound of any one of Formulas I, II, III, IV, a pharmaceutically acceptable salt or solvate thereof, and a pharmaceutically acceptable excipient, wherein the compound includes a radionuclide. In some embodiments, the radionuclide is iodine. In other embodiments, the radionuclide is a metal. In some embodiments, the metal is Re, Tc, Y, Lu, Ga, or In.

In another aspect, a method of imaging a region in a patient is provided, including the steps of: administering to a patient a diagnostically effective amount of a compound of any one of Formulas I, II, III, IV, a pharmaceutically acceptable salt or solvate thereof, and obtaining an image of the region of the patient, wherein the compound includes a radionuclide. In some embodiments, the radionuclide is iodine. In other embodiments, the radionuclide is a metal. In some embodiments, the metal is Re, Tc, Y, Lu, Ga, or In.

DETAILED DESCRIPTION

Figure 1:
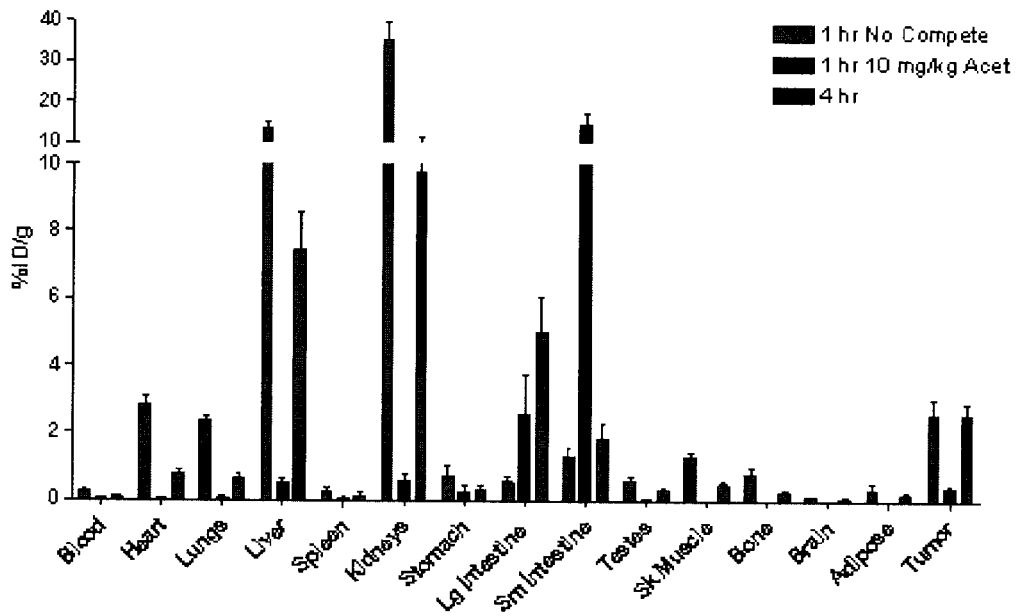
FIG. 1 is a graph of the tissue biodistribution in HeLa Xenograft mice of a $^{99m}$Tc analog of the compound of Example 8, expressed as % ID/g±(SEM).

There are two categories of radiopharmaceuticals: (i) those with biological distribution determined strictly by blood flow, or perfusion, and targeting high capacity systems such as glomerular filtration, phagocytosis, hepatocyte clearance and bone absorption and (ii) those with distribution determined by specific enzymatic or receptor binding interactions, which are low-capacity sites. The present radiopharmaceuticals belong to the second category and are synthesized by conjugating the radionuclide coordination complex to a biologically active molecule selective for a particular protein or receptor of interest.

While a variety of biologically active molecules (BAMs) can be used as the c have advantages over antibodies or proteins. For example, small molecules and small peptides exhibit enhanced diffusion, faster blood clearance, and lower background radiation. These carrier allow the facile synthesis of analogs in a high-throughput manner. Additionally, small peptides can be readily converted into peptide mimetics or small molecular analogs that have enhanced stability and improved affinity for the target enzyme or receptor.

Accordingly, in one aspect, the synthesis of compounds of Formula I, II, III, or IV, is provided. In some embodiments, the compound includes a radioactive element that may be exploited for use of the compound in radioimaging. In some embodiments, the radioactive element is one of the unstable isotopes of Re, Tc, In, Ga, Y, Lu, or I. The radioactive compound may also be used as radiopharmaceuticals for the treatment and imaging of cancer cells. Specifically, the compounds may be used to target carcinomas of the cervix, brain, kidney, ovary, breast, lung and the esophagus.

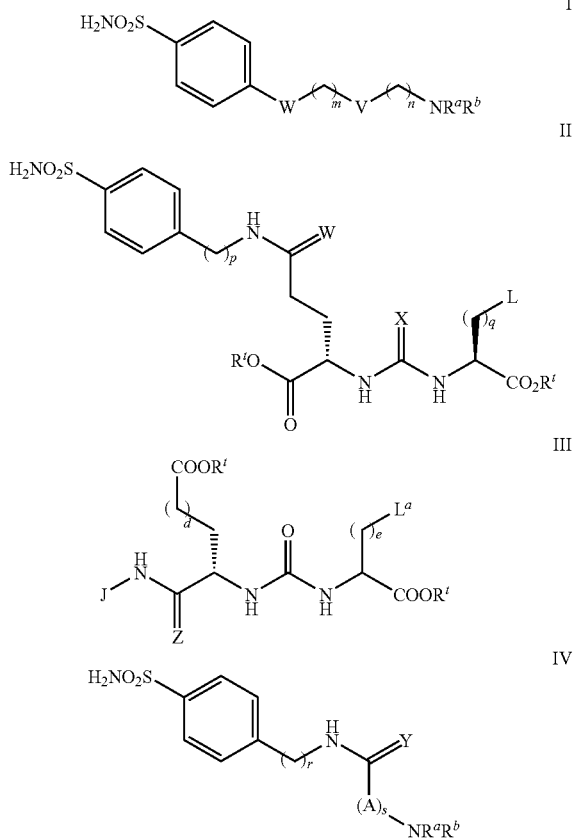

Definitions

For convenience, certain terms employed herein and within the appended claims are collected here.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The use of the terms "a" and "an" and "the" and similar referents in the context of describing the elements (especially in the context of the following claims) are to be construed to cover both the singular and the plural, unless otherwise indicated herein or clearly contradicted by context.

The terms "lipophilic group" and "lipophilic moiety" as used herein refer to a group, moiety or substituent that has a greater affinity for non-polar or non-aqueous environments versus polar or aqueous environments. For example, Merriam Webster's online dictionary defines "lipophilic" as "having an affinity for lipids (as fats)." Exemplary lipophilic moieties include aliphatic hydrocarbon radicals, e.g., alkyl radicals, aromatic hydrocarbon radicals, and long-chain acyl radicals; all of them have increasing lipophilicity as the number of constituent carbons increases. In general, addition of a lipophilic moiety to a particular compound will increase the compound's affinity for octanol in the standard octanol/water partition-coefficient-determination protocol; this protocol may be used to gauge a compound's relative hydrophobicity (lipophilicity) and hydrophilicity.

The terms "Lewis base" and "Lewis basic" refer to a chemical moiety capable of donating a pair of electrons under certain reaction conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. In certain examples, a Lewis base may consist of a single atom, such as oxide ($O_2^-$). In certain, less common circumstances, a Lewis base or ligand may be positively charged. A Lewis base, when coordinated to a metal ion, is often referred to as a ligand.

The term "ligand" refers to a species that interacts in some fashion with another species. In one example, a ligand may be a Lewis base that is capable of forming a coordinate bond with a Lewis Acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

The term "chelating agent" refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" are art-recognized and refer to chelating agents having, respectively, two, three, and four electron pairs readily available for simultaneous donation to a metal ion coordinated by the chelating agent. Usually, the electron pairs of a chelating agent forms coordinate bonds with a single metal ion; however, in certain examples, a chelating agent may form coordinate bonds with more than one metal ion, with a variety of binding modes being possible.

The term "coordination" refers to an interaction in which one multi-electron pair donor coordinatively bonds (is "coordinated") to one metal ion.

The term "complex" refers to a compound formed by the union of one or more electron-rich and electron-poor molecules or atoms capable of independent existence with one or more electronically poor molecules or atoms, each of which is also capable of independent existence.

The phrase "therapeutically-effective amount" as used herein means that amount of a compound, material, or composition comprising a compound which is effective for producing some desired therapeutic effect in at least a sub-population of cells in an animal at a reasonable benefit/risk ratio applicable to any medical treatment.

As used herein, the terms "treating" or "treatment" is intended to encompass also diagnosis, prophylaxis, therapy and cure. The patient receiving this treatment is any animal in need, including primates, in particular humans, and other mammals such as equines, cattle, swine and sheep; and poultry and pets in general.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "amino acid" refers to all compounds, whether natural or synthetic, which include both an amino functionality and an acid functionality, including amino acid analogs and derivatives.

The term "heteroatom" refers to an atom of any element other than carbon or hydrogen. Illustrative heteroatoms include boron, nitrogen, oxygen, phosphorus, sulfur and selenium.

In general, "substituted" refers to an alkyl or alkenyl group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

The term "aminoalkyl," refers to an alkyl group having the indicated number of carbon atoms wherein one or more of the alkyl group's hydrogen atoms is replaced with an —NR$^1$R$^2$ group, wherein R$^1$ and R$^2$ each independently refer to hydrogen, unsubstituted (C$_1$-C$_8$)alkyl, unsubstituted aryl and aryl substituted with one to three substituents selected from -halo, unsubstituted alkoxy, thiol and CN. When R$^1$ and R$^2$ are attached to the same nitrogen atom, they can be combined with the nitrogen atom to form a 5-, 6- or 7-membered ring. Non-limiting examplars of aminoalkyl groups include, but are not limited to, —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$CH$_2$CH$_2$CH$_2$NH$_2$, —CH$_2$CH$_2$CH$_2$CH$_2$CH$_2$CH$_2$NH$_2$, and branched versions thereof.

The term "alkylcarbonyl" denotes an —(C$_1$-C$_8$)alkyl-C(O) group in which one or more methylenes in the C$_1$-C$_8$ alkyl group is replaced with a C(O) group. Representative examples include, but are not limited to, acetyl, propionyl, and CH$_3$(CH$_2$)$_2$C(O)— group.

The terms "cyclic alkyl" or "cycloalkyl" refers to a saturated or partially saturated non-aromatic cyclic alkyl groups of from 3 to 14 carbon atoms and no ring heteroatoms and having a single ring or multiple rings including fused and bridged ring systems. Cycloalkyl groups may be substituted or unsubstituted. Cycloalkyl or cyclic alkyl groups include mono-, bi- or tricyclic alkyl groups having from 3 to 14 carbon atoms in the ring(s), or, in some embodiments, 3 to 12, 3 to 10, 3 to 8, or 3 to 4, 5, 6 or 7 carbon atoms. Exemplary monocyclic cycloalkyl groups include, but not limited to, cyclopropyl, cyclobutyl, cyclopentyl, cyclohexyl, cycloheptyl, and cyclooctyl groups. Bi- and tricyclic ring systems include both bridged cycloalkyl groups and fused rings, such as, but not limited to, bicyclo[2.1.1]hexane, adamantyl, decalinyl, and the like.

Alkenyl groups include straight and branched chain and cycloalkyl groups as defined above, except that at least one double bond exists between two carbon atoms. Thus, alkenyl groups have from 2 to about 12 carbon atoms in some embodiments, from 2 to 10 carbon atoms in other embodiments, and from 2 to 8 carbon atoms in other embodiments. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl, among others. Alkenyl groups may be substituted or unsubstituted. Representative substituted alkenyl groups may be mono-substituted or substituted more than once, such as, but not limited to, mono-, di- or tri-substituted with substituents such as those listed above.

Alkynyl groups include straight and branched chain and cycloalkyl groups as defined above, except that at least one triple bond exists between two carbon atoms. Examples of a (C$_2$-C$_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Aryl group includes both substituted and unsubstituted aryl groups. Substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms.

Heterocyclyl groups includes non-aromatic ring compounds containing 3 or more ring members, of which one or more is a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. Heterocyclyl groups may be substituted or unsubstituted. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydropyranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Heterocyclyl groups may be substituted or unsubstituted. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Alkoxy groups may be substituted or unsubstituted. Representative substituted alkoxy groups may be substituted one or more times with substituents such as those listed above.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, monoalkylamino, dialkylamino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" refers to an aromatic or non-aromatic ring in which each atom of the ring is carbon.

The term "nitro" refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "*Advanced Inorganic Chemistry*" by Cotton and Wilkinson.

The term "amine or amino" refers to an —NR$^c$R$^d$ group wherein R$^c$ and R$^d$ each independently refer to a hydrogen, (C$_1$-C$_8$)alkyl, aryl, heteroaryl, and heterocycloalkyl group. When R$^c$ and R$^d$ are attached to the same nitrogen atom, they can be combined with the nitrogen atom to form a 5-, 6- or 7-membered ring. For example, —NR$^c$R$^d$ is meant to include 1-pyrrolidinyl, pyridinyl or a 4-morpholinyl ring.

The term "amido" is art recognized as an amino-substituted carbonyl and includes a moiety that may be represented by the general formula, —C(O)NR$^c$R$^d$ group wherein R$^c$ and R$^d$ are as defined above. According to some embodiments, the amide does not include imides which may be unstable.

The terms "carboxyl" and "carboxylate" are include such moieties as may be represented by the general formulas:

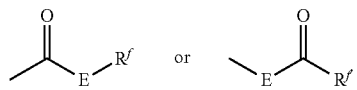

wherein E is a bond or represents O or S, and R$^f$ and R$^{f'}$ individually is H, alkyl, alkenyl, aryl, or a pharmaceutically acceptable salt. Where E is O, and R$^f$ is as defined above, the moiety is referred to herein as a carboxyl group, and particularly when R$^f$ is a hydrogen, the formula represents a "carboxylic acid". In general, where the expressly shown oxygen is replaced by sulfur, the formula represents a "thiocarbonyl" group.

The terms "alkoxyl" or "alkoxy" refer to an alkyl group, as defined above, having an oxygen radical attached thereto. Representative alkoxyl groups include methoxy, ethoxy, propoxy, butyoxy, tert-butoxy and the like. An "ether" is two hydrocarbons covalently linked by an oxygen. "Ether" also encompasses polyethers where more than one ether group, or linkage, may be present in a given group. "Ether" also encompasses cyclic ethers, and crown ethers, where the ether linkage is within a cyclic group.

The term "sulfonate" refers to a moiety that may be represented by the general formula, —S(O)$_2$OR$^g$, in which R$^g$ is an electron pair, hydrogen, alkyl, cycloalkyl, or aryl. The term "sulfate" includes a moiety that may be represented by the general formula, —OS(O)$_2$OR$^g$, in which R$^g$ is as defined above. The term "sulfonamido" includes a moiety that may be represented by the general formula: —N(R$^f$)S(O)$_2$OR$^{f'}$, in which R$^f$ and R$^{f'}$ are as defined above. The term "sulfamide" refers to a moiety that may be represented by the general formula, —S(O)$_2$NR$^e$R$^f$, in which in which R$^f$ and R$^{f'}$ are hydrogen, (C$_1$-C$_8$)alkyl or aryl. The term "sulfonyl" refers to a moiety that may be represented by the general formula: —S(O)$_2$R$^h$, in which R$^h$ is one of the following: hydrogen, alkyl, alkenyl, alkynyl, cycloalkyl, heterocyclyl, aryl or heteroaryl.

The definition of each expression, e.g. alkyl, m, n, and the like, when it occurs more than once in any structure, is intended to be independent of its definition elsewhere in the same structure.

The terms triflyl, tosyl, mesyl, and nonaflyl refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain the groups, respectively. The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

Certain compounds contained in the compositions may exist in particular geometric or stereoisomeric forms. In addition, compounds may also be optically active. The compounds may also include cis- and trans-isomers, R- and S-enantiomers, diastereomers, (D)-isomers, (L)-isomers, the racemic mixtures thereof, and other mixtures thereof. Additional asymmetric carbon atoms may be present in a substituent such as an alkyl group. If, for instance, a particular enantiomer of compound is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis,* 3$^{rd}$ ed.; Wiley: New York, 1999).

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given that structure, then the depicted structure controls. Additionally, if the stereochemistry of a structure or a portion of a structure is not indicated with, for example, bold or dashed lines, the structure or portion of the structure is to be interpreted as encompassing all stereoisomers of it.

Chelator Compounds and their Synthesis

In one aspect, a compound of Formula I, its pharmaceutically acceptable salts and solvates are provided:

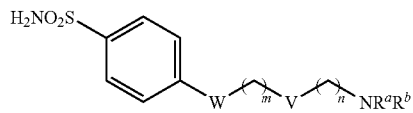

I

According to some embodiments of Formula I, W is a bond, $(C_1-C_8)$alkyl, $(C_2-C_8)$alkenyl, aryl, heteroaryl, —NHC(O), urea (—NH—C(O)—NH—), or thiourea (—NH—C(S)—NH—); V is a bond, $(C_1-C_8)$alkyl, $(C_2-C_8)$alkenyl, aryl, heteroaryl, urea (—NH—C(O)—NH—), or thiourea (—NH—C(S)—NH—); m is an integer from 0 to 15, and n is an integer from 0 to 15. In some embodiments, W and V are both not urea or thiourea.

The $NR^aR^b$ group of Formula I is one of the following chelator groups, where $R^t$ is H, a $C_1-C_8$ alkyl group, an ammonium ion, or an alkali or alkaline earth metal ion; and $R^v$ is alkyl:

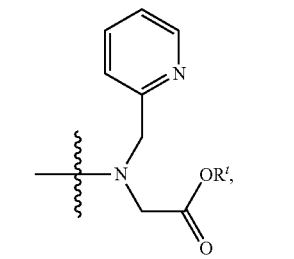
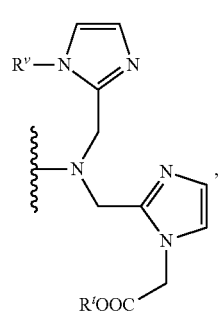
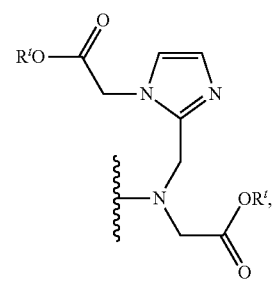
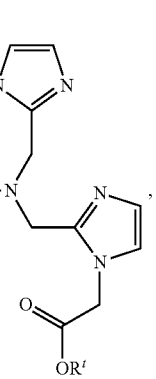
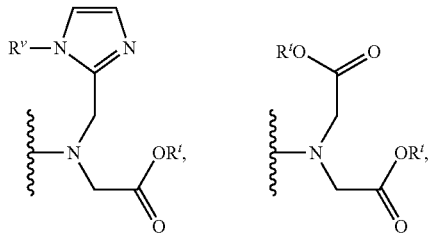
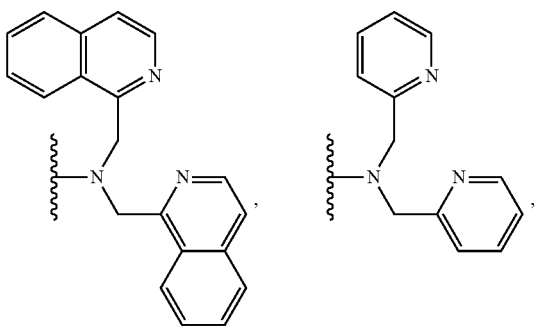
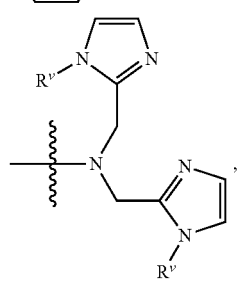
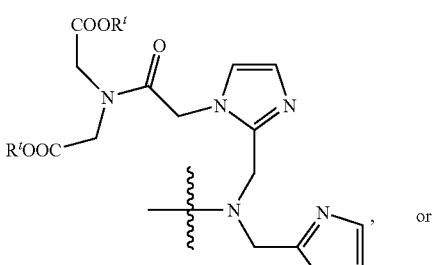
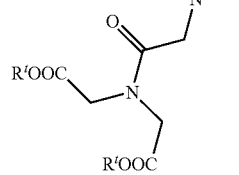
, or
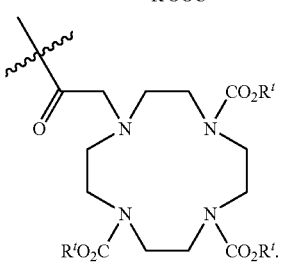

According to some embodiments, $R^v$ is methyl, ethyl, n-propyl, iso-propyl, n-butyl, iso-butyl, or tert-butyl. In other embodiments, $R^v$ is methyl. In some embodiments, each $R^t$ is independently H or tert-butyl. In yet other embodiments, $R^t$ is H.

According to some embodiments, the NR$^a$R$^b$ group of the compound of Formula I is:

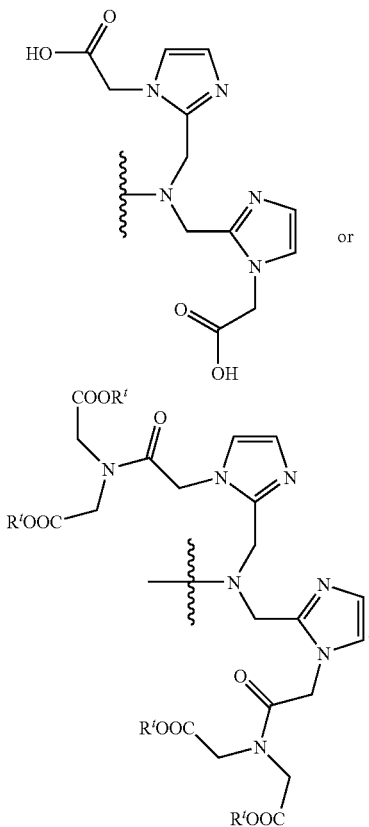

or

In embodiments where NR$^a$R$^b$ is bis(methylene)bis(1H-imidazole-2,1-diyl))diacetic acid, the compound of Formula I is not 2,2'-(2,2'-(8-(3-(4-sulfamoylphenyl)thioureido) octylazanediyl)-bis(methylene)bis(1H-imidazole-2,1-diyl))diacetic acid; 2,2'-(2,2'-(4-sulfamoylphenylazanediyl)-bis(1H-imidazole-2,1-diyl))diacetic acid; or 2,2'-(2,2'-(5-(4-sulfamoylbenzamido)pentylazanediyl)-bis(methylene)bis(1H-imidazole-2,1-diyl))diacetic acid.

According to various embodiments, the NR$^a$R$^b$ group of the compound may further be chelated to a metal. In some embodiments, the metal is a radioactive nuclide. For example, the metal may be technetium-99m, or rhenium-186 m/188m. Complexes such as [NEt$_4$]$_2$[MBr$_3$(CO)$_3$]; M is Tc or Re, may be reacted with the compounds of formula I in an alcoholic solvent to provide for the chelated compounds of formula I-M, as further described below.

I-M

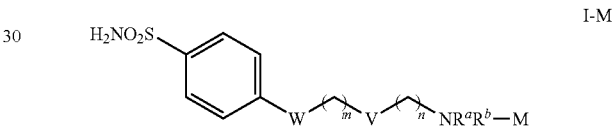

Illustrative compounds according to Formula I-M, include, but are not limited to any one of the following:

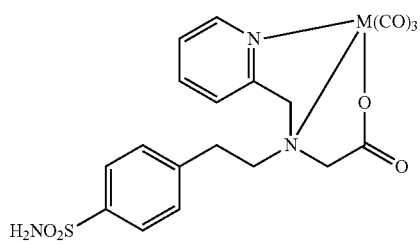

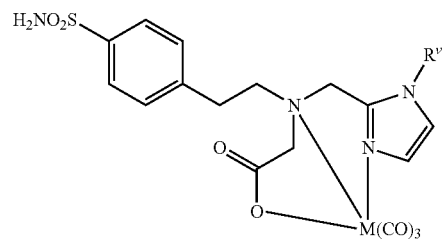

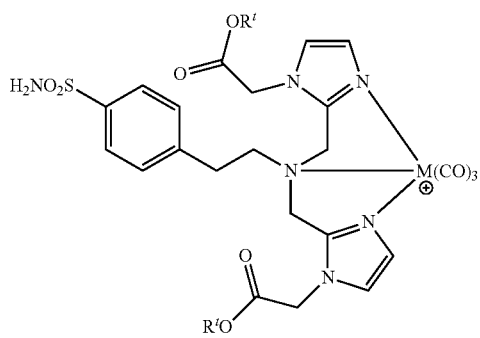

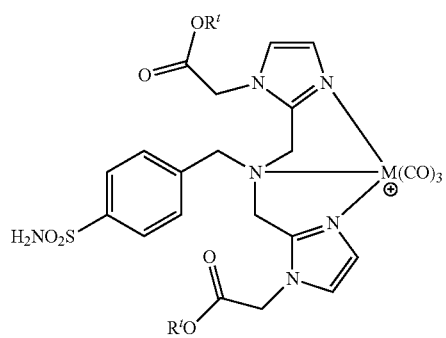

29 30
-continued
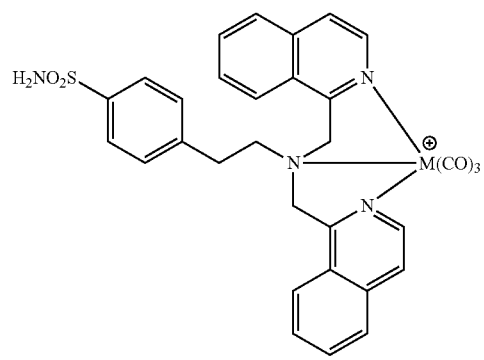
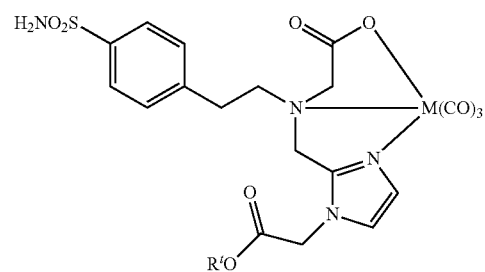
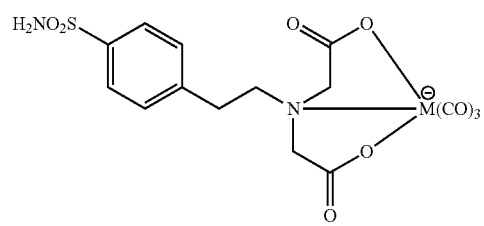
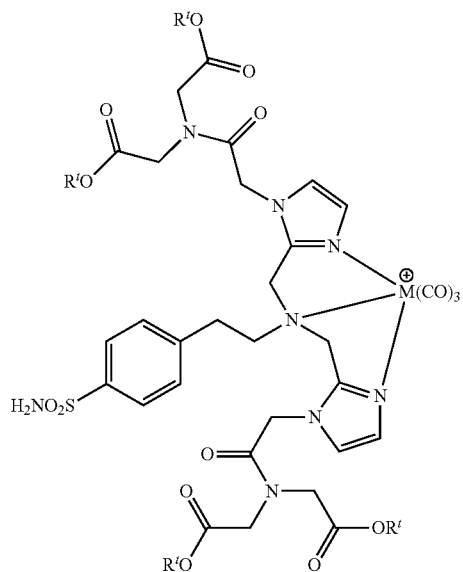
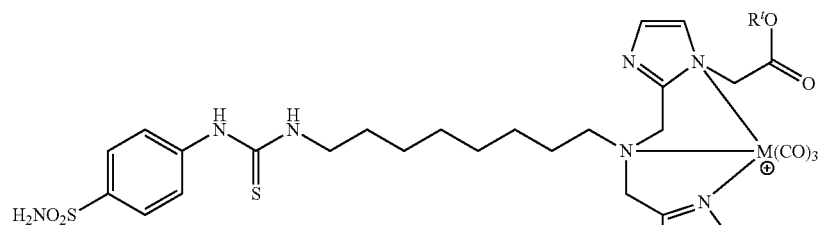
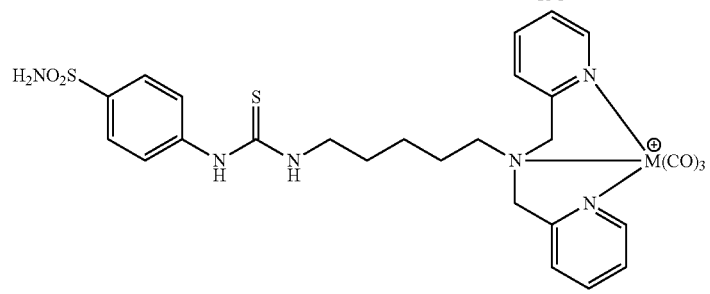

-continued
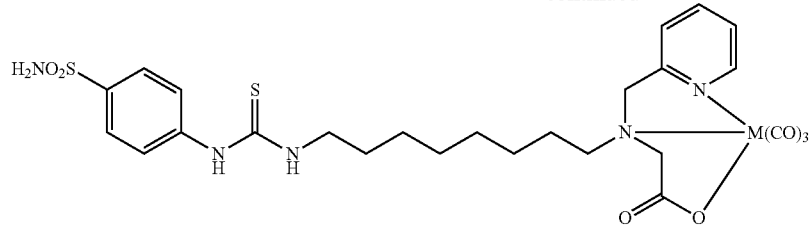
with the proviso that the complex of Formula I-M is not
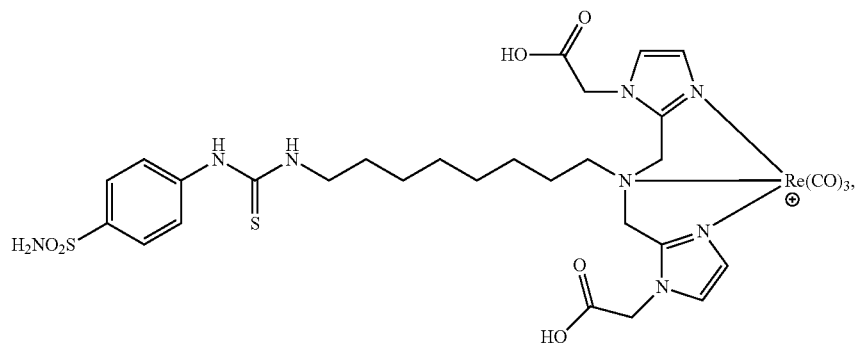
[Re(CO)3][2,2'-(2,2'-(8-(3-(4-sulfamoylphenyl)thioureido)octylazanediyl)bis(methylene)bis(1H-imidazole-2,1-diyl)diacetic acid]
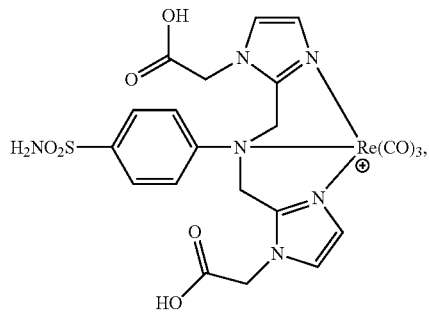
[Re(CO)3[2-(2-((((1H-imidazol-2-yl)methyl)(4-sulfamoylphenyl)amino)methyl)-1H-imidazol-1-yl)acetic acid]
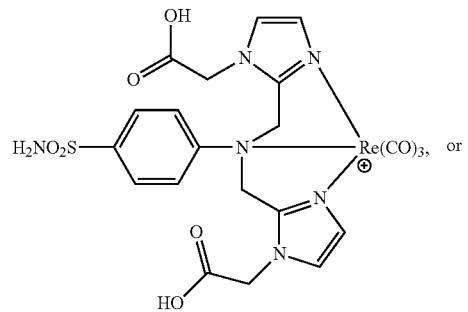
[Tc(CO)3[2-(2-((((1H-imidazol-2-yl)methyl)(4-sulfamoylphenyl)amino)methyl)-1H-imidazol-1-yl)acetic acid]

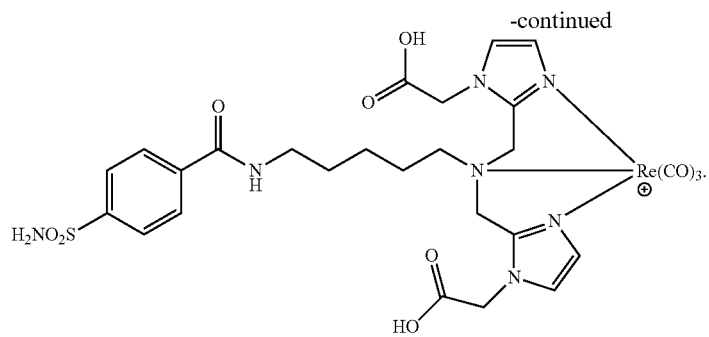

[Re(CO)3][2,2'-(2,2'-(8-(3-(4-sulfamoylphenyl)thioureido)octylazanediyl)-bis(methylene)bis(1H-imidazole-2,1-diyl)diacetic acid]

In some embodiments, pharmaceutically acceptable salts, solvates, stereoisomers, tautomers, and prodrugs of such compounds are also provided. In another embodiment, a pharmaceutical composition includes a compound of Formula I-M and a pharmaceutically acceptable excipient.

In another aspect, a compound of Formula II is provided, as well as its pharmaceutically acceptable salts and solvates.

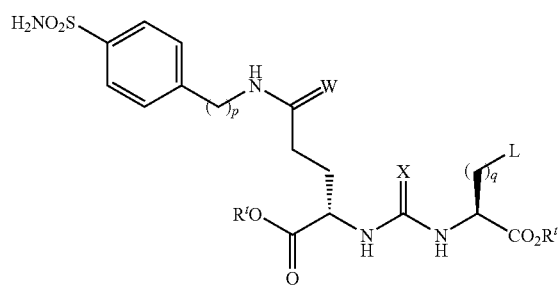

In Formula II, L is an NR$^a$R$^b$ group as defined as above for Formula I, or an group of formula

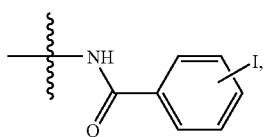

where the iodine may be in the ortho, meta, or para position to the carboxamide group; W and X are independently oxygen or sulfur; each R$^t$ is independently H, a C$_1$-C$_8$ alkyl group, an ammonium ion, or an alkali or alkaline earth metal ion; p is an integer form 0 to 5; and q is an integer from 0 to 8. In some embodiments, each is independently H or tert-butyl. In yet other embodiments, R$^t$ is H. In some embodiments, W and X are both oxygen. In some embodiments, where L is a group of formula

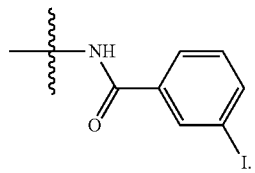

the iodine is a radioactive isotope of iodine, for example, I-123 or I-131. In some embodiments, L is a group of formula According to some embodiments of the compound of Formula II, in which L is 3-iodobenzamide, the iodine is a radioactive isotope such as 1-123 or 1-131, and may be used in therapeutic preparations for the treatment of cancer. According to another aspect, a pharmaceutical composition is also provided, which includes the 3-iodobenzamide analog of the compound of Formula II, and a pharmaceutically acceptable excipient for the treatment of cancer.

According to various embodiments, the compounds may further be chelated to a metal to provide a complex. In some embodiments, the metal is a radioactive nuclide. For example, the metal may be technetium-99m, or rhenium-186/188. Complexes such as [NEt$_4$]$_2$[MBr$_3$(CO)$_3$]; M is Tc or Re, may be reacted with the compounds of formula II in an alcoholic solvent to provide for the chelated compounds of formula II-M, as further described below.

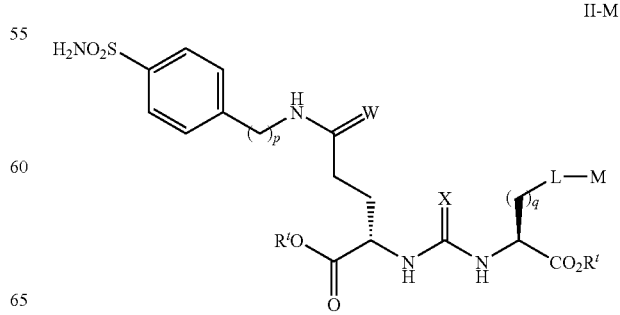

Illustrative of the compounds of Formulas II and II-M, include, but are not limited to any one of the following:
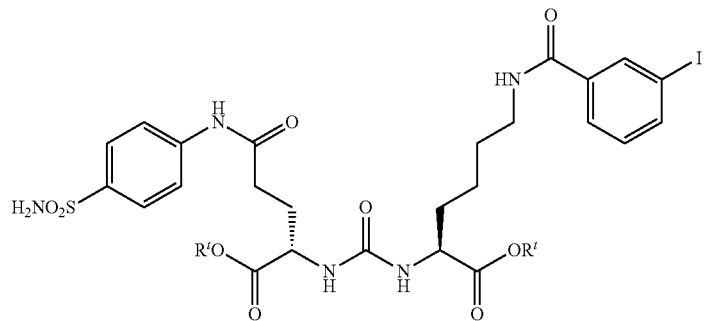
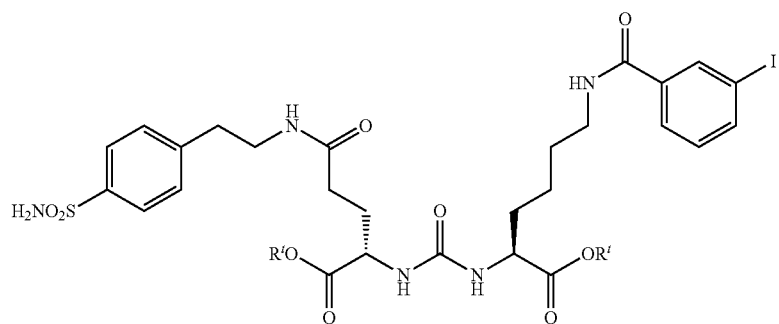
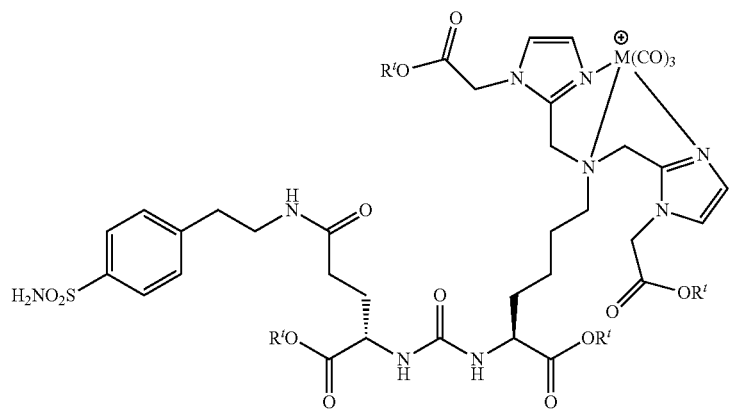

In some embodiments, pharmaceutically acceptable salts, solvates, stereoisomers, tautomers, and prodrugs of the compound of Formula II-M is provided. In another embodiment, a pharmaceutical composition includes a compound of Formula II-M and a pharmaceutically acceptable excipient.

In another aspect, a compound of Formula III, its pharmaceutically acceptable salts or solvates, is provided:

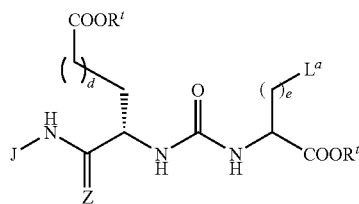

III

According to Formula III, $R^t$ is as defined above; d is an integer from 0 to 5, e is an integer from 0 to 8; J is an optionally substituted aryl group; and $L^a$ is an $NR^aR^b$ group as defined as above for Formula I, or an group of formula

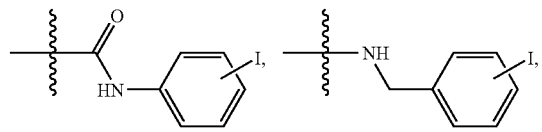

-continued

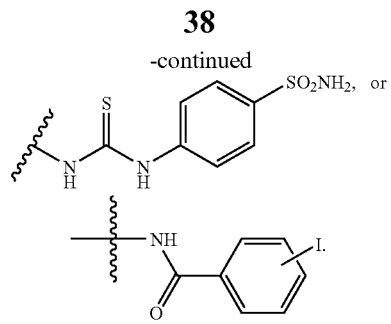

According to some embodiments, J is phenyl, naphthyl, or anthracene. In one embodiment, J is phenyl which is mono-substituted or disubstituted. For example, the phenyl may be substituted with I, $(C_1-C_8)$alkyl, $(C_2-C_8)$alkenyl, —CN, —$NO_2$, —OH, —SH, —$SO_2NH_2$, or —$NR^cR^d$, where $R^c$ and $R^d$ are independently H, $(C_1-C_4)$alkyl, or aryl. Where J is di-substituted, the additional substituent, R", is $(C_1-C_8)$alkyl, $(C_2-C_8)$alkenyl, —OH, —SH, or halogen. Moreover, the additional substituent group can be either ortho, meta, or para in relation to the first substituent group. Additionally, one or more of the substituents can be modified by the addition of one or more other groups.

Illustrative examples of the compound of Formula III, include, but are not limited to:

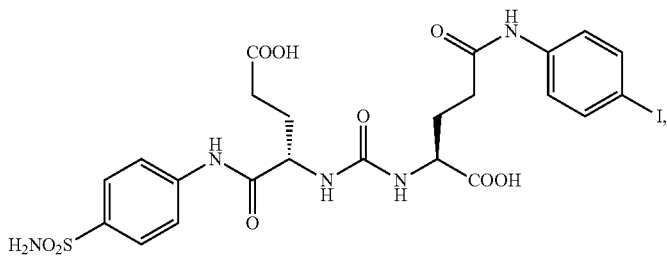

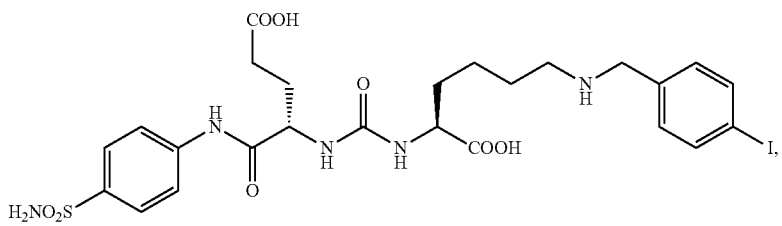

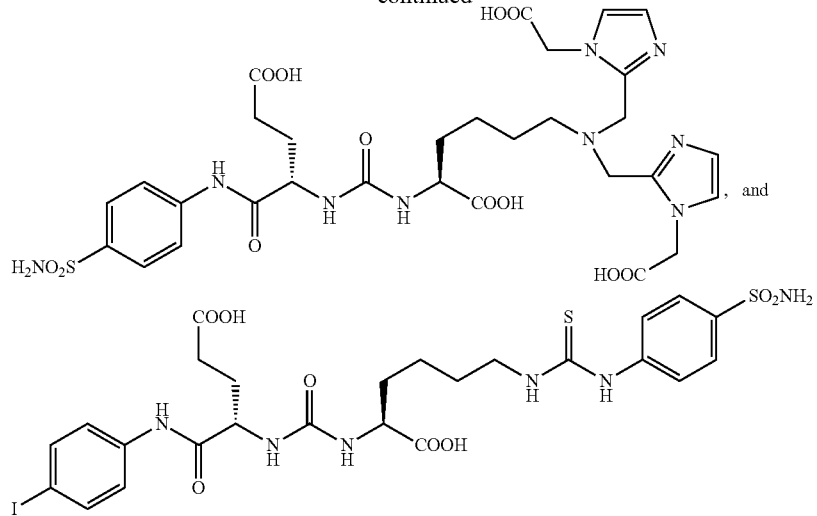

According to various embodiments, the compounds of Formula III may further be chelated to a metal, where $L^a$ is an $NR^aR^b$ chelator group, as defined above. In some embodiments, the metal is a radioactive nuclide. For example, the metal may be technetium-99m, or rhenium-186/188. Complexes such as $[NEt_4]_2[MBr_3(CO)_3]$; M is Tc or Re, may be reacted with the compounds of formula III in an alcoholic solvent to provide for the chelated compounds of formula III-M, as further described below.

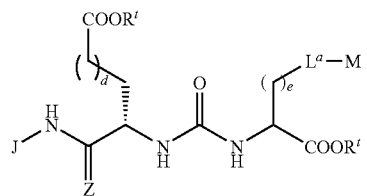

Illustrative chelated compounds of Formula III-M, include, but are not limited to:

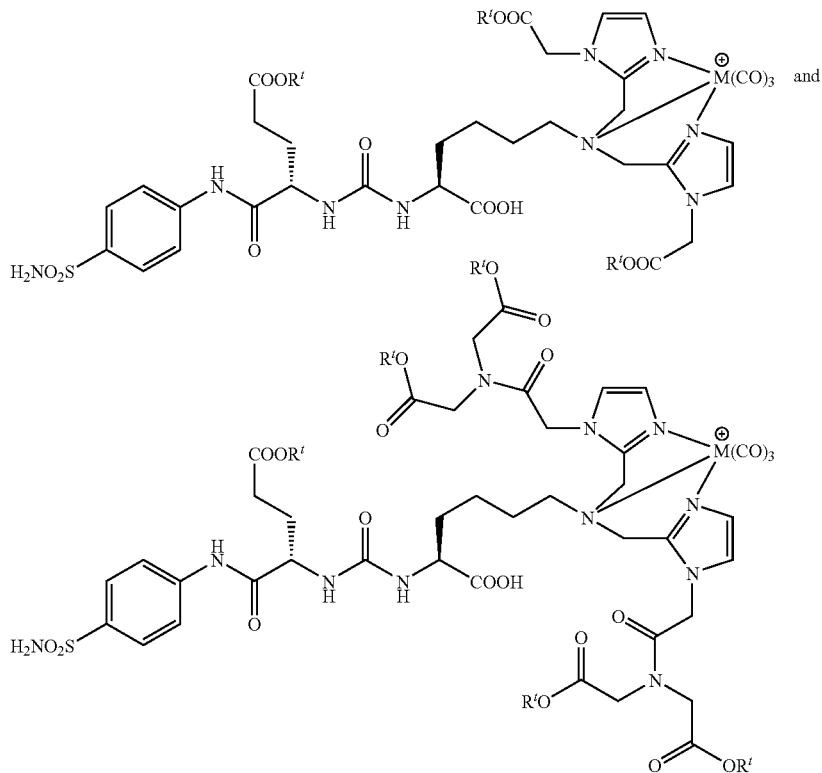

In another aspect, a compound of Formula IV is provided:

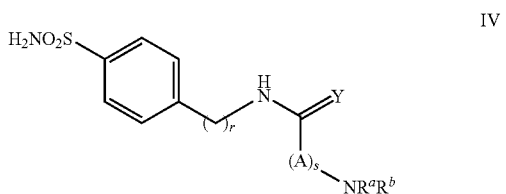

IV where, $NR^aR^b$ is as defined above for the compound of Formula I; Y is O or S; A is $(C_1$-$C_8)$alkyl, —$(CH_2)_x(OCH_2CH_2)_y$— or —$(OCH_2CH_2)_y(CH_2)_x$—; x and y are individually an integer from 0 to 3; r is an integer from 0 to 5; and s is an integer from 0 to 5.

According to various embodiments, the $NR^aR^b$ group of the compound may further be chelated to a metal. In some embodiments, the metal is a radioactive nuclide. For example, the metal may be technetium-99m, or rhenium-186 m/188m. Complexes such as $[NEt_4]_2[MBr_3(CO)_3]$; M is Tc or Re, may be reacted with the compounds of formula IV in an alcoholic solvent to provide for the chelated compounds of formula IV-M, as further described below.

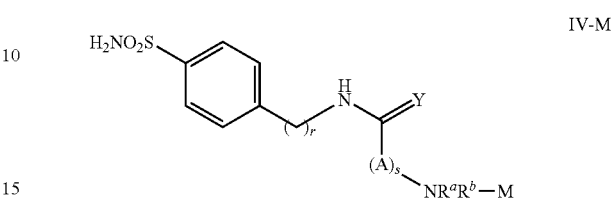

IV-M

Illustrative compounds according to Formula IV-M, include, but are not limited

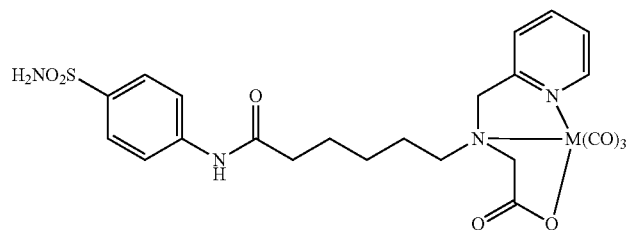

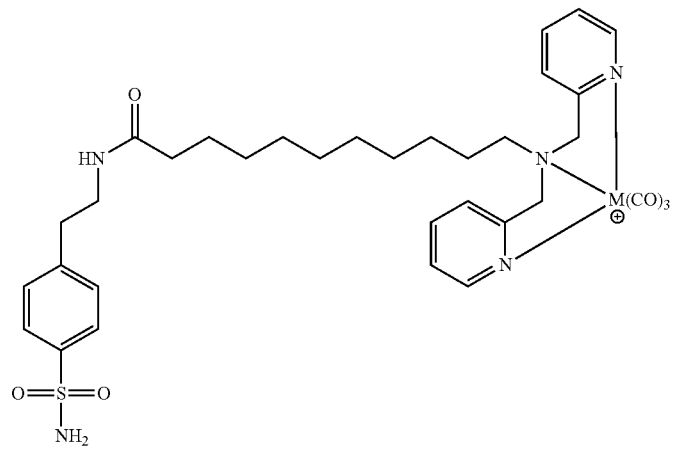

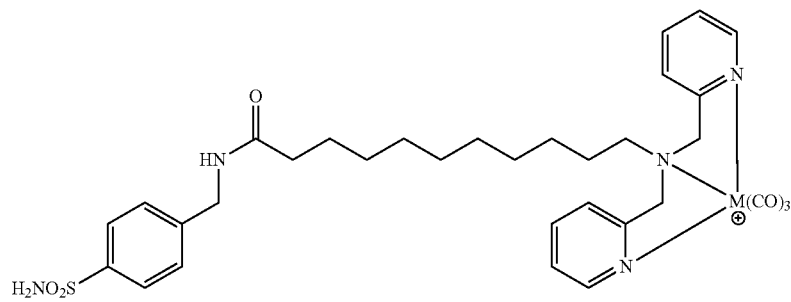

-continued
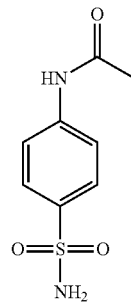
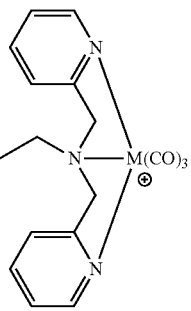
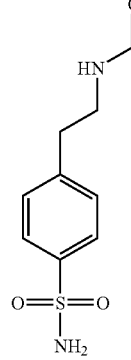
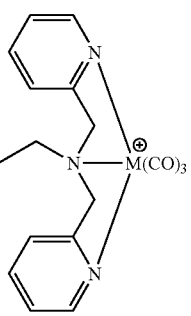
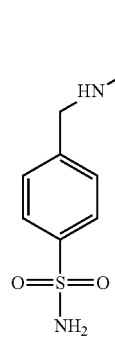
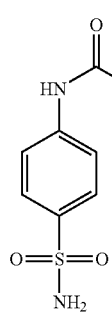
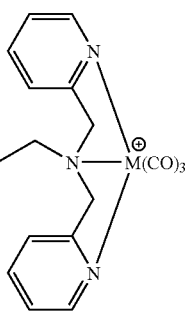
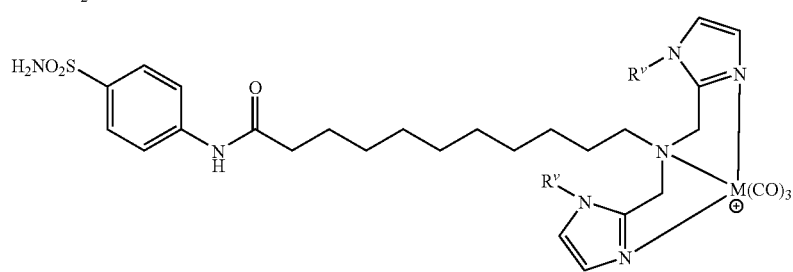

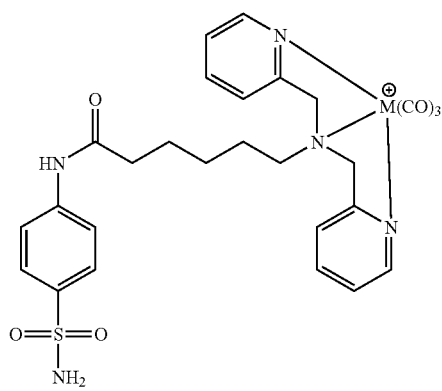

Pharmaceutical Formulations

The compounds of Formulas I-M, II-M, III-M, and IV-M may contain one or more a radionuclides which are suitable for use as radio-imaging agents and as therapeutics for the treatment of rapidly proliferating cells. Accordingly, in one embodiment, a pharmaceutical composition is provided including a compound of Formula I-M, II-M, or IV-M a salt, solvate, stereoisomer, or tautomer thereof, and a pharmaceutically acceptable carrier.

In general, the compounds Formula I-M, II-M, III-M, or IV-M, or pharmaceutical compositions thereof, may be administered orally, or via a parenteral route, usually by injection. Parenteral routes include, but are not limited to, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. In some embodiments, the compound, or pharmaceutical composition thereof, is administered orally. Such compositions may take the form of tablets, pills, capsules, semisolids, powders, solutions, suspensions, elixirs, aerosols, or any other appropriate compositions.

According to another aspect, a pharmaceutical composition is provided, which is suitable for in vivo imaging. Such suitable imaging pharmaceutical compositions contain an imaging agent that has a radionuclide either as an element, i.e. radioactive iodine, or a radioactive metal chelate, according the compounds of Formula I, II, III, or IV, in an amount sufficient for imaging, together with a pharmaceutically acceptable radiological vehicle. The radiological vehicle should be suitable for injection or aspiration, such as human serum albumin; aqueous buffer solutions, e.g., tris(hydromethyl)aminomethane (and its salts), phosphate, citrate, bicarbonate, etc; sterile water; physiological saline; and balanced ionic solutions containing chloride and or dicarbonate salts or normal blood plasma cations such as calcium, potassium, sodium, and magnesium.

The concentration of the imaging agent in the radiological vehicle should be sufficient to provide satisfactory imaging. For example, when using an aqueous solution, the dosage is about 1.0 to 50 millicuries. The imaging agent should be administered so as to remain in the patient for about 1 to 3 hours, although both longer and shorter time periods are acceptable. Therefore, convenient ampoules containing 1 to 10 mL of aqueous solution may be prepared.

Imaging may be carried out in the normal manner, for example by injecting a sufficient amount of the imaging composition to provide adequate imaging and then scanning with a suitable machine, such as a gamma camera. In certain embodiments, a method of imaging a region in a patient includes the steps of: administering to a patient a diagnostically effective amount of a compound complexed with a radionuclide; exposing a region of the patient to radiation; and obtaining an image of the region of the patient. In certain embodiments of the region imaged is the head or thorax.

The present invention, thus generally described, will be understood more readily by reference to the following examples, which are provided by way of illustration and are not intended to be limiting of the present invention.

EXAMPLES

General Synthetic Methods

General procedure for the alkylation of imidazole-2-carboxaldehyde. To a solution of imidazole-2-carboxaldehyde dissolved in DMF (1 mL) was added 1 molar equivalent of the alkylbromide, excess potassium carbonate and a catalytic amount of potassium iodide. The reaction was heated at 110° C. for 18 h followed by evaporation to dryness and purified utilizing a Biotage SP4 with a gradient method of 5-50% methanol in DCM.

General procedure for the formation of homogeneous chelators via reductive aminations. In a typical procedure a solution of the desired amine dissolved in DCE (2 mL) was added to 2.1 equivalence of the aldehyde. The reaction was heated at 50° C. for one hour followed by the addition of sodium triacetoxyborohydride (36 mg, 0.19 mmol). After stirring at room temperature for 12 h the solution was evaporated to dryness and purified utilizing a Biotage SP4; Gradient 5-50% methanol in DCM. The purified compound (24 mg, 0.034 mmol) was deprotected by treatment with piperidine/DMF 1:1 (1 mL), at room temperature for 2 h, followed by evaporation to dryness. The residue is dissolved in DCM and extracted with water. The aqueous layer is back extracted with excess DCM. Evaporation of the organic layer afforded the desired compounds as off-white solids.

General synthesis of benzenesulfonamide analogs with an amide bond. To a solution of the carboxylic acid (1 eqv) in DMF was added TEA (2 eqv) followed by the addition of 2-(1-H-7-azabenzotriazol-1-yl)-1,1,3,3-tetramethyl uronium hexafluorophosphate methanaminium (HATU, 1.4 eqv), and the appropriately substituted sulfonamide (1 eq). The reaction was stirred at 40° C. overnight. Concentration followed by purification utilizing a Biotage SP4 with a gradient method of 5-50% methanol in DCM afforded the desired free ligands.

General procedure for complexation of the compounds with a metal. As exemplified herein, rhenium is used as the metal in consideration of the availability of non-radioactive isotopes and the safety of workers. However, as is to be understood, similar synthetic procedures may be followed using the technetium analogs, as technetium and rhenium have similar reaction chemistry and are of a similar size due to the lanthanide contraction. Therefore, where Re may be specifically shown, it is understood to include Tc complexes as well.

Unless otherwise noted the synthesis of the Re(I) complexes was accomplished by reacting $[NEt_4]_2[ReBr_3(CO)_3]$ (or, $[^{99m}Tc(CO)_3(H_2O)_3]^+$) with the appropriate ligand ($10^{-6}M$–$10^{-4}M$) in the ratio of 1:1.2 in 10 ml of methanol. The sealed vial was heated at was allowed to heat at 100° C. for 4 hours. Upon cooling the reaction was analyzed for purity via RP-HPLC (reverse phase-HPLC) and the product was purified using a silica column using methanol as the eluent. The radiochemical purity (RCP) after HPLC purification, resulting in "carrier free" products, was determined via HPLC and shown to be consistently ≧95%. Although initial results demonstrated radiolabeling at concentrations as low as $10^{-6}$ M RCY was ≧80%. RCY is an abbreviation for radiochemical yield. To achieve a RCY>95% at 75° C., the reaction concentration needed to be increased to $10^{-4}$ M. In many cases, the corresponding Tc complexes are prepared and tested as the Re complexes in order to prepare non-radioactive analogs for testing and handling purposes.

Synthesis of Exemplary Formula I Compounds

Scheme 1 is an illustration of the general synthetic route for 4-aminoethyl benzenesulfonamide analogs. Reductive amination of the imine formed by reacting 4-aminoethylbenzenesulfonamide with an appropriate aldehyde followed by the reaction of a tridentate ligand with a radionuclide provided compounds that comport with Formula I.

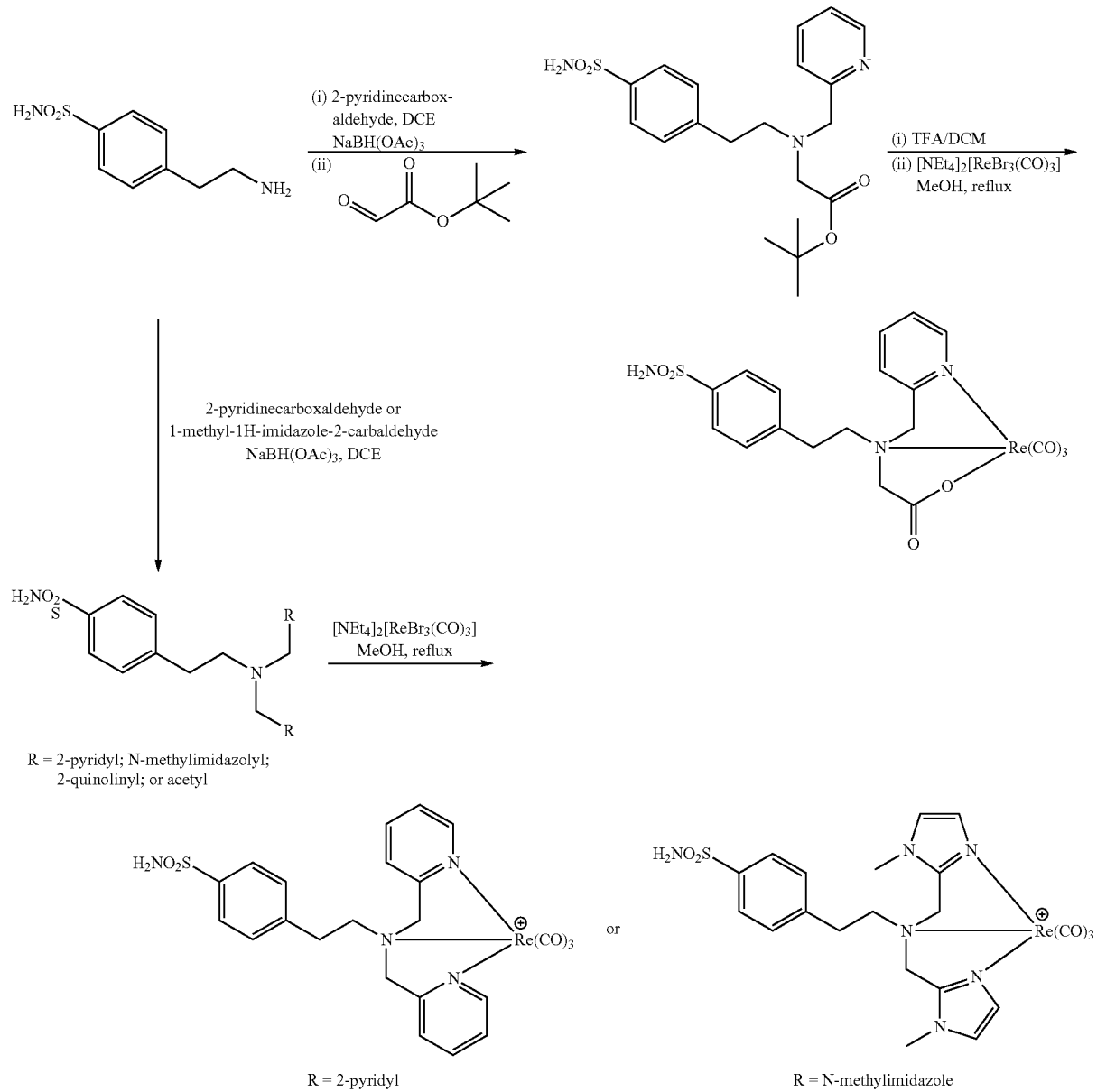

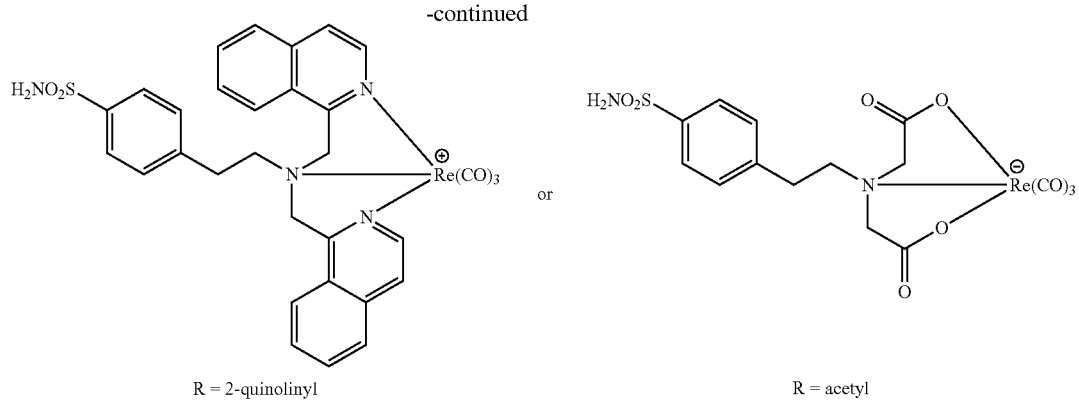
R = 2-quinolinyl
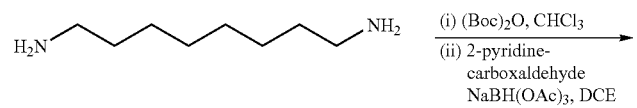
R = acetyl
Scheme 2 illustrates the general synthetic route for thiourea benzenesulfonamide analogs. Reaction of the N,N-bis(pyridine-2-ylmethyl)alkyl-1,6-diamine with a 4-isothiocyanato benzenesulfonamide followed by reaction with a radionuclide gave the corresponding thiourea analogs that also comport with Formula I.
Scheme 2
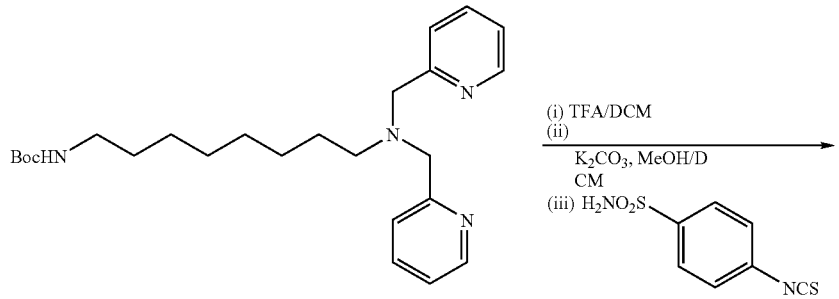
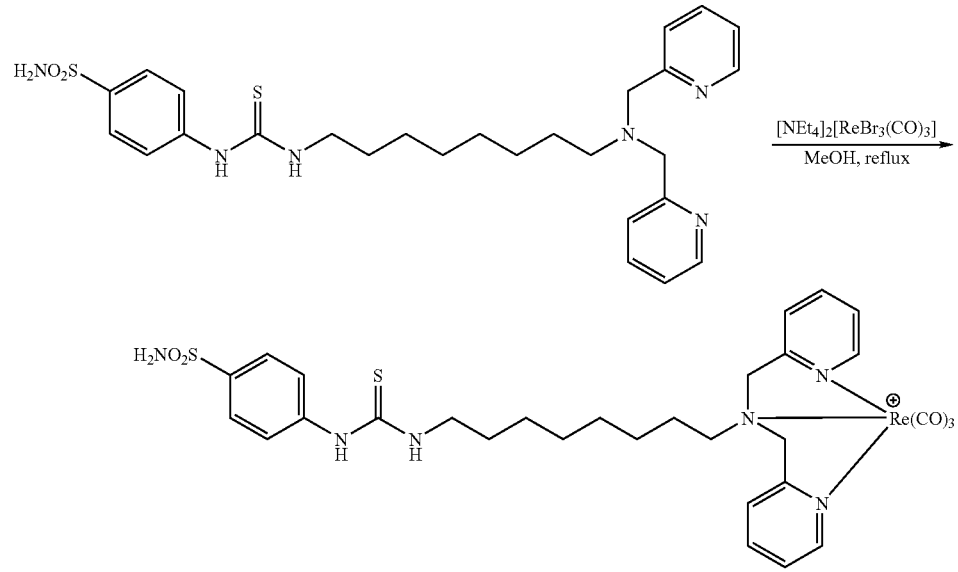

Example 1

[Re(CO)₃][2-((pyridin-2-ylmethyl)(4-sulfamoylphenethyl)amino) acetic acid]

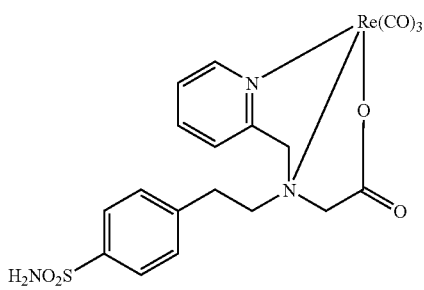

A. Synthesis of tert-butyl 2-((pyridin-2-ylmethyl)(4-sulfamoyl phenethyl)amino) acetate and tert-butyl 2,2'-(4-sulfamoylphenethyl azanediyl)diacetate

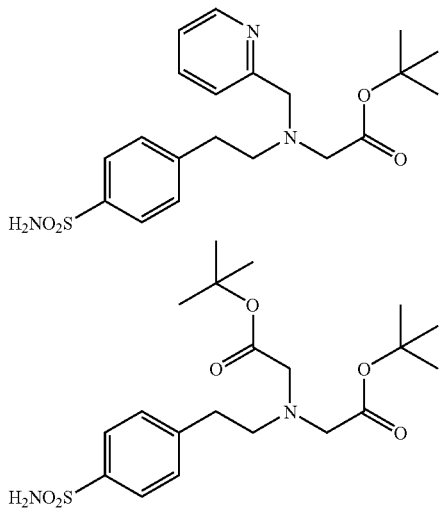

A solution of 4-(2-aminoethyl)benzenesulfonamide (1.60 g, 8.0 mmol), AcOH (0.30 mL) and 2-pyridinecarboxaldehyde (0.76 mL, 8.0 mmol) in DCE (50 mL) was heated at 75° C. for 30 min under nitrogen. The reaction mixture was cooled to 0° C., and treated sequentially with NaBH(OAc)₃ (6.36 g, 30 mmol) and crude tert-butyl glyoxalate (Yao, Z.; Bhaumik, J.; Dhanalekshmi, S.; Ptaszek, M.; Rodriguez, P. A.; Lindsey, J. S. *Tetrahedron*, 2007, 63, 10657-10670) (2.08 g). The reaction mixture was stirred at room temperature for overnight and quenched with water. The reaction mixture was extracted with DCM. The organic layer was dried and concentrated under reduced pressure. The residue was purified by flash chromatography over silica gel to afford tert-butyl 2-((pyridin-2-ylmethyl)(4-sulfamoylphenethyl)amino)acetate (1.04 g, 32%) and tert-butyl 2,2'-(4-sulfamoylphenethylazanediyl)diacetate (0.624 g, 18%). ¹H NMR (400 MHz, CD₃OD): tert-butyl 2-((pyridin-2-ylmethyl)(4-sulfamoylphenethyl)amino)acetate: δ 8.45 (d, J=4.8 Hz, 0.42H), 8.40 (d, J=4.8 Hz, 0.58H), 7.83 (t, J=6.4 Hz, 0.42H), 7.77 (d, J=8.4 Hz, 1.58H), 7.69 (t, J=8.0 Hz, 0.58H), 7.56 (d, J=7.6 Hz, 0.58H), 7.34-7.24 (m, 4H), 5.49 (s, 1H), 4.70 (s, 1H), 3.93 (s, 2H), 2.91 (t, J=6.8 Hz, 2H), 2.83 (t, J=6.8 Hz, 2H), 1.47 (s, 9H); ESMS m/z: 406 (M+H)⁺. ¹H NMR (400 MHz, CD₃Cl₃): tert-Butyl 2,2'-(4-sulfamoylphenethyl azanediyl) diacetate: δ 7.83 (d, J=8.4 Hz, 2H), 3.45 (s, 4H), 2.97 (t, J=5.6 Hz, 2H), 2.87 (t, J=6.0 Hz, 2H), 1.49 (s, 18H); ESMS m/z: 429 (M+H)⁺.

B. Synthesis of 2-((pyridin-2-ylmethyl)(4-sulfamoylphenethyl)amino)acetic acid

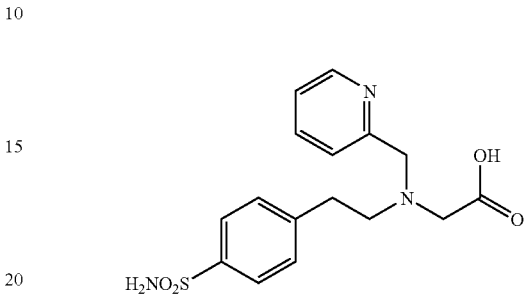

To a solution of tert-butyl 2-((pyridin-2-ylmethyl)(4-sulfamoylphenethyl)amino)acetate (150 mg, 0.37 mmol) in DCM (3.0 mL) and TFA (3.0 mL) was stirred at room temperature for overnight. The solvent was removed under reduced pressure to give 2-((pyridin-2-ylmethyl)(4-sulfamoylphenethyl)amino)acetic acid (129 mg, 100%). ¹H NMR (400 MHz, CD₃OD) δ 8.73 (d, J=5.6 Hz, 0.46 H), 8.58 (d, J=4.4 Hz, 1H), 8.57 (t, J=8.0 Hz, 0.46H), 8.16 (t, J=7.6 Hz, 1H), 8.01 (d, J=8.4 Hz, 0.54 H), 7.96 (t, J=6.8 Hz, 0.54H), 7.79 (d, J=8.4 Hz, 2H), 7.66 (d, J=7.2 Hz, 2H), 7.35 (d, J=8.4 Hz, 2H), 4.51 (s, 2H), 4.06 (s, 2H), 3.36 (t, J=7.6 Hz, 2H), 3.05 (t, J=7.6 Hz, 2H); ESMS m/z: 355 (M+H)⁺.

C. Synthesis of [Re(CO)₃][2-((pyridin-2-ylmethyl)(4-sulfamoylphenethyl)amino)acetic acid]. A solution of 2-((pyridin-2-ylmethyl)(4-sulfamoylphenethyl)amino)acetic acid (61 mg, 0.173 mmol), [NEt₄]₂[ReBr₃(CO)₃] (192 mg, 0.25 mmol) and K₂CO₃ (30 mg) in MeOH (6.0 mL) was stirred at 100° C. for 5 h in a sealed pressure tube. The reaction mixture was purified using Amberchrom™ (CG-161) resin eluting with MeOH/H₂O to give the tile compound (18.9 mg, 18%) as a white solid. ¹H NMR (400 MHz, DMSO-d₆) δ 8.77 (d, J=5.6 Hz, 1H), 8.17 (t, J=7.8 Hz, 1H), 7.79 (d, J=8.0 Hz, 2H), 7.74 (d, J=7.6 Hz, 1H), 7.59 (d, J=8.0 Hz, 2H), 7.58 (d, J=6.0 Hz, 1H), 7.29 (s, 2H), 4.92 (d, J=16.0 Hz, 1H), 4.77 (d, J=16.0 Hz, 1H), 4.10 (d, J=16.4 Hz, 1H), 3.74-3.68 (m, 1H), 3.64-3.58 (m, 1H), 3.53 (d, J=16.8 Hz, 1H), 3.14-3.08 (m, 2H); ESMS m/z: 620 (M+H)⁺.

Example 2

[Re(CO)₃][2-(((1-methyl-1H-imidazol-2-yl)methyl)(4-sulfamoylphenethyl)-amino)acetic acid]

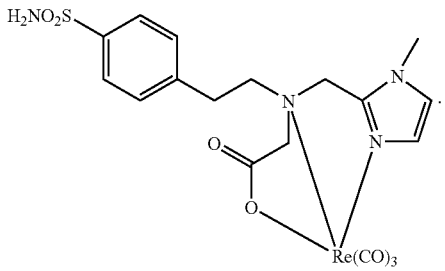

A. Synthesis of tert-butyl 2-(((1-methyl-1H-imidazol-2-yl)methyl)(4-sulfamoylphenethyl)amino)acetate

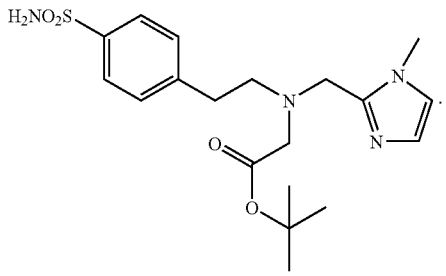

A solution of 4-(2-aminoethyl)benzenesulfonamide (1.40 g, 7.0 mmol), AcOH (0.30 mL) and 1-methyl-1H-imidazol-2-carboxaldehyde (0.77 g, 7.0 mmol) in DCE (40 mL) was heated at 80° C. for 30 min under nitrogen. The reaction mixture was cooled to 0° C., and treated sequentially with $NaBH(OAc)_3$ (4.45 g, 21 mmol) and tert-butyl glyoxalate (1.80 g). The reaction mixture was stirred at room temperature overnight and quenched with water. The reaction mixture was then extracted with DCM and the organic layer was dried and concentrated under reduced pressure. The residue obtained was purified by flash chromatography over silica gel to tert-butyl 2-(((1-methyl-1H-imidazol-2-yl)methyl)(4-sulfamoylphenethyl)amino)acetate (0.63 g, 22%). $^1$H NMR (400 MHz, DMSO-$d_6$) δ 7.65 (d, J=8.4 Hz, 2 H), 7.26 (s, 2 H), 7.21 (d, J=8.0 Hz, 2 H), 6.99 (d, J=0.8 Hz, 1 H), 6.73 (d, J=0.8 Hz, 1 H), 3.76 (s, 2 H), 3.38 (s, 3 H), 3.28 (s, 2 H), 2.79 (t, J=7.2 Hz, 2 H), 2.69 (t, J=6.8 Hz, 2 H), 1.40 (s, 9 H); ESMS m/z: 409 (M+H)$^+$.

B. Synthesis of [Re(CO)$_3$][2-(((1-methyl-1H-imidazol-2-yl)methyl)-(4-sulfamoylphenethyl)-amino)acetic acid]

To a solution tert-butyl 2-(((1-methyl-1H-imidazol-2-yl)methyl)(4-sulfamoylphenethyl)amino)acetate (110 mg, 0.27 mmol) in DCM (3.0 mL) and TFA (3.0 mL) was stirred at room temperature for overnight. Solvent was removed under reduced pressure to give 2-(((1-methyl-1H-imidazol-2-yl)methyl)(4-sulfamoylphenethyl)amino)acetic acid. A solution of 2-(((1-methyl-1H-imidazol-2-yl)methyl)(4-sulfamoylphenethyl)amino)acetic acid, $[NEt_4]_2[ReBr_3(CO)_3]$ (270 mg, 0.35 mmol) and $K_2CO_3$ (78 mg) in MeOH (6.0 mL) was stirred at 90° C. for 4 h at a pressure tube. The reaction mixture was purified using Amberchrom™ (CG-161) resin eluting with MeOH/H$_2$O to give the title compound (105 mg, 63%) as a white solid. $^1$H NMR (400 MHz, DMSO-$d_6$) δ 7.79 (d, J=8.0 Hz, 2H), 7.57 (d, J=8.0 Hz, 2H), 7.36 (d, J=0.8 Hz, 1H), 7.25 (s, 2H), 7.15 (d, J=1.2 Hz, 1H), 4.76 (d, J=16.4 Hz, 1H), 4.58 (d, J=16.0 Hz, 1H), 4.03 (d, J=16.8 Hz, 1H), 3.67 (d, J=16.8 Hz, 1 H), 3.65-3.49 (m, 2H), 3.17-3.09 (m, 2H); ESMS m/z: 623 (M+H)$^+$.

Example 3

[Re(CO)$_3$][2,2'-(2,2'-(4-sulfamoylphenethylazanediyl) bis(methylene)bis(1H-imidazole-2,1-diyl)) diacetic acid]

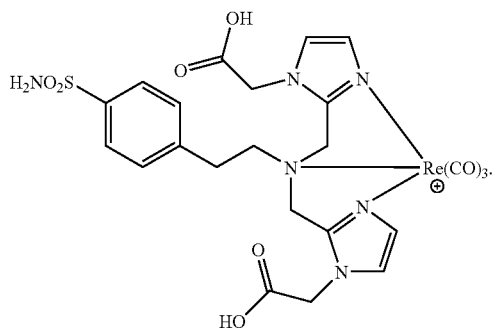

A. Tert-butyl 2,2'-(2,2'-(4-sulfamoylphenethylazanediyl)bis(methylene) bis(1H-imidazole-2,1-diyl)) diacetate

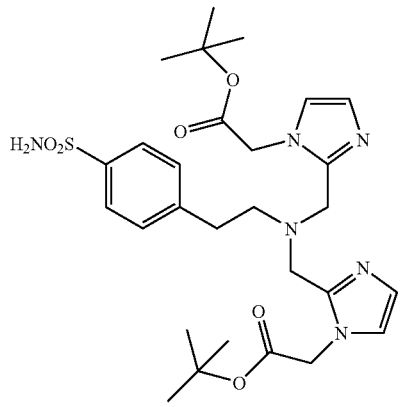

A solution of 4-(2-aminoethyl)benzenesulfonamide (110 mg, 0.55 mmol), AcOH (0.10 mL) and tert-butyl 2-(2-formyl-1H-imidazol-1-yl)acetate (250 mg, 1.19 mmol) in DCE (20 mL) was stirred at 80° C. for 30 min under nitrogen. The reaction mixture was cooled to 0° C., and treated with $NaBH(OAc)_3$ (0.423 g, 2.0 mmol). The reaction mixture was stirred at room temperature for overnight and quenched with water. The reaction mixture was extracted with DCM. The organic layer was dried and concentrated under reduced pressure. The residue was purified by flash chromatography over silica gel to afford tert-butyl sulfamoylphenethylazanediyl)bis(methylene)bis (1H-imidazole-2,1-diyl))diacetate (132 mg, 41%). $^1$H NMR (400 MHz, CD$_3$OD) δ 7.75 (d, J=8.4 Hz, 2H), 7.18 (d, J=8.4 Hz, 2H), 7.07 (s, 2H), 6.93 (s, 2H), 4.58 (s, 4H), 3.68 (s, 4H), 2.84-2.74 (m, 4H), 1.44 (s, 18H); ESMS m/z: 589.4 (M+H)$^+$.

B. [Re(CO)3][tert-butyl 2,2'-(2,2'-(4-sulfamoylphenethylazanediyl) bis(methylene)bis(1H-imidazole-2,1-diyl))diacetate]

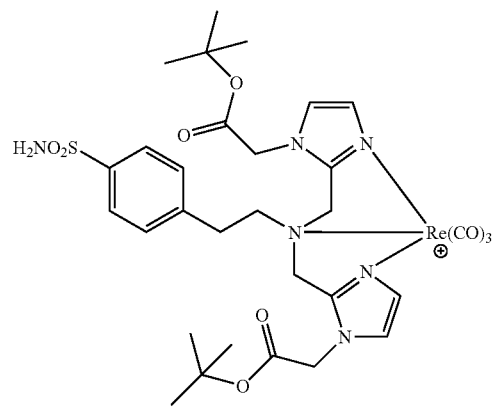

A solution of tert-butyl 2,2'-(2,2'-(4-sulfamoylphenethylazanediyl)bis(methylene)bis(1H-imidazole-2,1-diyl))diacetate (65 mg, 0.11 mmol) and $[NEt_4]_2[ReBr_3(CO)_3]$ (92.4 mg, 0.12 mmol) in MeOH (3.0 mL) was stirred at 95° C. for 4 h at a pressure tube. The reaction mixture was purified by Amberchrom™ (CG-161) resin eluting with MeOH/H$_2$O to give the title compound (51 mg, 54%) as a white solid. $^1$H NMR (400 MHz, DMSO-$d_6$) δ 7.81 (d, J=8.4 Hz, 2H), 7.60 (d, J=8.4 Hz, 2H), 7.31 (s, 2H), 7.26 (d, J=1.2 Hz, 2H), 7.12 (d, J=1.2 Hz, 2H), 4.95 (s, 4H), 4.74 (d, J=16.4 Hz, 2H), 4.62 (d, J=16.4 Hz, 2H), 3.90-3.86 (m, 2H), 3.16-3.14 (m, 2H), 1.45 (s, 18H); ESMS m/z: 859.3 M$^+$.

C. [Re(CO)$_3$][2,2'-(2,2'-(4-sulfamoylphenethylazanediyl) bis(methylene) bis(1H-imidazole-2,1-diyl))diacetic acid]. A solution of [Re(CO)$_3$][tert-butyl 2,2'-(2,2'-(4-sulfamoylphenethylazanediyl)-bis(methylene)bis(1H-imidazole-2,1-diyl))diacetate] (20 mg) in TFA (1.0 mL) and DCM (1.0 mL) was stirred at room temperature for 4 h. The solvent was removed under reduced pressure to give the title compound (21.5 mg). $^1$H NMR (400 MHz, DMSO-d$_6$) δ 7.81 (d, J=8.0 Hz, 2H), 7.60 (d, J=8.4 Hz, 2H), 7.30 (s, 2H), 7.23 (d, J=1.2 Hz, 2H), 7.08 (d, J=1.2 Hz, 2H), 4.91 (s, 4H), 4.72 (s, 4H), 3.89-3.85 (m, 2H), 3.18-3.14 (m, 2H); ESMS m/z: 747.2.

Example 4

[Re(CO)$_3$][2,2'-(2,2'-(4-sulfamoylbenzylazanediyl) bis(methylene)bis(1H-imidazole-2,1-diyl))diacetic acid]

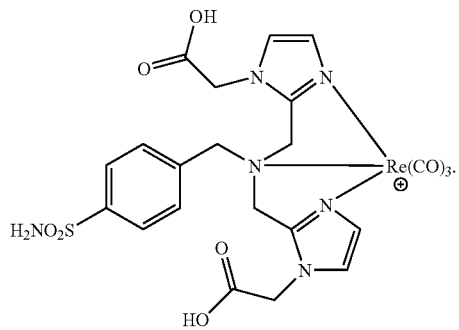

A. Synthesis of tert-butyl 2,2'-(2,2'-(4-sulfamoylbenzylazanediyl) bis(methylene)bis(1H-imidazole-2,1-diyl))diacetate

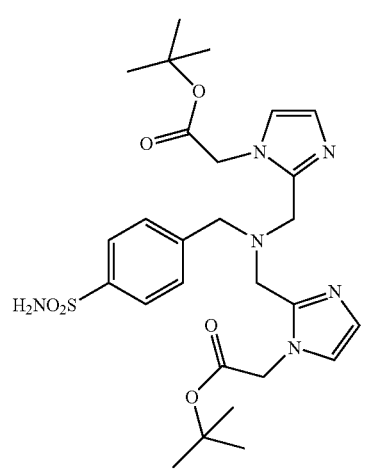

A solution of 4-(2-aminomethyl)benzenesulfonamide hydrochloride (223 mg, 1.0 mmol) and tert-butyl 2-(2-formyl-1H-imidazol-1-yl)acetate (441 mg, 2.1 mmol) in DCE (20 mL) was stirred at 75° C. for 30 min under nitrogen. The reaction mixture was cooled to 0° C., and treated with NaBH(OAc)$_3$ (0.633 g, 3.0 mmol). The reaction mixture was stirred at room temperature for overnight and quenched with water. The was reaction mixture was concentrated under reduced pressure. The residue was purified by biotage with a gradient of 0-10% MeOH in DCM to tert-butyl 2,2'-(2,2'-(4-sulfamoylbenzylazanediyl)bis(methylene) bis(1H-imidazole-2,1-diyl))diacetate (569 mg, 99%) as a yellow oil. $^1$H NMR (400 MHz, CD$_3$Cl$_3$) δ 7.83 (d, J=8.4 Hz, 2H), 7.41 (d, J=8.4 Hz, 2H), 6.97 (s, 2H), 6.82 (s, 2H), 4.66 (s, 2H), 4.43 (s, 2H), 3.83 (s, 1H), 3.73 (s, 1H), 3.61 (s, 2H), 3.48 (s, 4H), 1.39 (s, 18H); MS (ESI), 575.3 (M+H)$^+$.

B. [Re(CO)$_3$][2,2'-(2,2'-(4-sulfamoylbenzylazanediyl)bis(methylene)bis(1H-imidazole-2,1-diyl))diacetic acid]. A solution of to tert-butyl 2,2'-(2,2'-(4-sulfamoylbenzylazanediyl)bis(methylene)bis(1H-imidazole-2,1-diyl))diacetate (40 mg, 0.070 mmol) and [NEt$_4$]$_2$[ReBr$_3$(CO)$_3$] (60 mg, 0.077 mmol) in MeOH (3.0 mL) was stirred at 90° C. for 5 h at a pressure tube. The solvent was evaporated under reduced pressure to give a residue. A solution of the above residue in TFA (3.0 mL) and DCM (3.0 mL) was stirred at room temperature for 3 h. The solvent was removed under reduced pressure to a residue, which was purified by HPLC to give the title compound (23 mg, 45% over 2 steps) as a white solid. $^1$H NMR (400 MHz, DMSO-d$_6$) δ 7.93 (d, J=8.0 Hz, 2H), 7.86 (d, J=8.4 Hz, 2H), 7.47 (s, 2H), 7.14 (d, J=1.2 Hz, 2H), 7.06 (d, J=1.2 Hz, 2H), 4.92 (s, 2H), 4.79 (d, J=16.0 Hz, 2H), 4.76 (s, 4H), 4.20 (d, J=16.0 Hz, 2H); ESMS m/z: 733.1.

Example 5

[Re(CO)$_3$][4-(2-(bis(isoquinolin-1-ylmethyl)amino) ethyl)benzenesulfonamide]

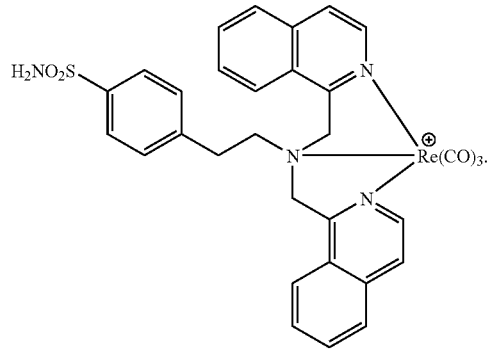

A. 4-(2-(bis(isoquinolin-1-ylmethyl)amino)ethyl) benzenesulfonamide

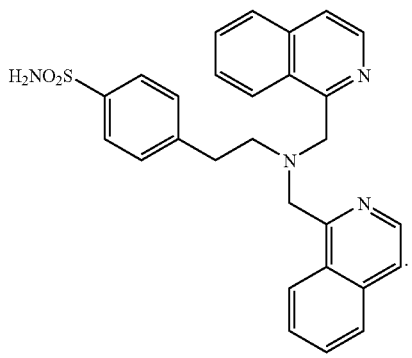

A solution of 4-(2-aminoethyl)benzenesulfonamide (1.0 g, 5.0 mmol), AcOH (1.0 mL) and isoquinoline-1-carbaldehyde (2.09 g, 13.3 mmol) in DCE (50 mL) was stirred at 75° C. for 30 min under nitrogen. The reaction mixture was cooled to 0° C., and treated with NaBH(OAc)$_3$ (3.165 g, 15 mmol). The reaction mixture was stirred at room temperature for overnight and quenched with water. The reaction mixture was extracted with DCM. The organic layer was dried and concentrated under reduced pressure. The residue was purified by flash chromatography over silica gel to afford 4-(2-(bis(isoquinolin-1-ylmethyl)amino)ethyl)benzenesulfonamide (1.86 g, 77%). $^1$H NMR (400 MHz, DMSO-d$_6$) δ 8.24 (d, J=8.8 Hz, 2H), 7.96 (d, J=8.4 Hz, 2H), 7.91 (d, J=8.0 Hz, 2H), 7.72 (t, J=7.8 Hz, 2H), 7.65 (d, J=8.4 Hz, 2H), 7.55 (t, J=7.6 Hz, 2H), 7.50 (d, J=8.4 Hz, 2H), 7.30 (d, J=6.0 Hz, 2H), 7.29 (s, 2H), 4.01 (s, 4 H), 2.94 (t, J=7.0 Hz, 2H), 2.78 (t, J=7.0 Hz, 2H); ESMS m/z: 483.3 (M+H)$^+$.

B. [Re(CO)$_3$][4-(2-(bis(isoquinolin-1-ylmethyl)amino) ethyl)benzenesulfonamide]. A solution of 4-(2-(bis(isoquinolin-1-ylmethyl)amino)ethyl)benzenesulfonamide (230 mg, 0.477 mmol) and [NEt$_4$]$_2$[ReBr$_3$(CO)$_3$] (367 mg, 0.477 mmol) in MeOH (6.0 mL) was stirred at 100° C. for 3 hrs at a pressure tube. The reaction mixture was purified by Amberchrom™ resin eluting with MeOH/H$_2$O to give the product (173 mg, 48%) as a yellow solid. $^1$H NMR (400 MHz, DMSO-d$_6$) δ 8.69 (d, J=8.4 Hz, 2H), 8.36 (d, J=8.8 Hz, 2H), 8.12 (d, J=8.4 Hz, 2H), 7.95 (t, J=7.4 Hz, 2H), 7.82 (d, J=8.4 Hz, 2H), 7.75 (t, J=7.6 Hz, 2H), 7.70 (d, J=8.4 Hz, 2H), 7.62 (d, J=8.4 Hz, 2H), 7.34 (s, 2H), 5.46 (d, J=18.0 Hz, 2H), 5.25 (d, J=18.0 Hz, 2H), 4.07-4.03 (m, 2H), 3.32-2.99 (m, 2H); ESMS m/z: 753.2 M.

Example 6

[Re(CO)$_3$][2-(2-(((carboxymethyl)(4-sulfamoylphenethyl)amino) methyl)-1H-imidazol-1-yl)acetic acid]

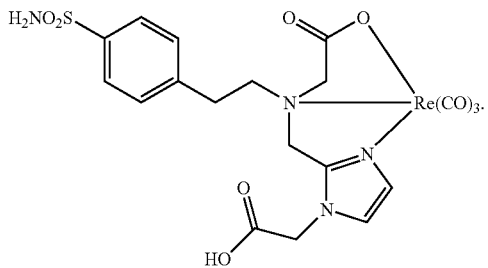

A. tert-butyl 2-(2-(((2-tert-butoxy-2-oxoethyl)(4-sulfamoylphenethyl)amino)methyl)-1H-imidazol-1-yl)acetate

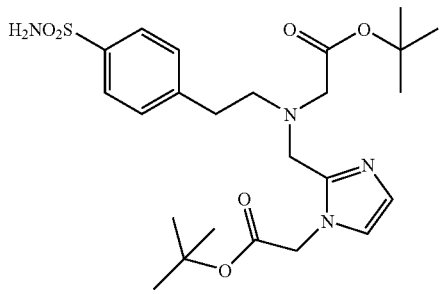

A solution of 4-(2-aminoethyl)benzenesulfonamide (0.70 g, 3.5 mmol), AcOH (0.20 mL) and tert-butyl 2-(2-formyl-1H-imidazol-1-yl)acetate (0.735 g, 3.5 mmol) in DCE (20 mL) was heated at 80° C. for 30 min under nitrogen. The reaction mixture was cooled to 0° C., and treated sequentially with NaBH(OAc)$_3$ (2.25 g, 10.5 mmol) and tert-butyl glyoxalate (1.80 g). The reaction mixture was stirred at room temperature overnight and quenched with water. The reaction mixture was extracted with DCM and the organic layer was dried and concentrated under reduced pressure. The residue was purified by flash chromatography over silica gel to afford tert-butyl 2-(((1-methyl-1H-imidazol-2-yl)methyl)(4-sulfamoylphenethyl)amino)acetate (0.63 g, 35%). $^1$H NMR (400 MHz, DMSO-d$_6$) δ 7.67 (d, J=8.4 Hz, 2H), 7.25 (s, 2H), 7.23 (d, J=8.4 Hz, 2H), 7.04 (d, J=1.2 Hz, 1H), 6.76 (d, J=1.2 Hz, 1H), 4.82 (s, 2H), 3.74 (s, 2H), 3.24 (s, 2H), 2.69-2.66 (m, 4H), 1.41 (s, 9H), 1.40 (s, 9H); ESMS m/z: 509 (M+H)$^+$.

B. [Re(CO)$_3$][2-(2-(((carboxymethyl)(4-sulfamoylphenethyl)amino) methyl)-1H-imidazol-1-yl)acetic acid]. To a solution tert-butyl 2-(((1-methyl-1H-imidazol-2-yl)methyl)(4-sulfamoylphenethyl)amino)acetate (40 mg, 0.079 mmol) in DCM (2.0 mL) and TFA (2.0 mL) was stirred at room temperature for 3 hrs. The solvent was removed under reduced pressure to give 2-(2-(((carboxymethyl)(4-sulfamoylphenethyl)amino)methyl)-1H-imidazol-1-yl)acetic acid. A solution of 2-(2-(((carboxymethyl)(4-sulfamoylphenethyl)amino)methyl)-1H-imidazol-1-yl)acetic acid and [NEt$_4$]$_2$[ReBr$_3$(CO)$_3$] (70 mg, 0.09 mmol) in MeOH (2.0 mL) and H$_2$O (2.0 mL) was adjusted to pH=9 using 2 N NaOH. The mixture was stirred at 95° C. overnight in a pressure tube. The reaction mixture was purified by HPLC to give the product (20 mg, 38%) as a white solid. $^1$H NMR (400 MHz, DMSO-d$_6$) δ 7.76 (d, J=8.0 Hz, 2H), 7.57 (d, J=8.0 Hz, 2H), 7.36 (d, J=1.6 Hz, 1H), 7.26 (s, 2H), 7.16 (d, J=1.6 Hz, 1H), 5.05 (d, J=16.4 Hz, 1H), 4.98 (d, J=16.4 Hz, 1H), 4.73 (d, J=16.0 Hz, 1H), 4.43 (d, J=16.0 Hz, 1H), 4.00 (d, J=16.8 Hz, 1H), 3.60-3.51 (m, 3H), 3.10-3.05 (m, 2H); ESMS m/z: 667.2 (M+H)$^+$.

Example 7

[Re(CO)$_3$][2,2'-(4-sulfamoylphenethylazanediyl) diacetic acid]

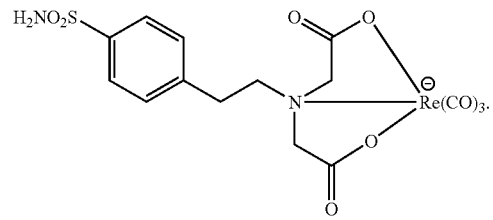

To a solution of tert-butyl 2,2'-(4-sulfamoylphenethylazanediyl)diacetate (40 mg, 0.094 mmol) in DCM (2.0 mL) and TFA (2.0 mL) was stirred at room temperature overnight. The solvent was removed under reduced pressure to give 2,2'-(4-sulfamoylphenethylazanediyl)diacetic acid. A solution of 2,2'-(4-sulfamoylphenethylazanediyl)diacetic acid and Re(CO)$_3$(H$_2$O)$_3$OTf (1.5 mL, 0.10 mmol/mL in water, 0.15 mmol) in water (3.0 mL) was adjusted to pH=9 using 2N NaOH. The mixture was stirred at room temperature overnight. The reaction mixture was purified by HPLC to give the product (19.2 mg, 31%) as a white solid. $^1$H NMR (400 MHz, DMSO-d$_6$) δ 7.73 (d, J=8.4 Hz, 2H), 7.53 (d, J=8.4 Hz, 2H), 7.24 (s, 2H), 3.74 (d, J=15.6 Hz, 2H), 3.47 (d, J=15.6 Hz, 2H).

Example 8

[Re(CO)$_3$][2,2'-(2,2'-(4-sulfamoylphenethylazanediyl) bis(methylene)bis(1H-imidazole-2,1-diyl-acetylazanediyl))diacetic acid]

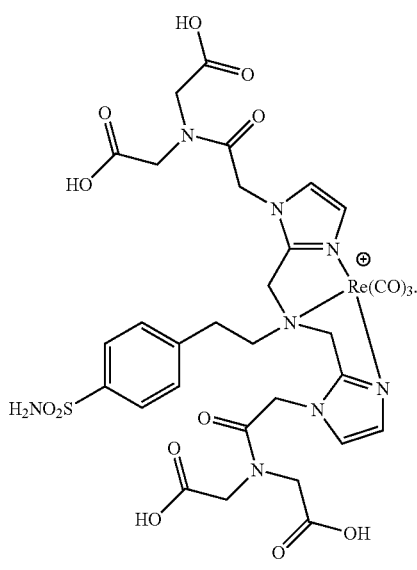

A. Synthesis of tert-Butyl 2,2'-(2-bromoacetylazanediyl)diacetate

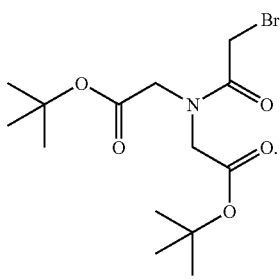

To a solution of tert-butyl 2,2'-azanediyldiacetate (3.00 g, 12.24 mmol) and 2-bromoacetyl bromide (1.39 mL, 3.23 g, 16.00 mmol) in DCM (100 mL) was added Et$_3$N (2.0 mL) at room temperature. The reaction mixtures were stirred at room temperature for 2 h. The reaction mixtures were diluted with DCM (300 mL), washed with water, and dried over sodium sulfate. The solvent was evaporated under reduce pressure to afford a residue, which was purified on a Biotage SP4 eluting with 10% hexanes in ethyl acetate to 50% hexanes in EtOAc to tert-butyl 2,2'-(2-bromoacetylazanediyl)diacetate (4.68 g, 100%). $^1$H NMR (400 MHz, CDCl$_3$) δ 4.09 (s, 2H), 4.07 (s, 2H), 3.86 (s, 2H), 1.49 (s, 9H), 1.46 (s, 9H); ESMS m/z: 388, 390 (M+Na)$^+$.

B. Synthesis of tert-Butyl 2,2'-(2-(2-formyl-1H-imidazol-1-yl)acetyl azanediyl)diacetate

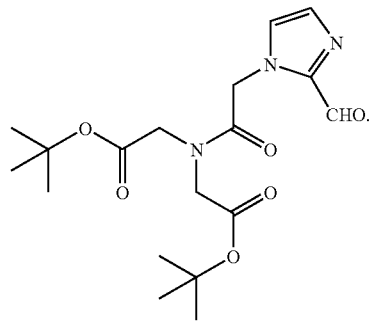

A solution of tert-butyl 2,2'-(2-bromoacetylazanediyl)diacetate (4.55 g, 12.43 mmol), 1H-imidazole-2-carbaldehyde (1.54 g, 16.0 mmol), DIPEA (5.0 mL), and potassium iodide (0.64 g, 4.0 mmol) was stirred at 80° C. overnight. After the solvents were evaporated under reduced pressure, the reaction mixture was diluted with DCM, washed with water and dried. The solvent was evaporated under reduce pressure to afford a residue, which was purified utilizing a Biotage SP4 eluting with DCM to 3% MeOH in DCM to tert-butyl 2,2'-(2-(2-formyl-1H-imidazol-1-yl)acetylazanediyl)diacetate (3.96 g, 84%). $^1$H NMR (400 MHz, CDCl$_3$) δ 9.76 (s, 1H), 7.31 (s, 1H), 7.25 (s, 1H), 5.30 (s, 2H), 4.14 (s, 2H), 4.07 (s, 2H), 1.51 (s, 9H), 1.43 (s, 9H); ESMS m/z: 382 (M+H)$^+$.

C. Synthesis of tert-butyl 2,2'-(2,2'-(4-sulfamoylphenethylazanediyl) bis(methylene)bis(1H-imidazole-2,1-diyl-acetylazanediyl))diacetate

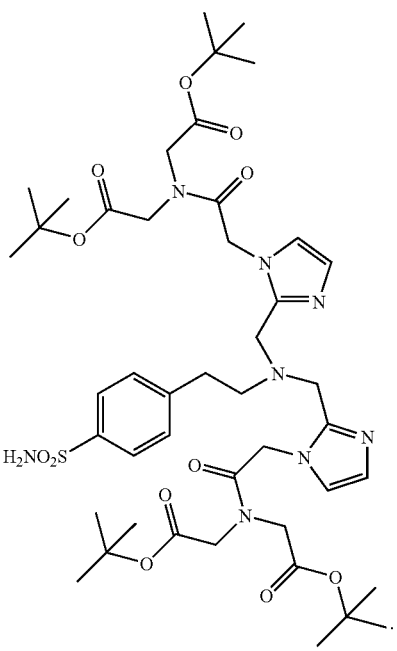

A solution of 4-(2-aminoethyl)benzenesulfonamide (100 mg, 0.50 mmol), AcOH (0.10 mL) and tert-butyl 2,2'-(2-(2-formyl-1H-imidazol-1-yl)acetylazanediyl)diacetate (457 mg, 1.2 mmol) in DCE (30 mL) was stirred at 75° C. for 30 min under nitrogen. The reaction mixture was cooled to 0° C., and treated with NaBH(OAc)$_3$ (0.423 g, 2.0 mmol). The reaction mixture was stirred at room temperature overnight and quenched with water. The reaction mixture was then extracted with DCM and the organic layer was dried and concentrated under reduced pressure. The residue was purified by Biotage SP4 over silica gel to afford the compound (465 mg, 100%). $^1$H NMR (400 MHz, DMSO-d$_6$) δ 7.63 (d, J=8.0 Hz, 2H), 7.23-7.21 (m, 4H), 6.96 (s, 2H), 6.79 (s, 2H), 5.00 (s, 4H), 4.30 (s, 4H), 3.95 (s, 4H), 3.59 (s, 4H), 2.70-2.66 (m, 2H), 2.59-2.55 (m, 2H), 1.42 (s, 18H), 1.33 (s, 18H); ESMS m/z: 466.4 (M/2+H)$^+$.

D. [Re(CO)$_3$][2,2'-(2,2'-(4-sulfamoylphenethylazanediyl) bis(methylene) bis(1H-imidazole-2,1-diyl-acetylazanediyl)) diacetic acid]. A solution of tert-butyl 2,2'-(2,2'-(4-sulfamoylphenethylazanediyl) bis(methylene) bis(1H-imidazole-2,1-diyl-acetylazanediyl))diacetateate (32 mg, 0.34 mmol) and [NEt$_4$]$_2$[ReBr$_3$(CO)$_3$] (30 mg, 0.39 mmol) in MeOH (3.0 mL) was stirred at 95° C. for 4 h in a sealed pressure tube. The solvent was evaporated under reduced pressure to give crude product. A solution of crude product in TFA (1.0 mL) and DCM (1.0 mL) was stirred at room temperature for 3 h. The solvent was removed under reduced pressure to give a residue, which was purified by HPLC to give the title compound as a white solid (33 mg, 27%). $^1$H NMR (400 MHz, DMSO-d$_6$) δ 7.79 (d, J=8.4 Hz, 2H), 7.58 (d, J=8.0 Hz, 2H), 7.29 (s, 2H), 7.13 (s, 2H), 7.06 (s, 2H), 5.06 (s, 4H), 4.65 (d, J=16.4 Hz, 2H), 4.40 (d, J=16.4 Hz, 2H), 4.29 (s, 4H), 4.05 (d, J=5.6 Hz, 4H), 3.87-3.83 (m, 2H), 3.11-3.08 (m, 2H); ESMS m/z: 978 M$^+$.

Example 9

[Re(CO)$_3$][4-(3-(5-(bis(pyridin-2-ylmethyl)amino) pentyl) thioureido)benzenesulfonamide]

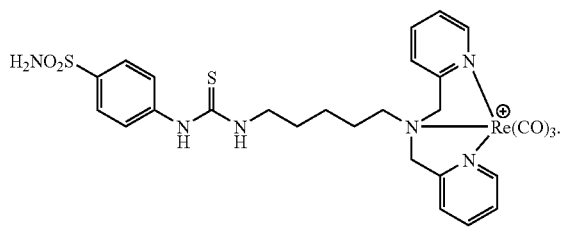

A. 4-(3-(5-(bis(pyridin-2-ylmethyl)amino)pentyl) thioureido) benzenesulfonamide

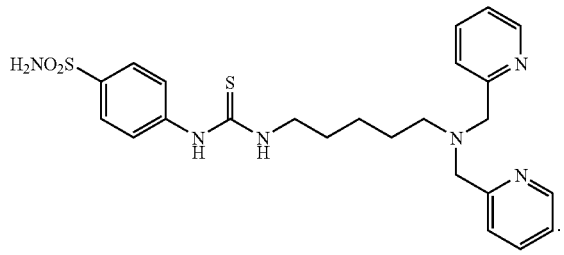

A solution of tert-butyl 5-(bis(pyridin-2-ylmethyl)amino) pentylcarbamate (0.63 g, 1.64 mmol) in DCM (10 mL) and TFA (1.0 mL) was stirred at room temperature for 3 h. Upon completion the solvent was evaporated and the reaction mixture was diluted with DCM, washed with saturated aqueous potassium carbonate and concentrated under vacuum to afford N,N-bis(pyridin-2-ylmethyl)pentane-1,5-diamine. A solution of the above product N,N-bis(pyridin-2-ylmethyl) pentane-1,5-diamine, 4-isothiocyanatobenzenesulfonamide (0.35 g, 1.64 mmol) in acetonitrile (10 mL) and DIPEA (0.40 mL) was stirred at 50° C. under nitrogen for 3 h. The solvent was evaporated under reduced pressure to give a crude product, which was purified by flash chromatography eluting utilizing 5% MeOH in DCM followed by 15% MeOH in DCM to give 4-(3-(5-(bis(pyridin-2-ylmethyl)amino)pentyl)thioureido) benzenesulfonamide (0.145 g, 19%) as a white solid. $^1$H NMR (400 MHz, DMSO-d$_6$) δ 9.75 (s, 1H), 8.48 (d, 2H), 7.98 (s, 1H), 7.78-7.69 (m, 4H), 7.63 (d, 2H), 7.53 (d, 2H), 7.29-7.21 (m, 4H), 3.55 (s, 4H), 3.46-3.44 (m, 2H), 2.49-2.47 (m, 2H), 1.56-1.42 (m, 2H), 1.32-1.28 (m, 2H); ESMS m/z: 499.5 (M+H)$^+$.

B. [Re(CO)$_3$][4-(3-(5-(bis(pyridin-2-ylmethyl)amino) pentyl)thioureido) benzenesulfonamide]. A solution of 4-(3-(5-(bis(pyridin-2-ylmethyl)amino)pentyl)thioureido) benzenesulfonamide (30 mg, 0.060 mmol) and [NEt$_4$]$_2$[ReBr$_3$(CO)$_3$] (43 mg, 0.06 mmol) in MeOH (6.0 mL) was stirred at 100° C. for 5 h in a sealed pressure tube. The reaction mixture was purified by Amberchrom™ resin eluting with MeOH/H$_2$O to give [Re(CO)$_3$][2-((pyridin-2-ylmethyl)(4-sulfamoylphenethyl)amino)acetic acid] (31 mg, 67%) as a white solid. ESMS m/z: 769.2 (M+H)$^+$.

Example 10

[Re(CO)$_3$][2-((pyridin-2-ylmethyl)(8-(3-(4-sulfamoylphenyl) thioureido)octyl)amino) acetic acid]

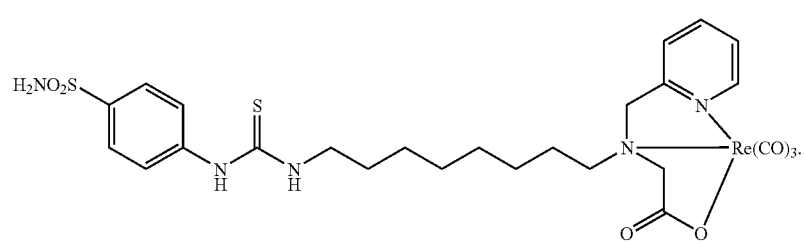

A. tert-butyl 2-((8-(tert-butoxycarbonylamino)octyl)(pyridin-2-ylmethyl)amino)acetate

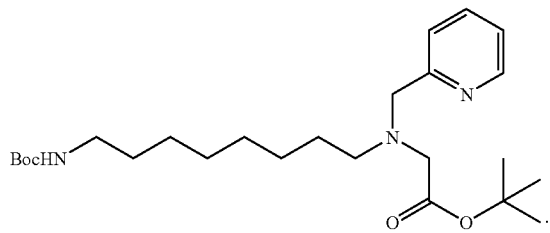

A solution of tert-butyl 8-aminooctylcarbamate (1.61 g, 6.588 mmol), 2-pyridinecarboxaldehyde (0.63 mL, 6.588 mmol) and AcOH (0.10 mL) in DCE (30 mL) was heated at 75° C. for 30 min under nitrogen. The reaction mixture was cooled to 0° C., and treated sequentially with NaBH(OAc)$_3$ (3.708 g, 17.5 mmol) and tert-butyl glyoxalate (1.53 g)[1]. The reaction mixture was stirred at room temperature overnight and quenched with water. The reaction mixture was then extracted with DCM and the organic layers was dried and concentrated under reduced pressure. The residue was purified by flash chromatography over silica gel to afford tert-butyl 2-((8-(tert-butoxycarbonylamino)octyl)(pyridin-2-ylmethyl)amino)acetate (1.71 g, 58%) as a yellow oil. $^1$H NMR (400 MHz, CD$_3$Cl$_3$) δ 8.52 (d, J=4.8 Hz, 1H), 7.65 (td, J=7.8, 1.6 Hz, 1H), 7.56 (d, J=7.6, 1H), 7.18-7.12 (m, 1H), 4.50 (s, 1H), 3.90 (s, 2H), 3.28 (s, 2H), 3.07 (q, J=6.3 Hz, 2H), 2.61 (t, J=7.6 Hz, 2H), 1.50-1.24 (m, 30H); ESMS m/z: 450.4 (M+H)$^+$.

B. 2-((pyridin-2-ylmethyl)(8-(3-(4-sulfamoylphenyl)thioureido)octyl)amino)acetic acid. A solution of tert-butyl 2-((8-(tert-butoxycarbonylamino)octyl)(pyridin-2-ylmethyl)amino)acetate (0.449 g, 1.0 mmol) in DCM (4 mL) and TFA (4.0 mL) was stirred at room temperature for overnight. The solvent was evaporated to afford 2-((8-aminooctyl)(pyridin-2-ylmethyl)amino)acetic acid. A solution of the above product 2-((8-aminooctyl)(pyridin-2-ylmethyl)amino)acetic acid, 4-isothiocyanatobenzenesulfonamide (0.278 g, 1.3 mmol) in CH$_3$CN (40 mL) and DIPEA (3.0 mL) was stirred at 50° C. under nitrogen for 48 h. The solvent was evaporated under reduced pressure to give a crude product, which was purified by Amberchrom™ eluting with acetonitrile/water to give 2-((pyridin-2-ylmethyl)(8-(3-(4-sulfamoylphenyl)thioureido)octyl)amino)acetic acid (0.500 g) as a colorless oil. $^1$H NMR (400 MHz, DMSO-d$_6$) δ 9.84 (s, 1H), 8.65 (d, J=4.4 Hz, 1H), 8.11 (s, 1H), 7.94 (td, J=7.6, 1.6 Hz, 1H), 7.70 (d, J=8.8 Hz, 2H), 7.63 (d, J=8.8 Hz, 2H), 7.57 (d, J=7.6 Hz, 1H), 7.50-7.47 (m, 1H), 7.26 (s, 2H), 4.53 (s, 2H), 4.14 (s, 2H), 3.44-3.40 (m, 2H), 3.14-3.08 (m, 2H), 1.64-1.24 (m, 1 H); ESMS m/z: 508.3 (M+H)$^+$.

C. [Re(CO)$_3$][2-((pyridin-2-ylmethyl)(8-(3-(4-sulfamoylphenyl)thioureido) octyl)amino)acetic acid]. A solution of 2-((pyridin-2-ylmethyl)(8-(3-(4-sulfamoylphenyl)thioureido)octyl)amino)acetic acid (60 mg) and [NEt$_4$]$_2$[ReBr$_3$(CO)$_3$] (77 mg, 0.10 mmol) in MeOH (4.0 mL) and water (0.20 mL) was stirred at 90° C. for overnight at a pressure tube. The reaction mixture was purified by HPLC to give the title compound (7.2 mg) as a white solid. $^1$H NMR (400 MHz, DMSO-d$_6$) δ 9.76 (s, 1H), 8.74 (d, J=5.2 Hz, 1H), 8.13 (td, J=7.6, 1.2 Hz, 1H), 8.04 (s, 1H), 7.72-7.62 (m, 5H), 7.56 (t, J=6.4 Hz, 1H), 7.25 (s, 2H), 4.74 (d, J=15.6 Hz, 1H), 4.52 (d, J=15.6 Hz, 1H), 3.80 (d, J=16.8 Hz, 1H), 3.54-3.40 (m, 4H), 3.38 (d, J=16.8 Hz, 1H), 1.76-1.31 (m, 12H); ESMS m/z: 778.1 (M+H)$^+$.

Synthesis of Exemplary Compounds of Formula II

Example 11

[Re(CO)$_3$][(S)-6-(bis((1-(carboxymethyl)-1H-imidazol-2-yl)methyl)amino)-2-(3-((S)-1-carboxy-4-oxo-4-(4-sulfamoylphenethylamino)butyl)ureido) hexanoic acid]

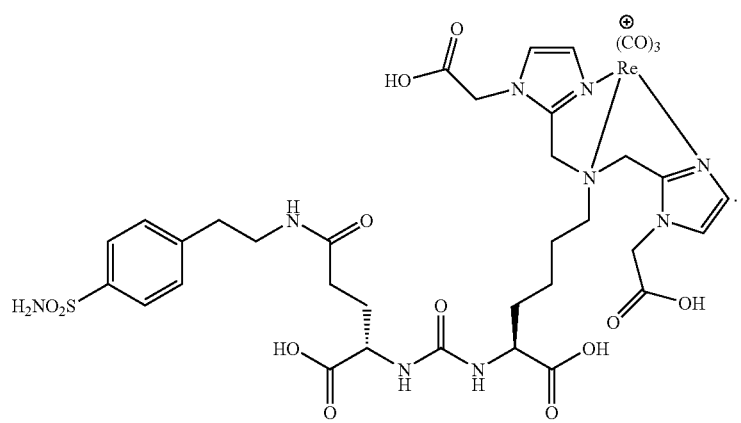

A. Synthesis of (9S,13S)-15-benzyl 13,9-di-tert-butyl 3,11-dioxo-1-phenyl-2-oxa-4,10,12-triazapentadecane-9,13,15-tricarboxylate

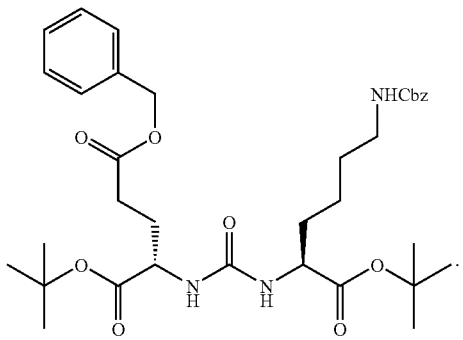

To a solution of L-Glu(OBn)-OtBu hydrochloride (3.13 mg, 9.49 mmol) and triphosgene (923 mg, 3.13 mmol) in DCE (70 mL) cooled to −78° C. was added triethylamine (2.80 mL) under nitrogen. After stirring at −78° C. for 2 h, a solution of L-Lys(Z)-OtBu (3.88 g, 10.40 mmol) and TEA (1.5 mL) in DCE (10 mL) was added. The mixture was allowed to come to room temperature over a period of 1 h and stirred at room temperature overnight. The reaction was quenched with 1N HCl, and extracted with DCM. The organic layer was dried and concentrated under reduced pressure and the residue was purified utilizing a Biotage SP4 to afford (9S,13S)-15-benzyl 13,9-di-tert-butyl 3,11-dioxo-1-phenyl-2-oxa-4,10,12-triazapentadecane-9,13,15-tricarboxylate as a colorless oil (4.71 g, 76%). $^1$H NMR (400 MHz, CDCl$_3$) δ 7.34-7.29 (m, 10H), 5.13-5.04 (m, 6H), 4.97 (brs, 1H), 4.38-4.28 (m, 2H), 3.18-3.14 (m, 2H), 2.50-2.35 (m, 2H), 2.19-2.10 (m, 1H), 1.94-1.85 (m, 1H), 1.79-1.72 (m, 1H), 1.58-1.33 (m, 21H).

B. Synthesis of (S)-4-(3-((S)-6-amino-1-tert-butoxy-1-oxohexan-2-yl)ureido)-5-tert-butoxy-5-oxopentanoic acid

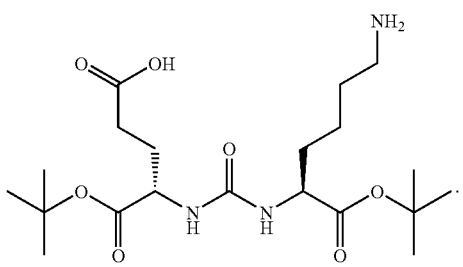

A suspension of (9S,13S)-15-benzyl 13,9-di-tert-butyl 3,11-dioxo-1-phenyl-2-oxa-4,10,12-triazapentadecane-9,13,15-tricarboxylate (4.30 g, 6.64 mmol), 10% Pd/C (1.0 g) and ammonium formate (4.0 g) in EtOH (70 mL) under a empty balloon was stirred at room temperature overnight. The reaction mixture was filtered through a pad of Celite and washed with EtOAc. The solvent was evaporated to give (S)-4-(3-((S)-6-amino-1-tert-butoxy-1-oxohexan-2-yl)ureido)-5-tert-butoxy-5-oxopentanoic acid (4.07 g, 70%) which was used without further purification. ESMS m/z: 432.3 (M/2+H)$^+$.

C. Synthesis of (S)-4-(3-((S)-6-(bis((1-(2-tert-butoxy-2-oxoethyl)-1H-imidazol-2-yl)methyl)amino)-1-tert-butoxy-1-oxohexan-2-yl)ureido)-5-tert-butoxy-5-oxopentanoic acid

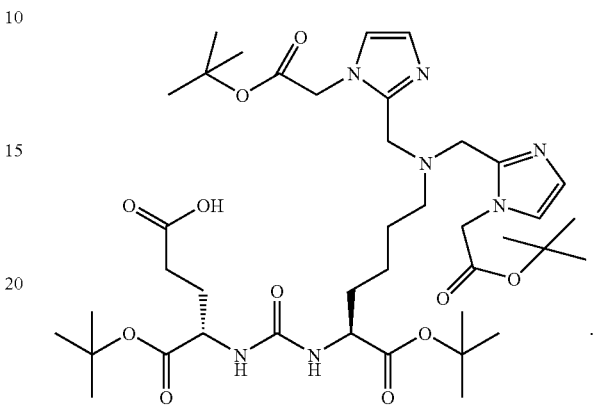

A solution of (S)-4-(3-((S)-6-amino-1-tert-butoxy-1-oxohexan-2-yl)ureido)-5-tert-butoxy-5-oxopentanoic acid (432 mg, 70% pure, 0.70 mmol), AcOH (0.10 mL) and tert-butyl 2-(2-formyl-1H-imidazol-1-yl)acetate (470 mg, 2.0 mmol) in DCE (20 mL) was stirred at 75° C. for 30 min under nitrogen. The reaction mixture was cooled to 0° C., and treated with NaBH(OAc)$_3$ (0.633 g, 3.0 mmol). The reaction was allowed to proceed overnight with stirring at room temperature. The reaction mixture was quenched with water and concentrated under reduced pressure to afford a residue which was purified by on a Biotage SP4 utilizing a gradient of 5-50% MeOH in DCM to afford (S)-4-(3-((S)-6-(bis((1-(2-tert-butoxy-2-oxoethyl)-1H-imidazol-2-yl)methyl)amino)-1-tert-butoxy-1-oxohexan-2-yl)ureido)-5-tert-butoxy-5-oxopentanoic acid (300 mg, 52%) as a colorless oil. $^1$H NMR (400 MHz, CDCl$_3$) δ 6.99 (s, 2H), 6.84 (s, 2H), 4.57 (s, 4H), 4.29-4.19 (m, 2H), 3.66-3.56 (m, 4H), 2.98-2.90 (m, 2H), 2.49-2.37 (m, 4H), 1.95-1.41 (m, 42H); ESMS m/z: 410.8 (M/2+H)$^+$.

D. Synthesis of (S)-tert-butyl 6-(bis((1-(2-tert-butoxy-2-oxoethyl)-1H-imidazol-2-yl)methyl)amino)-2-(3-((S)-1-tert-butoxy-1,5-dioxo-5-(4-sulfamoylphenethyl amino)pentan-2-yl)ureido)hexanoate

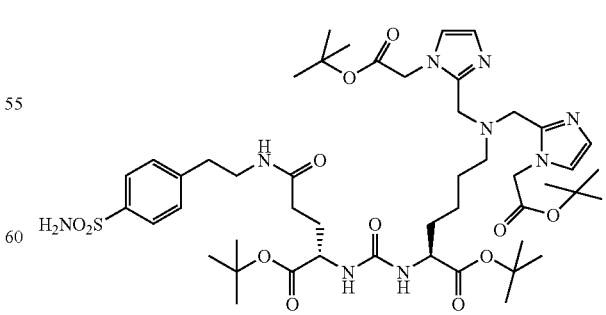

A solution of (S)-4-(3-((S)-6-(bis((1-(2-tert-butoxy-2-oxoethyl)-1H-imidazol-2-yl)methyl)amino)-1-tert-butoxy-1-oxohexan-2-yl)ureido)-5-tert-butoxy-5-oxopentanoic acid (80 mg, 0.098 mmol), 4-(2-aminoethyl)benzenesulfonamide (30 mg, 0.15 mmol), HATU (50 mg, 0.17 mmol), and DIPEA (0.50 mL) in DMF (5 mL) was stirred at 40° C. overnight. The solvents were evaporated under reduced pressure to give a residue, which was purified by Biotage SP4 using a gradient of 0-20% MeOH in DCM to give (S)-tert-butyl 6-(bis((1-(2-tert-butoxy-2-oxoethyl)-1H-imidazol-2-yl)methyl)amino)-2-(3-((S)-1-tert-butoxy-1,5-dioxo-5-(4-sulfamoylphenethylamino)pentan-2-yl)ureido)hexanoate (100 mg, 100%). ESMS m/z: 501.9 (M/2+H)⁺.

E. [Re(CO)₃][(S)-6-(bis((1-(carboxymethyl)-1H-imidazol-2-yl)methyl)amino)-2-(3-((S)-1-carboxy-4-oxo-4-(4-sulfamoylphenethylamino)butyl)ureido)hexanoic acid]. A solution of (S)-tert-butyl 6-(bis((1-(2-tert-butoxy-2-oxoethyl)-1H-imidazol-2-yl)methyl)amino)-2-(3-((S)-1-tert-butoxy-1,5-dioxo-5-(4-sulfamoylphenethylamino)pentan-2-yl)ureido)hexanoate (60 mg, 0.060 mmol) and [NEt₄]₂[ReBr₃(CO)₃] (60 mg, 0.077 mmol) in MeOH (4.0 mL) was stirred at 80° C. overnight in a sealed pressure tube. The solvent was evaporated under reduced pressure to give a residue. A solution of the above isolated residue was dissolved in DCM (2.0 mL) and TFA (2.0 mL) was added and the reaction mixture was stirred at room temperature for 2 h. The solvent was removed under reduced pressure to afford a residue, which was purified by HPLC to give the title compound (16 mg, 25% over 2 steps) as a white solid. ¹H NMR (400 MHz, DMSO-d₆) δ 7.94 (brs, 1H), 7.71 (d, J=8.4 Hz, 2H), 7.35 (d, J=8.4 Hz, 2H), 7.26 (s, 2H), 7.17 (s, 2H), 7.03 (s, 2H), 6.37-6.33 (m, 2H), 4.83 (s, 4H), 4.55 (d, J=16.4 Hz, 2H), 4.39 (d, J=16.4 Hz, 2H), 4.14-4.02 (m, 2H), 3.65-3.61 (m, 2H), 3.25-3.22 (m, 2H), 2.74 (t, J=7.0 Hz, 2H), 2.05-1.30 (m, 10H); ESMS m/z: 524.8 (M/2+H)⁺.

Example 12

(S)-2-(3-((S)-1-carboxy-4-oxo-4-(4-sulfamoylphenylamino) butyl)ureido)-6-(3-iodobenzamido)hexanoic acid

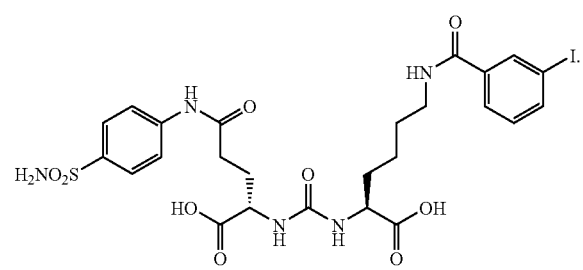

A. 2,5-dioxopyrrolidin-1-yl 3-iodobenzoate

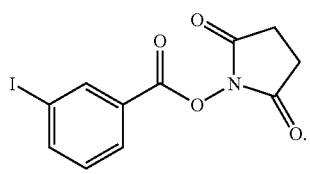

A solution of 3-iodobenzoic acid (744 mg, 3.0 mmol), N,N'-disuccinimidyl carbonate (920 mg, 3.6 mmol) and pyridine (0.30 mL) in acetonitrile (30 mL) was stirred at room temperature overnight. Solvent was removed under reduced pressure to give a residue, which was purified utilizing a Biotage SP4 eluting with 10% to 100% EtOAc in hexanes to afford 2,5-dioxopyrrolidin-1-yl 3-iodobenzoate (946 mg, 91%) as a white solid. ¹H NMR (400 MHz, CDCl₃) δ 8.46 (s, 1H), 8.10 (d, J=7.6, 1H), 8.00 (d, J=8.0 Hz, 1H), 7.26 (t, J=7.8 Hz, 1H), 2.91 (s, 4H); ESMS m/z: 368 (M+Na)⁺.

B. (S)-5-tert-butoxy-4-(3-((S)-1-tert-butoxy-6-(3-iodobenzamido)-1-oxohexan-2-yl)ureido)-5-oxopentanoic acid

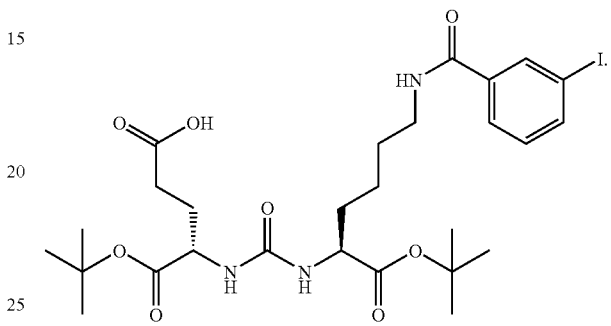

A solution of (S)-4-(3-((S)-6-amino-1-tert-butoxy-1-oxohexan-2-yl)ureido)-5-tert-butoxy-5-oxopentanoic acid (260 mg, 0.60 mmol), 5-dioxopyrrolidin-1-yl 3-iodobenzoate (276 mg, 0.80 mmol), and DIPEA (1.0 mL) in DMF (5.0 mL) was stirred at room temperature overnight. The solvents were removed under reduced pressure to afford a residue, which was purified utilizing a Biotage SP4 eluting with 10% to 100% EtOAc in hexanes to afford (S)-5-tert-butoxy-4-(3-((S)-1-tert-butoxy-6-(3-iodobenzamido)-1-oxohexan-2-yl)ureido)-5-oxopentanoic acid (343 mg, 86%) as a colorless oil. ESMS m/z: 332 (M+H)/2⁺.

C. (S)-2-(3-((S)-1-carboxy-4-oxo-4-(4-sulfamoylphenylamino)butyl) reido)-6-(3-iodobenzamido)hexanoic acid. A solution of (S)-5-tert-butoxy-4-(3-((S)-1-tert-butoxy-6-(3-iodobenzamido)-1-oxohexan-2-yl)ureido)-5-oxopentanoic acid (98 mg, 0.148 mmol), sulfanilamide (34.4 mg, 0.20 mmol), HATU (76 mg, 0.20 mmol), and DIPEA (0.50 mL) in DMF (5 mL) was stirred at 50° C. overnight. The solvents were evaporated under reduced pressure to give a residue, which was purified utilizing a Biotage SP4 with a gradient of 10-100% EtOAc in hexane to give (S)-tert-butyl 2-(3-((S)-1-tert-butoxy-1,5-dioxo-5-(4-sulfamoylphenylamino)pentan-2-yl)ureido)-6-(3-iodobenzamido)hexanoate. A solution of the above isolated material was dissolved in a mixture of TFA (2.0 mL)/DCM (2.0 mL) and stirred at room temperature for 3 h. The solvents were removed under reduced pressure to give a residue, which was purified by HPLC to give the title compound (20 mg, 19% over 2 steps) as a white solid. ESMS m/z: 704.2 (M+H)⁺.

Example 13

(S)-2-(3-((S)-1-carboxy-4-oxo-4-(4-sulfamoylphenethylamino)butyl)ureido)-6-(3-iodobenzamido)hexanoic acid

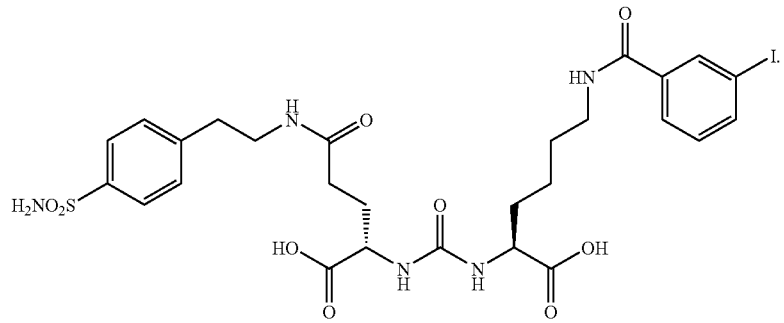

A solution of (S)-5-tert-butoxy-4-(3-((S)-1-tert-butoxy-6-(3-iodobenzamido)-1-oxohexan-2-yl)ureido)-5-oxopentanoic acid (212 mg, 0.32 mmol), 4-(2-aminoethyl)benzenesulfonamide (80 mg, 0.40 mmol), HATU (152 mg, 0.40 mmol), and DIPEA (0.50 mL) in DMF (5 mL) was stirred at 50° C. overnight. The solvents were evaporated under reduced pressure to give a residue, which was purified utilizing a Biotage SP4 with a gradient of 10-100% EtOAc in hexane to give (S)-tert-butyl 2-(3-((S)-1-tert-butoxy-1,5-dioxo-5-(4-sulfamoylphenylamino)pentan-2-yl)ureido)-6-(3-iodobenzamido)hexanoate. A solution of the above product was dissolved in TFA (2.0 mL)/DCM (2.0 mL) and stirred at room temperature for 3 h. The solvents were removed under reduced pressure to give a residue, which was purified by Amberchrom™ to give ((S)-2-(3-((S)-1-carboxy-4-oxo-4-(4-sulfamoylphenethylamino)butyl)ureido)-6-(3-iodobenzamido)hexanoic acid (40 mg, 17% over 2 steps) as a white solid. $^1$H NMR (400 MHz, DMSO-$d_6$) δ 8.54 (t, J=5.4 Hz, 1H), 8.17 (s, 1H), 7.97 (t, J=5.4 Hz, 1H), 7.86 (d, J=8.0 Hz, 1H), 7.83 (d, J=8.0 Hz, 1H), 7.72 (d, J=8.4 Hz, 2H), 7.37 (d, J=8.0 Hz, 2H), 7.28-7.23 (m, 3H), 6.32 (t, J=7.0 Hz, 2H), 4.07-3.99 (m, 2H), 3.27-2.80 (m, 2H), 2.75 (t, J=7.2 Hz, 2H), 2.10-1.29 (m, 10H); ESMS m/z: 732.2 (M+H)$^+$.

Synthesis of Exemplary Formula IV Compounds

Example 14

[Re(CO)$_3$][2-((6-oxo-6-(4-sulfamoylphenylamino)hexyl) (pyridin-2-ylmethyl)amino)acetic acid]

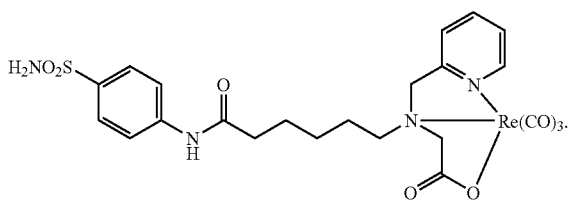

A. 6-((2-tert-butoxy-2-oxoethyl)(pyridin-2-ylmethyl)amino)hexanoic acid

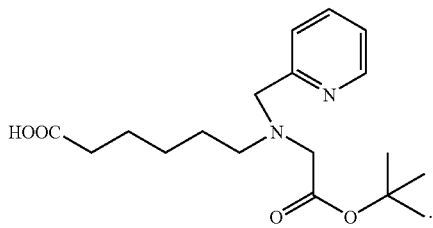

A solution of 6-aminohexanoic acid (1.97 g, 15 mmol) and 2-pyridinecarboxaldehyde (1.61 g, 15 mmol) in DCE (30 mL) was heated at 75° C. for 30 min under nitrogen. The reaction mixture was cooled to 0° C., and treated sequentially with NaBH(OAc)$_3$ (7.95 g, 37.5 mmol) and tert-butyl glyoxalate (2.80 g)$^1$. The reaction mixture was stirred at room temperature overnight and quenched with water. The reaction mixture was extracted with DCM and the combined organic layers were dried and concentrated under reduced pressure. The residue was purified by flash chromatography over silica gel to afford 6-(2-tert-butoxy-2-oxoethyl)(pyridin-2-ylmethyl)amino)hexanoic acid (1.78 g, 35%) as a yellow oil. $^1$H NMR (400 MHz, CD$_3$Cl$_3$) δ 8.57 (ddd, J=4.8, 1.6, 0.8 Hz, 1H), 7.70 (td, J=7.6, 1.6 Hz, 1H), 7.56 (d, J=7.6, 1H), 7.22-7.18 (m, 1H), 3.93 (s, 2H), 3.29 (s, 2H), 2.65 (t, J=7.4 Hz, 2H), 2.33 (t, J=7.6 Hz, 2H), 1.67-1.32 (m, 15H); ESMS m/z: 337.2 (M+H)$^+$.

B. tert-butyl 2-((6-oxo-6-(4-sulfamoylphenylamino)hexyl)(pyridin-2-ylmethyl)amino)acetate

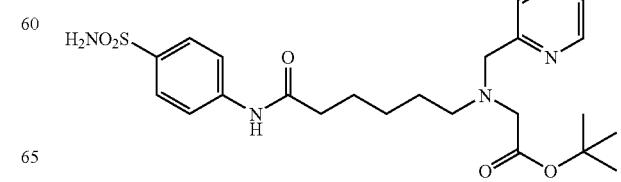

A solution of 6-((2-tert-butoxy-2-oxoethyl)(pyridin-2-ylmethyl)amino)hexanoic acid (0.6545 g, 1.95 mmol), sulfanilamide (0.362 g, 2.10 mmol) and HATU (0.798 g, 2.10 mmol) in DMF (10 mL) and Et$_3$N (1.0 mL) was stirred at 40° C. overnight. The reaction mixture was purified by flash chromatography over silica gel eluting with MeOH/DCM to give tert-butyl 2-((6-oxo-6-(4-sulfamoylphenylamino)hexyl)(pyridin-2-ylmethyl)amino)acetate (297 mg, 31%). ESMS m/z: 491.3 (M+H)$^+$.

C. [Re(CO)$_3$][2-((6-oxo-6-(4-sulfamoylphenylamino)hexyl)(pyridin-2-ylmethyl)amino)acetic acid]. A solution of tert-butyl 2-((6-oxo-6-(4-sulfamoylphenylamino) hexyl)(pyridin-2-ylmethyl)amino)acetate (70 mg, 0.14 mmol) in DCM (1.0 mL) and TFA (1.0 mL) was stirred at room temperature overnight. The solvent was removed under reduced pressure to give 2-((6-oxo-6-(4-sulfamoylphenylamino)hexyl)(pyridin-2-ylmethyl)amino) acetic acid. A solution of the above isolated product, 2-((6-oxo-6-(4-sulfamoylphenylamino) hexyl)(pyridin-2-ylmethyl)amino)acetic acid, [NEt$_4$]$_2$ [ReBr$_3$(CO)$_3$] (108 mg, 0.14 mmol) and potassium carbonate (30 mg) in MeOH (4.0 mL) and water (1.0 mL) was stirred at 100° C. for 4 h in a sealed pressure tube. The reaction mixture was purified by Amberchrom™ eluting with MeOH/H$_2$O to give the title compound (64 mg, 65%) as a white solid. $^1$H NMR (400 MHz, DMSO-d$_6$) δ 10.25 (s, 1H), 8.74 (d, J=5.2 Hz, 1H), 8.13 (td, J=7.6, 1.2 Hz, 1H), 7.76-7.55 (m, 5H), 7.56 (t, J=6.4 Hz, 1H), 7.23 (s, 2H), 4.74 (d, J=16.0 Hz, 1H), 4.53 (d, J=16.0 Hz, 1H), 3.82 (d, J=16.8 Hz, 1H), 3.54-3.40 (m, 2H), 3.38 (d, J=16.8 Hz, 1H), 2.38 (t, J=7.4 Hz, 2H), 1.76-1.31 (m, 6H); ESMS m/z: 705.3 (M+H)$^+$.

Example 15

Rhenium(tricarbonyl)(11-(bis(pyridin-2-ylmethyl)amino)-N-(4-sulfamoylphenethyl)undecanamide)

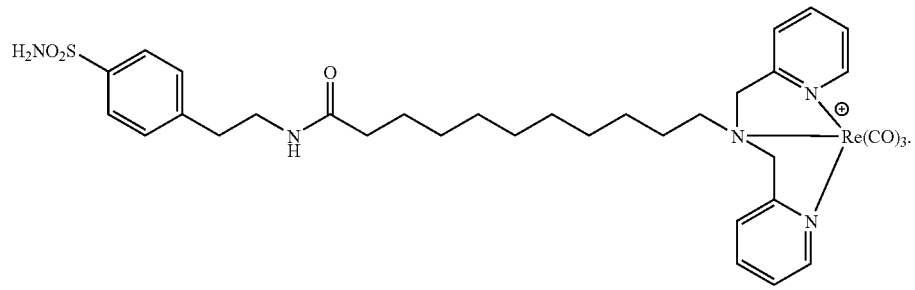

A. 11-(Bis(pyridin-2-ylmethyl)amino)-N-(4-sulfamoylphenethyl)undecanamide was prepared as set forth above in the procedures described in the "General Synthetic Methods" section (139 mg, 31%). ESMS m/z: 568 (M+H)$^+$.

B. Rhenium(tricarbonyl)(11-(bis(pyridin-2-ylmethyl)amino)-N-(4-sulfamoylphenethyl) undecanamide)), was prepared from the compound of step A, according to the procedure as described in the "General Procedure for Complexation of Rhenium" section, and recovered (10 mg, 19%) as an off-white solid. $^1$H NMR (400 MHz, DMSO-d$_6$) δ 8.75 (d, 2H), 7.95 (m, 2H), 7.90 (t, H), 7.7 (d, 2H), 7.55 (d, 2H), 7.3 (m, 4H), 7.2 (m, 2H), 4.8 (m, 4H), 4.15 (d, 2H), 3.75 (m, 2H), 3.3 (m, 2H), 2.83 (m, 2H), 1.85 (m, 2H), 1.35 (m, 14H). ESMS m/z: 460 (M+H)$^+$.

Example 16

Rhenium(tricarbonyl)(11-(bis(pyridin-2-ylmethyl)amino)-N-(4-sulfamoylbenzyl)undecanamide)

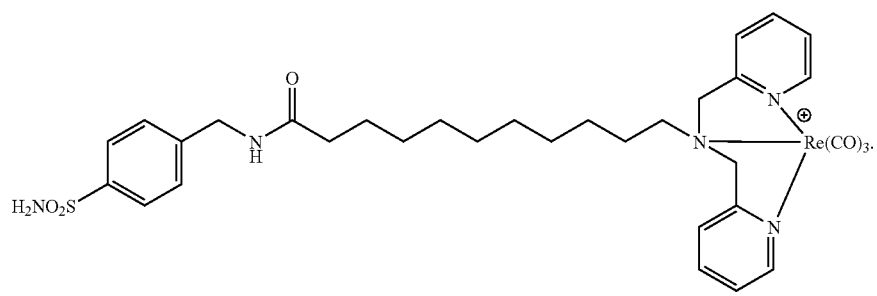

A. 11-(bis(pyridin-2-ylmethyl)amino)-N-(4-sulfamoylbenzyl) undecanamide was prepared according to the procedure described above in the "General Synthetic Methods" section (100 mg, 23%). ESMS m/z: 552 (M+H)+.

B. Rhenium(tricarbonyl)(11-(bis(pyridin-2-ylmethyl)amino)-N-(4-sulfamoylbenzyl)undecanamide)), was prepared from the compound of step A, as described above in the "General Procedure for Complexation of Rhenium" section (22 mg, 36%) as an off-white solid. $^1$H NMR (400 MHz, DMSO-d$_6$) δ 8.82 (d, 2H), 8.45 (t, 1H), 8.0 (m, 2H), 7.8 (d, 2H), 7.55 (d, 2H), 7.40 (m, 4H), 7.30 (s, 2H), 4.90 (d, 4H), 4.30 (m, 2H), 3.70 (m, 2H), 1.80 (bs, 2H), 1.57 (m, 2H), 1.38 (m, 14H). ESMS m/z: 823 (M+H)+.

Example 17

Rhenium(tricarbonyl)(11-(bis(pyridin-2-ylmethyl)amino)-N-(4-sulfamoylphenyl)undecanamide)

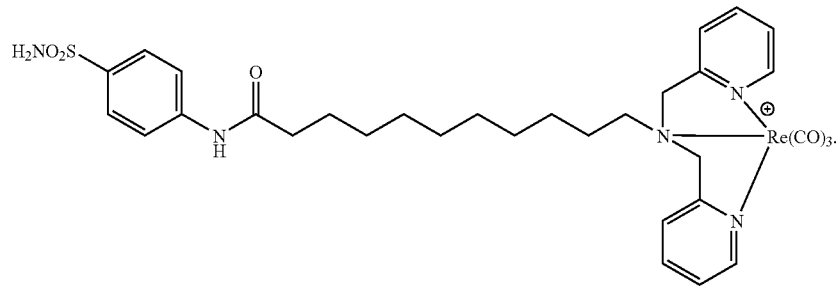

A. 11-(Bis(pyridin-2-ylmethyl)amino)-N-(4-sulfamoylphenyl) undecanamide was prepared as described above in the "General Synthetic Methods" section (41 mg, 15%). ESMS m/z: 538 (M+H)+.

B. Rhenium(tricarbonyl)(11-(bis(pyridin-2-ylmethyl)amino)-N-(4-sulfamoylphenyl)undecanamide), was prepared from the compound of step A, as described above in the "General Procedure for Complexation of Rhenium" section (15 mg, 33%), as an off-white solid. $^1$H NMR (400 MHz, DMSO-d$_6$) δ 10.25 (s, 1H), 8.83 (d, 2H), 8.00 (m, 2H), 7.80 (s, 4H), 7.55 (d, 2H), 7.40 (m, 2H), 7.20 (s, 2H), 4.90 (d, 4H), 4.30 (m, 2H), 3.60 (m, 2H), 2.30 (m, 2H), 1.80 (bs, 2H), 1.57 (m, 2H), 1.38 (m, 10H). ESMS m/z: 808 (M+H)+.

Example 18

Rhenium(tricarbonyl)(3-(2-(2-(bis(pyridin-2-ylmethyl)amino)ethoxy)ethoxy)-N-(4-sulfamoylphenethyl)propanamide)

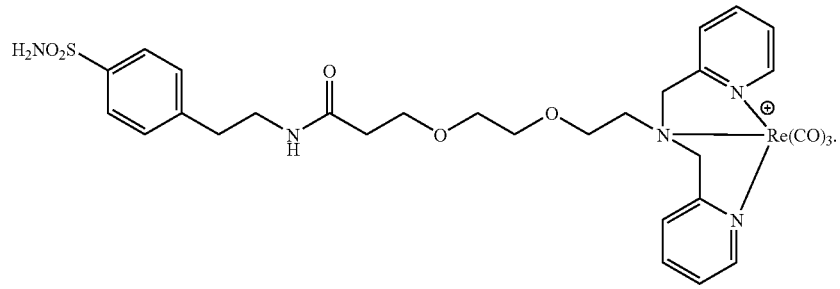

A. 3-(2-(2-(bis(pyridin-2-ylmethyl)amino)ethoxy)ethoxy)-N-(4-sulfamoylphenethyl)propanamide, was prepared as described above in the "General Synthetic Methods" section afforded the desired product (70 mg, 16%). ESMS m/z: 542 (M+H)+.

B. Rhenium(tricarbonyl)(3-(2-(2-(bis(pyridin-2-ylmethyl)amino)ethoxy)ethoxy)-N-(4-sulfamoylphenethyl)propanamide), was prepared from the compound of step A, as described above in the "General Procedure for Complexation of Rhenium" (36 mg, 44%), as an off-white solid. $^1$H NMR (400 MHz, DMSO-$d_6$) δ 8.75 (d, 2H), 7.95 (m, 3H), 7.7 (d, 4H), 7.55 (d, 2H), 7.30 (m, 6H), 4.90 (d, 4H), 4.30 (m, H), 3.80 (m, 2H), 3.55 (m, 4H) 3.40 (m, 2H), 3.30 (s, 2H), 3.17 (m, 2H), 2.72 (t, 2H), 2.25 (t, 2H). ESMS m/z: 812 (M+H)+.

Example 19

Rhenium(tricarbonyl)(3-(2-(2-(bis(pyridin-2-ylmethyl)amino)ethoxy)ethoxy)-N-(4-sulfamoylbenzyl)propanamide)

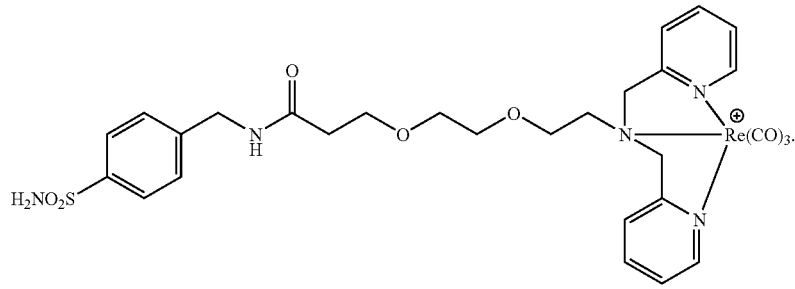

A. 3-(2-(2-(bis(pyridin-2-ylmethyl)amino)ethoxy)ethoxy)-N-(4-sulfamoylbenzyl)propanamide was prepared as described above in the "General Synthetic Methods" section afforded the desired product (126 mg, 43%). ESMS m/z: 542 (M+H)+.

B. Rhenium(tricarbonyl)(3-(2-(2-(bis(pyridin-2-ylmethyl)amino)ethoxy)ethoxy)-N-(4-sulfamoylbenzyl)propanamide), was prepared from the compound of step A, as described in the "General Procedure for Complexation of Rhenium" section (31 mg, 41%), as an off-white solid. $^1$H NMR (400 MHz, DMSO-$d_6$) δ 8.60 (d, 2H), 8.55 (m, H), 7.75 (m, 2H), 7.55 (d, 2H), 7.35 (d, 2H), 7.15 (m, 4H), 4.8 (d, 4H), 4.15 (d, 2H), 3.75 (m, 4H), 3.6 (m, 2H), 3.45 (m, 4H), 3.2 (m, H), 2.25 (t, 2H). ESMS m/z: 798 (M+H)+.

Example 20

Rhenium(tricarbonyl)(3-(2-(2-(bis(pyridin-2-ylmethyl)amino)ethoxy)ethoxy)-N-(4-sulfamoylbenzyl)propanamide

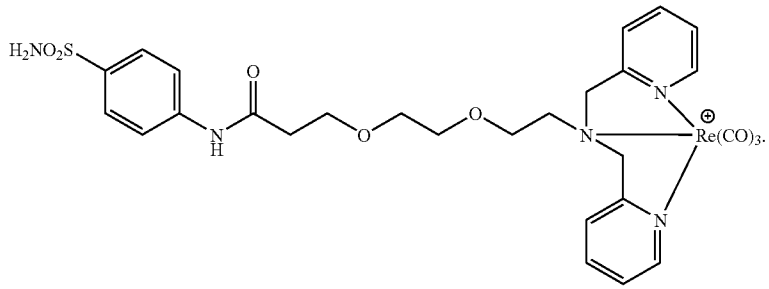

A. 3-(2-(2-(bis(pyridin-2-ylmethyl)amino)ethoxy)ethoxy)-N-(4-sulfamoylbenzyl)propanamide was prepared as described above in the "General Synthetic Methods" section afforded the desired product (41 mg, 10%). ESMS m/z: 512 (M+H)+.

B. Rhenium(tricarbonyl)(3-(2-(2-(bis(pyridin-2-ylmethyl)amino)ethoxy)ethoxy)-N-(4-sulfamoylbenzyl)propanamide was then prepared from the compound of step A, as described above in the "General Procedure for Complexation of Rhenium" section (24 mg, 52%), as an off-white solid. $^1$H NMR (400 MHz, DMSO-$d_6$) δ 8.80 (m, 2H), 7.95 (m, 2H), 7.60 (m, 4H), 7.4 (m, 4H), 4.95 (m, 4H), 3.95 (m, 4H), 3.65 (m, 4H), 2.65 (m, 4H). ESMS m/z: 798 (M+H)+.

Example 21

Rhenium(tricarbonyl) 11-(bis((1-methyl-1H-imidazol-2-yl)methyl)amino)-N-(4-sulfamoylphenyl)undecanamide

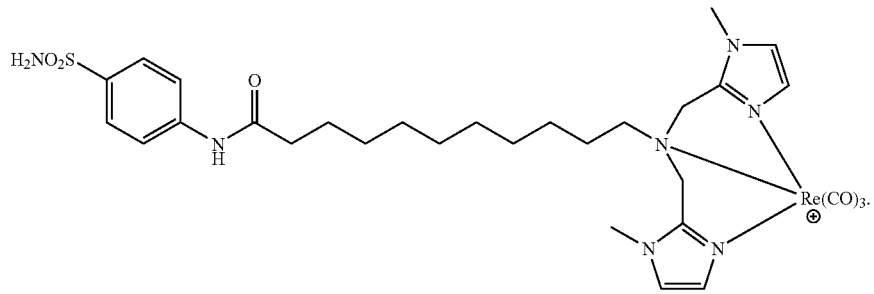

A. 11-(bis((1-methyl-1H-imidazol-2-yl)methyl)amino)-N-(4-sulfamoylphenyl)undecanamide was prepared as described above in the "General Synthetic Methods" section afforded 1 (38 mg, 10%). ESMS m/z: 544 (M+H)+.

B. Rhenium(tricarbonyl) 11-(bis((1-methyl-1H-imidazol-2-yl)methyl)amino)-N-(4-sulfamoylphenyl)undecanamide was prepared from the compound of step A, and as described above in the "General Procedure for Complexation of Rhenium" section (18 mg, 36%), as an off-white solid. $^1$H NMR (400 MHz, DMSO-$d_6$) δ 10.30 (s, H), 7.30 (d, 2H), 7.05 (d, 2H), 6.43 (d, 2H), 5.65 (d, 2H), 4.65 (m, 2H), 3.60 (s, 6H), 2.30 (m, 2H), 1.85 (m, 2H), 1.35 (m, 14H). ESMS m/z: 817 (M+H)+.

Example 21A

Rhenium(tricarbonyl) 11-(bis((1-methyl-1H-imidazol-2-yl)methyl)amino)-N-(4-sulfamoylphenyl)octanamide, may be prepared a method analogous to that of Example 22

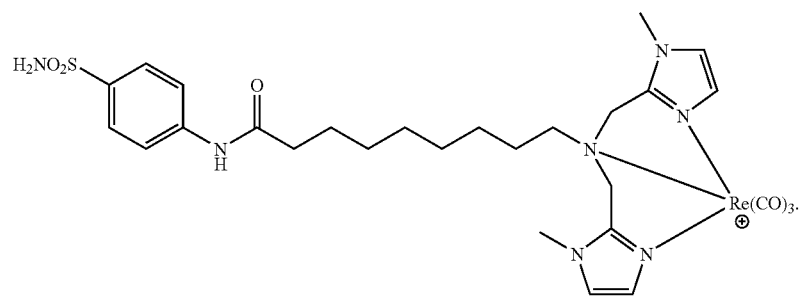

Example 22

Rhenium(tricarbonyl) 6-(bis(pyridin-2-ylmethyl)amino)-N-(4-sulfamoylphenyl)hexanamide

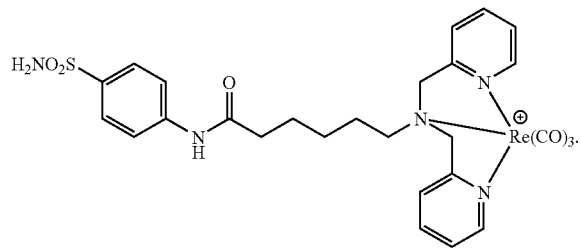

A. 6-(bis(pyridin-2-ylmethyl)amino)-N-(4-sulfamoylphenyl)hexanamide was prepared following the same procedure as described in the "General Synthetic Methods" section (162 mg, 22%). ESMS m/z: 468 (M+H)+.

B. Rhenium(tricarbonyl) 6-(bis(pyridin-2-ylmethyl)amino)-N-(4-sulfamoylphenyl)hexanamide was prepared from the compound of step A, above, and following the procedure as described in the "General Procedure for Complexation of Rhenium" (13 mg, 11%), as an off-white solid. $^1$H NMR (400 MHz, DMSO-d$_6$) δ 10.30 (s, H), 8.82 (d, 2H), 7.98 (t, 2H), 7.75 (m, 4H), 7.55 (d, 2H), 7.40 (m, 2H), 7.20 (d, 2H), 4.90 (m, 4H), 2.45 (m, 4H), 1.85 (m, 2H), 1.65 (m, 2H), 1.35 (m, 2H). ESMS m/z: 742 (M+H)+.

Benzenesulfonamide Analogs Having an Ethylenediaminetetraacetic Acid Linker

Exemplary compounds were synthesized using the protocol illustrated below in Scheme 3. Reaction of 4,4'-(ethane-1,2-diyl)dimorpholino-2,6-dione with an equivalent of 4-aminobenezenesulfonamide, followed by an equivalent of N,N-bis(pyridine-2-ylmethyl)alkyl-1,6,diamine gave the titled compound compounds which were further coordinated to a radionuclide using the general procedure discussed above.

Scheme 3

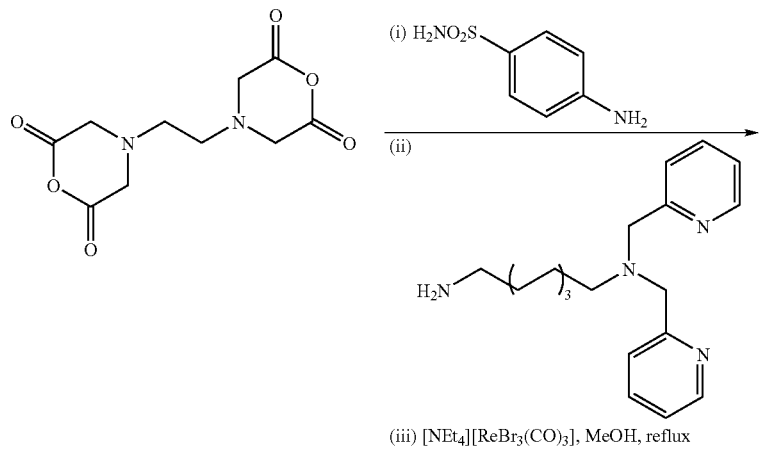

(iii) [NEt$_4$][ReBr$_3$(CO)$_3$], MeOH, reflux

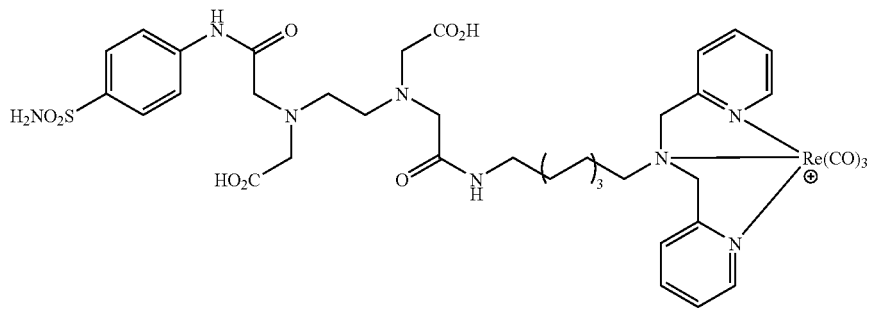

Example 23

A. A solution of EDTA dianhydride (130 mg, 0.50 mmol) and sulfanilamide (86 mg, 0.50 mmol) in DMF (3.0 mL) were stirred at room temperature for 4 h. $N^1,N^1$-bis(pyridin-2-ylmethyl)octane-1,8-diamine (162 mg, 0.50 mmol) were added to the reaction mixture and the reaction mixture was stirred at room temperature overnight. The solvents were evaporated under reduced pressure and purified by HPLC to give the desired product (110 mg, 29%) as a white solid. ESMS m/z: 378.2 $(M/2+H)^+$.

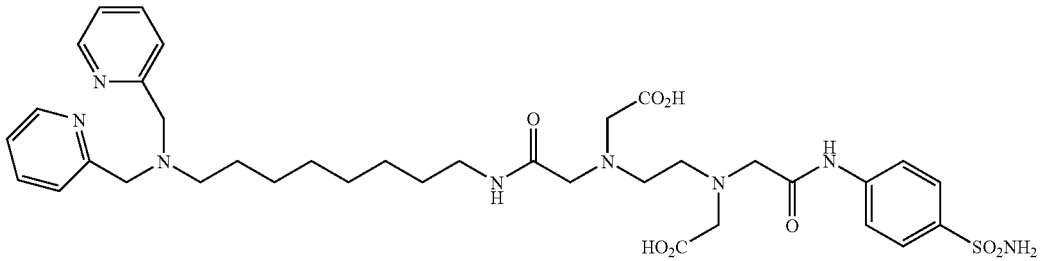

B. A solution of the above compound from step A (20 mg, 0.026 mmol), $[NEt_4]_2[ReBr_3(CO)_3]$ (23 mg, 0.030 mmol) and potassium carbonate (5 mg) in MeOH (5.0 mL) was stirred at 100° C. overnight in a pressure tube. The reaction mixture was concentrated and purified by HPLC to give the desired compound (5.3 mg) as a white solid. ESMS m/z: 513.3 $(M/2+H)^+$.

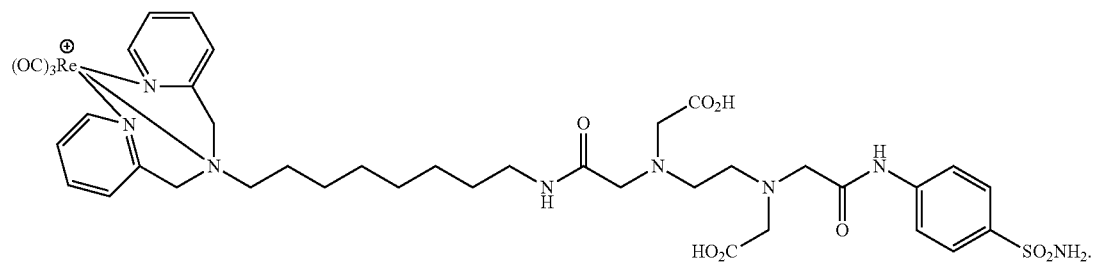

Example 24

The compound of the following formula is prepare by a method analogous to that of Example 24

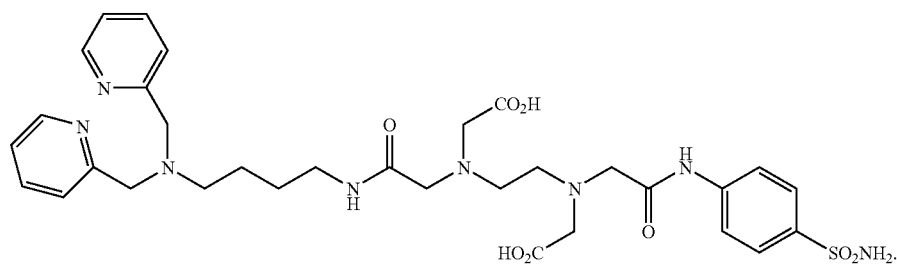

Example 25

Rhenium(tricarbonyl)[4-[3-(2-{2-[2-(Bis-pyridin-2-ylmethyl-amino)-ethoxy]-ethoxy}-ethyl)-thioureido]-benzenesulfonamide] may be prepared by appropriate modification of the above synthetic methods

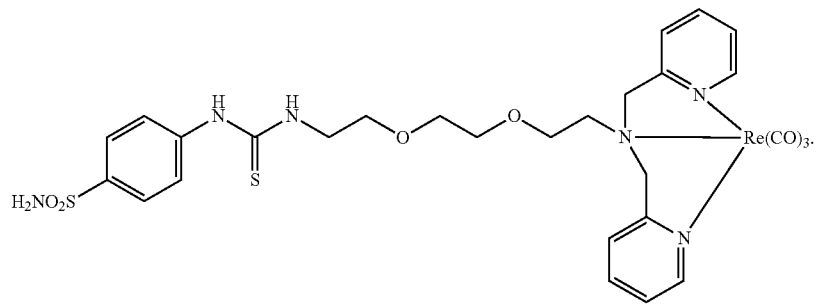

Selective Inhibition of Carbonic Anhydrase Activity

Compounds were tested for their ability to inhibit carbonic anhydrase isozymes II and IX in vitro. Purified human enzymes were from R&D Systems (Minneapolis, Minn.). The inhibition constants ($K_i$) for CA-II and CA-IX were determined by the method of Pocker and Stone [25]. Initial rates of 4-nitrophenyl acetate hydrolysis catalyzed by the different carbonic anhydrase isozymes were measured spectrophotometrically at 400 nm. Solutions of substrate ($1\times10^{-2}$ to $1\times10^{-6}$ M) were prepared in anhydrous acetonitrile. A molar extinction coefficient of 18,000 $M^{-1} \cdot cm^{-1}$ was used for the 4-nitrophenolate formed by hydrolysis under the conditions of the experiment (9 mM Tris-HCl, 81 mM NaCl, pH 7.4, 25° C.). The enzyme concentrations were 100 nM for CA-IX and 30 nM for CA-II. Non-enzymatic hydrolysis rates, determined in the absence of added enzyme, were subtracted from the observed rates. Stock solutions of inhibitor were made up in deionized water with 10-20% DMSO (which does not inhibit the enzymatic activity) [12]. Dilutions of inhibitor were added to enzyme solutions and preincubated for 10 min to allow for the formation of the E-I complex prior to the addition of substrate. Acetazolamide was included in all assays as positive controls

TABLE 1

$IC_{50}$ (nM) results for several examples and comparative examples.

| Example | $IC_{50}$ (nM) | |
|---|---|---|
| | CA-II | CA-IX |
| Comparative Example 1 (see below) | 377 | 77 |
| Comparative Example 2 (see below) | 122 | 54 |
| 6 | 261 | 30 |
| 5 | 360 | 172 |
| 3 | 579 | 43 |
| 9 | 237 | 153 |
| 8 | 577 | 93 |
| Comparative Acetazolamide (See below) | 46 | 32 |

Structure of Comparative Example 1

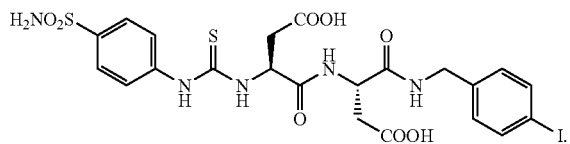

Structure of Comparative Example 2

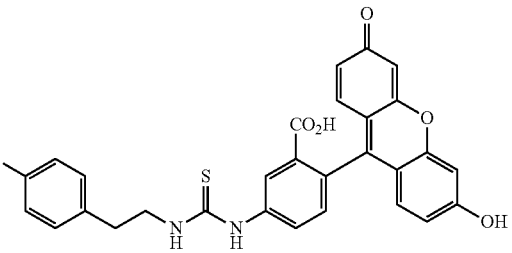

Structure of Comparative Acetazolamide

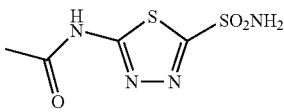

Tissue Biodistribution in Human Xenograft Bearing Mice

Uptake of radiolabeled CA-IX inhibitors in human tumor xenograft models were performed according to published methods [20]. Based on the Western Blot and cell culture data described in Specific Aim 3, we decided to investigate the ability of our compounds to target CA-IX in HeLa xenografts as well as the SK-RC-52 xenografts. Briefly, HeLa, SK-RC- 52, and SK-RC-59 cells were grown according to the supplier's protocols. Prior to inoculation, cells were trypsinized, counted, and suspended in 50% PBS with 1 mg/ml D-glucose, 36 µg/ml sodium pyruvate, 50% Matrigel (BD Biosciences, Franklin Lakes, N.J.). NCr$^{nu/nu}$ mice were anesthetized by intraperitoneal injection of 0.5 ml Avertin (20 mg/ml) (Sigma-Aldrich, St. Louis, Mo.) then inoculated subcutaneously into the hind flank with 2×10$^6$ cells in a 0.25 ml suspension volume. Studies of tumor uptake were conducted when the tumors reached a size of 100-200 mm$^3$. Tissue distribution was analyzed by administering via the tail vein a bolus injection of approximately 2 µCi/mouse of the radiolabeled CA-IX inhibitors in a constant volume of 0.1 ml. Groups of five animals were euthanized by asphyxiation with carbon dioxide at 1, 4, and 24 hours post injection. Determination of CA-IX specific binding was achieved by co-injection of acetazolamide at a dose of 10 mg/kg. Tissues (tumor, blood, heart, liver, lungs, spleen, large and small intestine, stomach, kidneys, skeletal muscle, and brain) were dissected, excised, weighed wet, transferred to plastic tubes and counted in an automated γ-counter (LKB Model 1282, Wallac Oy, Finland). Tissue time-radioactivity levels are expressed as % injected dose per gram tissue (% ID/g) and % injected dose per organ (% DPO).

Figure 2:
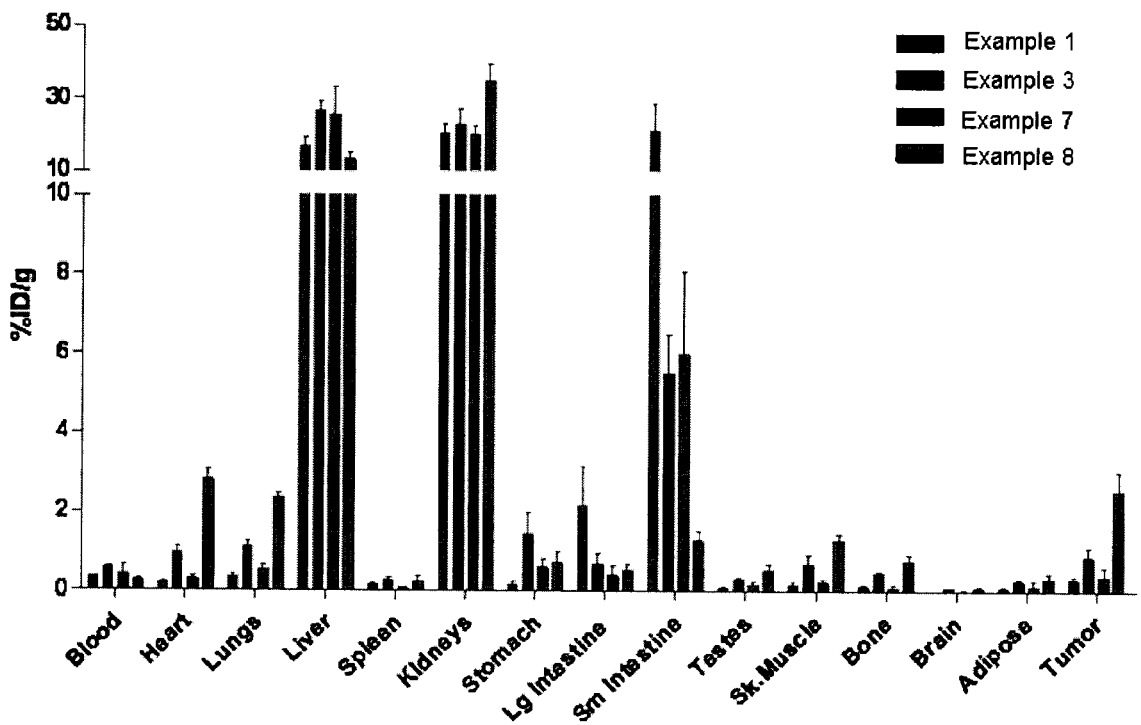
FIG. 2 is a graph comparing the tissue biodistribution in HeLa Xenograft mice of a $^{99m}$Tc analogs of Examples 1, 3, 7, and 8, expressed as % ID/g±(SEM).

The exemplary $^{99m}$Tc analogs were injected into the tail vein of NCr Nude mice bearing CA-IX expressing SK-RC-52 xenografts or HeLa cells. Groups of mice (n=5) were sacrificed at 1 and 4 hr post-injection and the following tissues were harvested: blood, heart, lungs, liver, spleen, kidneys, stomach, large intestines and small intestines (with contents), testes, skeletal muscle, bone, brain, adipose, and tumor. At both time points, an additional group of mice (n=5) were co-injected with 10 mg/kg of acetazolamide to block binding to carbonic anhydrases. FIGS. 1 and 2 show the tissue distribution of various radiopharmaceutical compounds.

Tissue distribution data was generated with a $^{99m}$Tc analog of the compound of Example 8 in HeLa Xenograft mice, expressed as % ID/g±(SEM). The data is presented in FIG. 1.

For reference, in FIG. 2, the tested compounds are $^{99m}$Tc analogs of the compound of Examples 1, 3, 7, and 8 in HeLa Xenograft mice.

Figure 3:
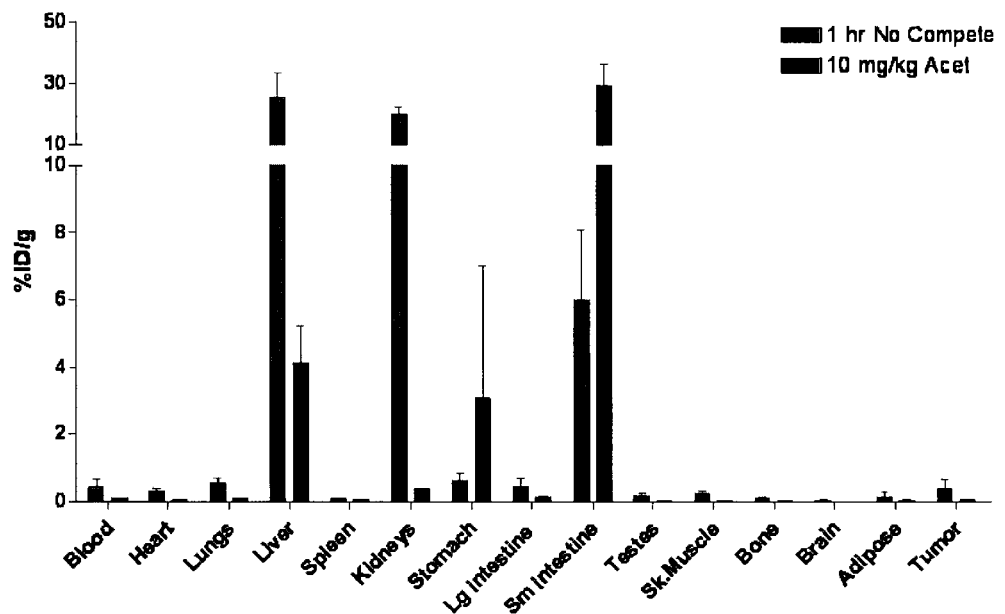
FIG. 3 is a graph of tissue distribution for a $^{99m}$Tc complex of compound of Example 7 in HeLa Xenograft mice, expressed as % ID/g±(SEM).

Tissue distribution data was generated with a $^{99m}$Tc analog of the compound of Example 7 in HeLa Xenograft mice. The data is presented in FIG. 3.

Figure 4:
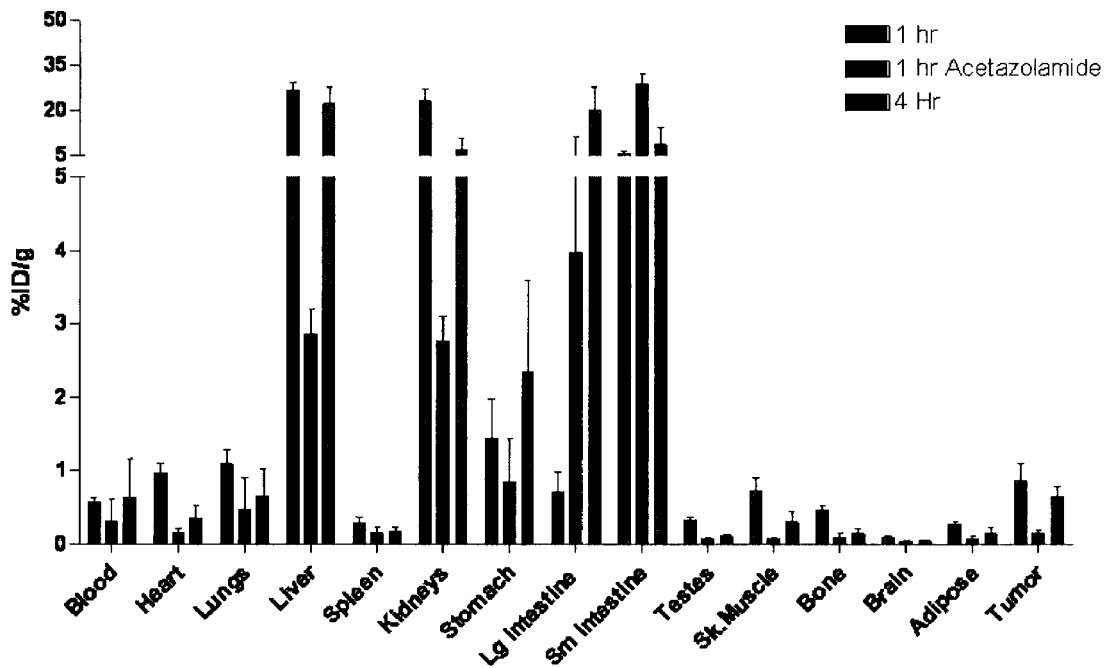
FIG. 4 is a graph of tissue distribution for a $^{99m}$Tc complex of the compound of Example 3 in HeLa Xenograft mice, expressed as % ID/g±(SEM).

Tissue distribution data was generated with a $^{99m}$Tc analog of the compound of Example 3 in HeLa Xenograft mice, expressed as % ID/g±(SEM). The data is presented in FIG. 4.

Figure 5:
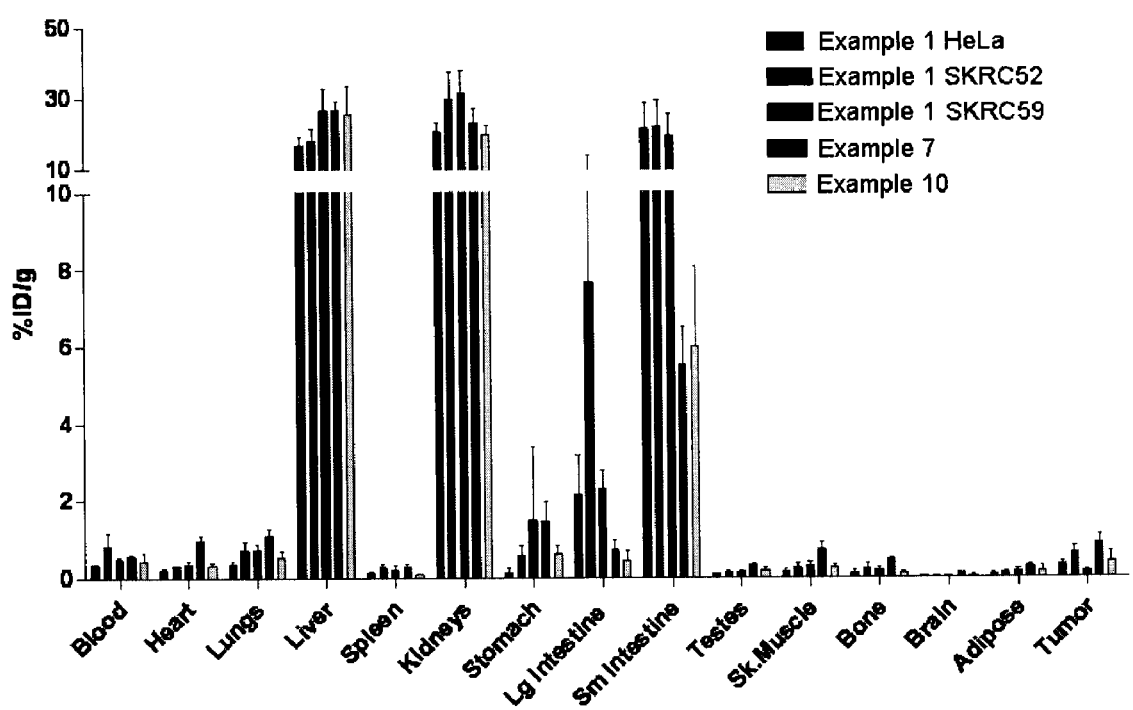
FIG. 5 is a graph of tissue distribution for $^{99m}$Tc analogs of the compound of Example 1 in HeLa, SKRC 52, and SKRC 59 Xenograft mice, and of the compounds of Examples 7 and 10 in HeLa Xenograft mice, expressed as % ID/g±(SEM).

Tissue distribution data was generated with a $^{99m}$Tc analog of the compound of Example 1 in HeLa, SKRC 52, and SKRC 59 Xenograft mice, of the compounds of Examples 7 and 10 in HeLa Xenograft mice. The data are presented in FIG. 5.

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, including the first and last number listed for the range.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A compound of Formula I or a pharmaceutically acceptable salt thereof:

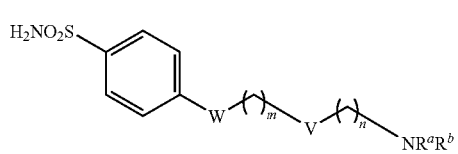

wherein

W is a bond, a (C$_1$-C$_8$)alkyl, a (C$_2$-C$_8$)alkenyl, an aryl, a heteroaryl, a —NHC(O),
—C(O)NH, —NH—C(O)—NH—, or —NH—C(S)—NH—;

V is a bond, a (C$_1$-C$_8$)alkyl, a (C$_2$-C$_8$)alkenyl, an aryl, a heteroaryl, —NH—C(O)—NH—, or —NH—C(S)—NH—;

NR$^a$R$^b$ is a chelator group of Formula:

$R^t$ is H, a C$_1$-C$_8$ alkyl group, an ammonium ion, or an alkali or alkaline earth metal ion;

R$_x$ and R$_y$ is independently hydrogen, alkyl, aminoalkyl, hydroxyalkyl or carboxyalkyl;

R$^v$ is alkyl;

m is an integer from 0 to 15; and n is an integer from 0 to 15.

2. The compound of claim 1, wherein NR$^a$R$^b$ is a chelator group of Formula:

-continued

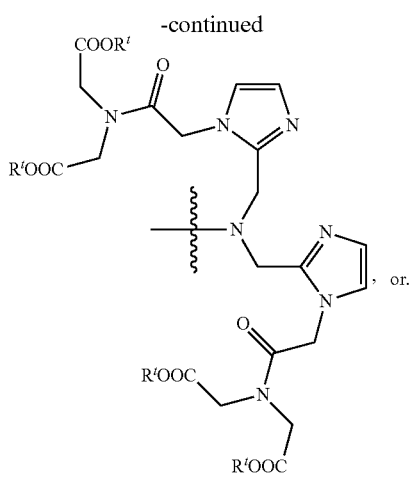

3. The compound of claim 1, wherein $R^v$ is methyl, ethyl, n-propyl, iso-propyl, n-butyl, iso-butyl, or tert-butyl.

4. The compound of claim 1, wherein each $R^t$ is independently H or tert-butyl.

5. The compound of claim 1, wherein m is 0 or 1, and n is an integer from 0 to 8.

6. The compound of claim 1 having the structure:

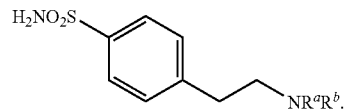

7. The compound of claim 1, wherein $NR^aR^b$ is

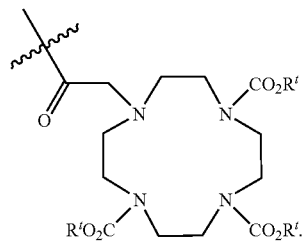

8. The compound of claim 1, wherein $NR^aR^b$ is

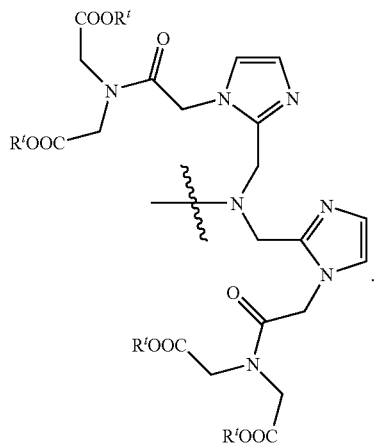

9. A complex comprising the compound of claim 1 and a metal selected from the group consisting of Re, Tc, Y, Lu, Ga, and In.

10. The complex of claim 9, wherein the metal is a radionuclide.

11. The complex of claim 10, wherein the metal is technetium-99m, rhenium-186m, or rhenium-188m.

12. The complex of claim 9, wherein $NR^aR^b$ is

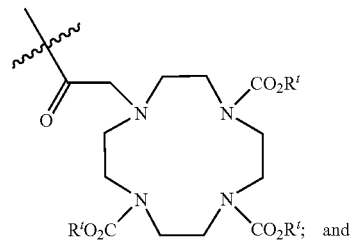

the metal is selected from the group consisting of Y, Ga, Lu, and In.

13. The complex of claim 9, wherein $NR^aR^b$ is

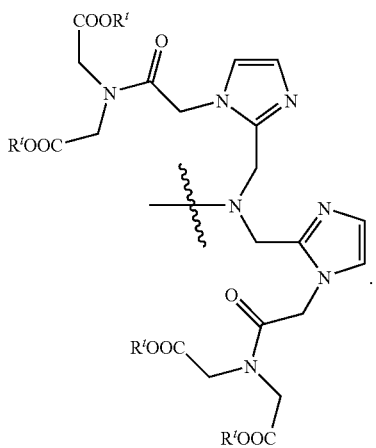

14. The complex of claim 9, which is selected from the group consisting of:

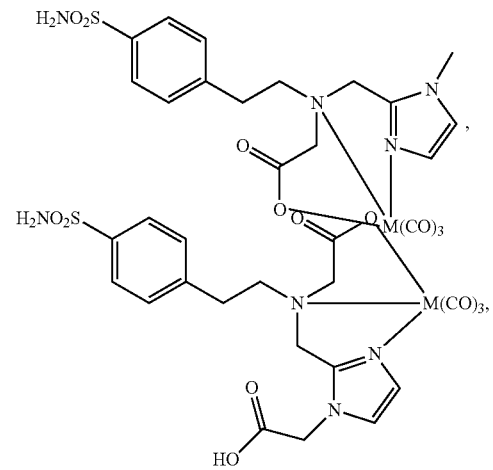

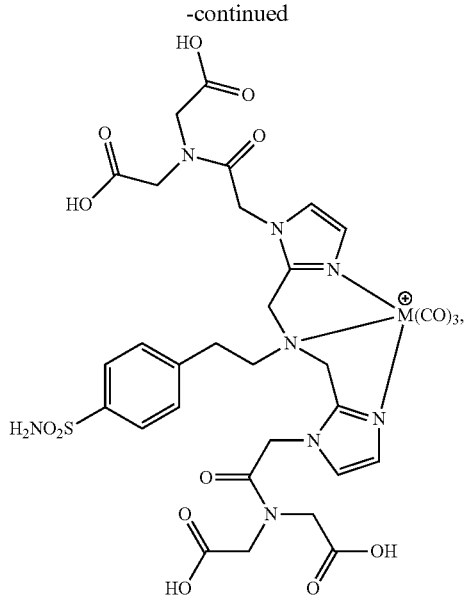
pharmaceutically acceptable salts thereof; and
M is a metal.
15. The complex of claim 14, wherein M is technetium-99m, rhenium-186m, or rhenium-188m.
16. A compound of Formula II or a pharmaceutically acceptable salt, thereof:
II
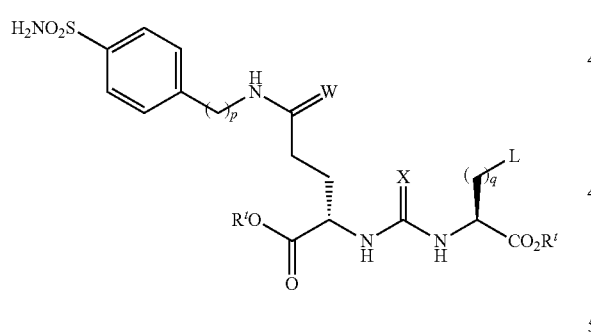
wherein
L is an $NR^aR^b$ chelator group of formula:
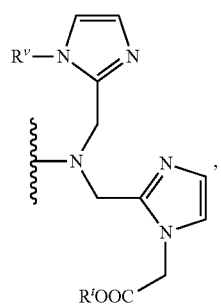
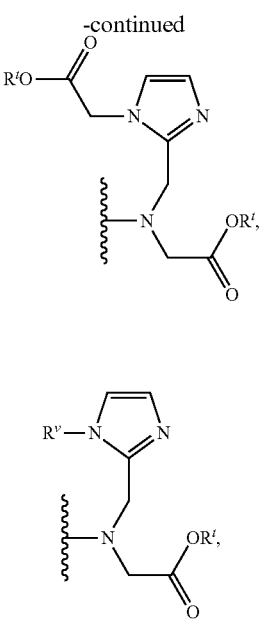
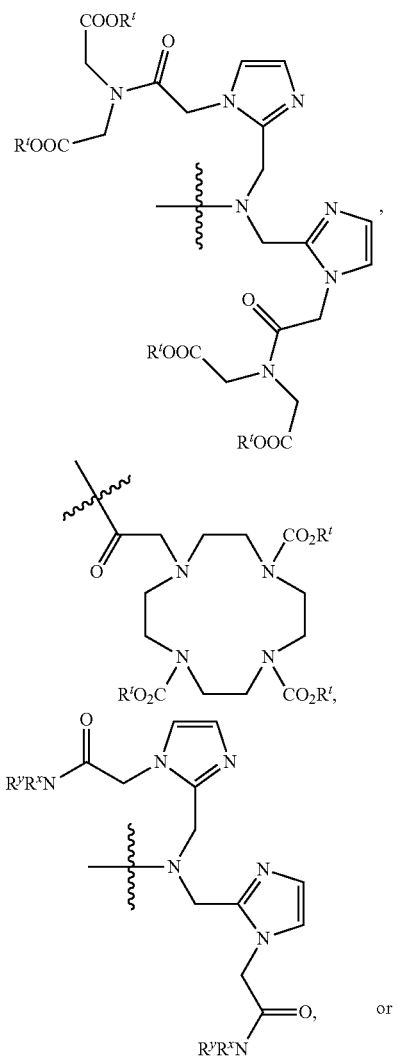
or -continued

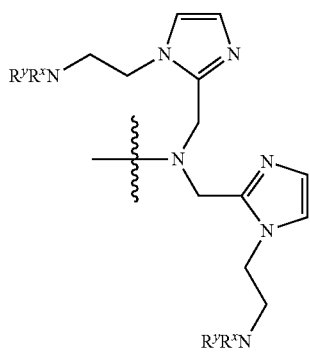

W and X are independently O or S;
p is an integer from 0 to 5;
q is an integer from 0 to 8;
$R^t$ is H, a $C_1$-$C_8$ alkyl group, an ammonium ion, or an alkali or alkaline earth metal ion;
$R_x$ and $R_y$ is independently hydrogen, alkyl, aminoalkyl, hydroxyalkyl or carboxyalkyl; and
$R^y$ is an alkyl.

17. A complex comprising the compound of claim 16, where L is the $NR^aR^b$ chelator group, and a metal.

18. A compound of Formula IV or a pharmaceutically acceptable salt thereof:

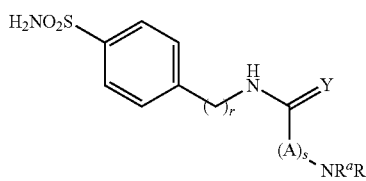

IV wherein
$NR^aR^b$ is a chelator group of Formula:

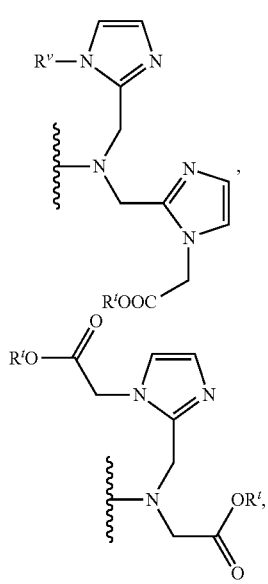

-continued

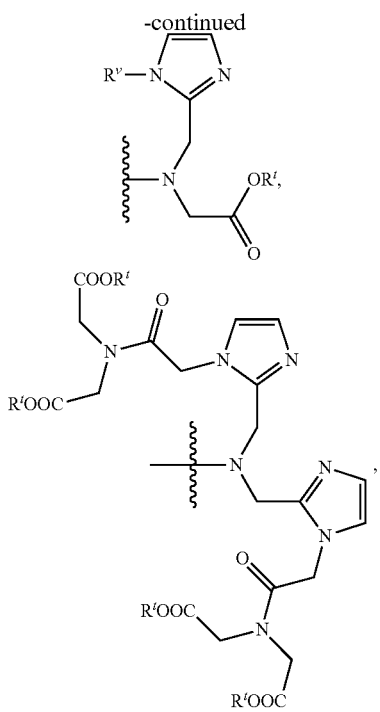

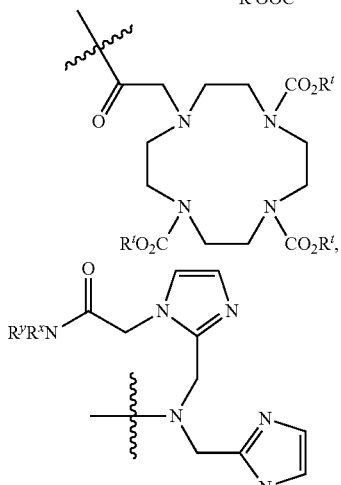

, or

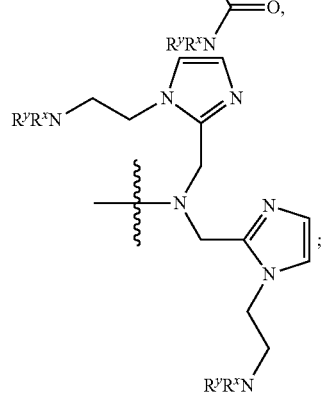

;

Y is O or S;
A is $(C_1$-$C_8)$alkyl, $-(CH_2)_x-(OCH_2CH_2)_y-$ or $-(OCH_2CH_2)_y(CH_2)_x-$;

x is an integer from 0 to 3;

y is an integer from 0 to 3;

r is an integer from 0 to 5;

s is an integer from 0 to 10;

$R^t$ is H, a $C_1$-$C_8$ alkyl group, an ammonium ion, or an alkali or alkaline earth metal ion;

$R_x$ and $R_y$ is independently hydrogen, alkyl, aminoalkyl, hydroxyalkyl or carboxyalkyl; and $R^v$ is an alkyl.

19. The compound of claim 18, wherein r is 0, 1 or 2.

20. The compound of claim 18, wherein s is 0, 5, or 10.

21. The compound of claim 18, wherein $NR^aR^b$ is

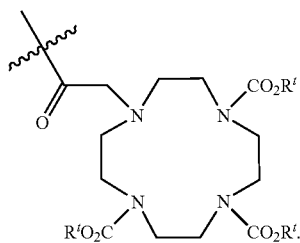

22. The compound of claim 18, wherein $NR^aR^b$ is

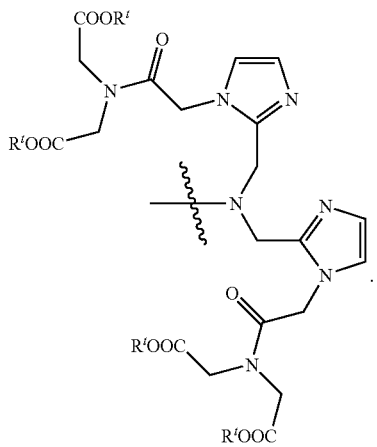

23. A complex comprising the compound of claim 18 and a metal selected from the group consisting of Re, Tc, Y, Lu, Ga, and In.

24. The complex of claim 23, wherein the metal is a radionuclide.

25. The complex of claim 24, wherein the metal is technetium-99m, rhenium-186m, or rhenium-188m.

26. The complex of claim 23, wherein $NR^aR^b$ is

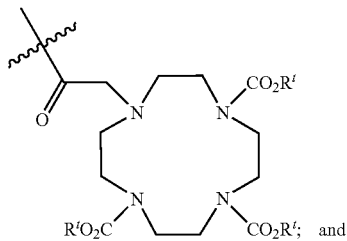

the metal is Y, Ga, Lu, or In.

27. The complex of claim 23, wherein $NR^aR^b$ is

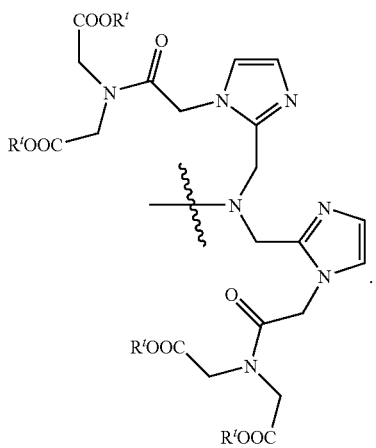

28. The compound of claim 18, wherein $R^v$ is methyl, ethyl, n-propyl, iso-propyl, n-butyl, iso-butyl, or tert-butyl.

29. The compound of claim 18, wherein each $R^t$ is independently H or tert-butyl.

30. A pharmaceutical formulation, comprising the compound according to any one of claims 1, 18, 19, 20, or a pharmaceutically acceptable salt thereof, and a pharmaceutically acceptable excipient.

31. A method of imaging a region in a patient, comprising the steps of: administering to a patient a diagnostically effective amount of a compound of any one of claims 1, 18, 19, 20, or a pharmaceutically acceptable salt thereof, and obtaining an image of the region of the patient.

32. A pharmaceutical formulation, comprising the complex according to any one of claim 9, 17, or 23, or a pharmaceutically acceptable salt thereof, and a pharmaceutically acceptable excipient.

33. A method of imaging a region in a patient, comprising the steps of: administering to a patient a diagnostically effective amount of a complex of any one of claim 9, 17, or 23, or a pharmaceutically acceptable salt thereof, and obtaining an image of the region of the patient.

* * * * *